(12) United States Patent
Sakuraba et al.

(10) Patent No.: US 9,315,790 B2
(45) Date of Patent: *Apr. 19, 2016

(54) POLYNUCLEOTIDES ENCODING PROTEINS HAVING ACQUIRED α-GALACTOSIDASE ACTIVITY

(71) Applicants: TOKYO METROPOLITAN INSTITUTE OF MEDICAL SCIENCE, Tokyo (JP); ALTIF LABORATORIES INC., Tokyo (JP)

(72) Inventors: Hitoshi Sakuraba, Chiba (JP); Youichi Tajima, Tokyo (JP); Ikuo Kawashima, Saitama (JP); Seiichi Aikawa, Tokyo (JP); Fumiko Aikawa, Tokyo (JP)

(73) Assignees: TOKYO METROPOLITAN INSTITUTE OF MEDICAL SCIENCE, Tokyo (JP); ALTIF LABORATORIES INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/026,471

(22) Filed: Sep. 13, 2013

(65) Prior Publication Data

US 2014/0044699 A1 Feb. 13, 2014

Related U.S. Application Data

(62) Division of application No. 12/600,497, filed as application No. PCT/JP2008/059604 on May 19, 2008, now Pat. No. 8,569,032.

(30) Foreign Application Priority Data

May 18, 2007 (JP) ................................. 2007-133536

(51) Int. Cl.
*C12N 9/40* (2006.01)
*A61K 38/47* (2006.01)
*A61K 48/00* (2006.01)

(52) U.S. Cl.
CPC .............. *C12N 9/2465* (2013.01); *A61K 38/47* (2013.01); *A61K 48/005* (2013.01)

(58) Field of Classification Search
CPC ................................ C12N 9/2465; C12N 9/24
See application file for complete search history.

(56) References Cited

U.S. PATENT DOCUMENTS

| 7,579,166 | B2 | 8/2009 | Chiba et al. |
| 2005/0064539 | A1 | 3/2005 | Chiba et al. |
| 2005/0125859 | A1 | 6/2005 | Garger et al. |

FOREIGN PATENT DOCUMENTS

| CA | 2305768 A1 | 2/2000 | | |
| EP | 1961816 A1 | 8/2008 | | |
| JP | 2002522509 T | 7/2002 | | |
| JP | 2002369692 A | 12/2002 | | |
| JP | 2005-333660 | * 12/2006 | ............... | C12N 1/19 |
| WO | 98/11206 | 3/1998 | | |
| WO | 0009153 A1 | 2/2000 | | |
| WO | 2007/058381 A1 | 5/2007 | | |
| WO | WO 2007/058381 | * 5/2007 | ............... | C12N 1/19 |

OTHER PUBLICATIONS

USPTO in house BLAST alignment of SEQ ID No. 6 versus SEQ ID No. 8. Jan. 30, 2015.*
Aikawa et al, Protein which changed the structure of the active site of wild-type-human alpha-N-acetyl galactosaminidase, and acquired galactosidase activity. JP2005-333660 application, publication 2006. USPTO machine translation.*
USPTO in house BLAST alignment SEQ ID No. 4 from Aikawa et al, 2005. Alignment with SEQ ID No. 8.*
Geneseq_201504 database Acc#AGB10277 from Aikawa et al, WO2007058381 SEQ ID No. 3. Alignment with SEQ ID No. 8.*
Schottler et al, Protein engineering of the restriction endonuclease EcoRV—structure-guided design of enzyme variants that recognize the base pairs flanking the recognition site. Eur J Biochem. Nov. 15, 1998;258(1)1 84-91.*
Tsuji et al, Signal sequence and DNA-mediated expression of human lysosomal alpha-galactosidase A. Eur J Biochem. Jun. 1, 1987;165(2):275-80.
PIR_80 database Acc#S04081 from Tsuji et al, Signal sequence and DNA-mediated expression of human lysosomal alpha-galactosidase A. Eur J Biochem. Jun. 1, 1987;165(2):275-80. Alignment with SEQ ID No. 6 Glu202+Leu205.
Wishart et al, A single mutation converts a novel phosphotyrosine binding domain into a dual-specificity phosphatase. J Biol Chem. Nov. 10, 1995;270(45):26782-26785.
Whisstock et al, Prediction of protein function from protein sequence and structure. Q Rev Biophys. Aug. 2003;36(3):307-40. Review.
Garman S.C. et al. The molecular defect leading to Fabry disease: structure of human alphagalactosidase. J. Mol. Biol. vol. 337, No. 2, (2004) p. 319-335.
Garman S.C. et al., The 1.9 A structure of alpha-N-acetylgalactosaminidase: molecular basis of glycosidase deficiency diseases. Structure, vol. 10, No. 3, (2002) p. 425-434.
Garman S.C. et al. Structural basis of Fabry disease.Mol. Genet. Metab., vol. 77, No. 1-2, (2002), p. 3-11.
Schiffmann R. et al. Infusion of alphagalactosidase A reduces tissue globotriaosylceramide storage in patients with Fabry disease. Proc. Natl. Acad. Sci. USA., vol. 97, No. 1, (2000), p. 365-370.
Wang A.M., et al. Structural organization and complete sequence of the human alpha-Nacetyl-galactosaminidase gene: homology with the alpha-galactosidase A gene provides evidence for evolution from a common ancestral gene. Genomics, vol. 10, No. 1, (1991), p. 133-142.

(Continued)

*Primary Examiner* — Sheridan Swope
(74) *Attorney, Agent, or Firm* — McDermott Will & Emery LLP

(57) ABSTRACT

The present invention provides a pharmaceutical composition comprising a protein having α-galactosidase activity for treating Fabry disease, which causes no allergic side effect, which is highly stable in blood (plasma) and which can readily be taken up by a cell of an affected organ. The pharmaceutical composition for treating Fabry disease of the invention comprises, for example, a protein which acquires an α-galactosidase activity through alteration of the structure of the active site of wild-type human α-N-acetylgalactosaminidase.

7 Claims, 14 Drawing Sheets

(56) References Cited

OTHER PUBLICATIONS

Sakuraba H. et al. Structural and immunocyto chemical studies on alpha-Nacetylgalactosaminidase deficiency (Schindler/Kanzaki disease). J. Hum. Genet., vol. 49, No. 1, (2004), p. 1-8.

Yasuda M. et al. Fabry disease: characterization of alpha-galactosidase A double mutations and the D313Y plasma enzyme pseudodeficiency allele. Hum. Mutat., vol. 22, No. 6, (2003), p. 486-492.

Kanekura T. et al. Three dimensional structural studies of alpha-Nacetylgalactosaminidase (alpha-NAGA) in alpha-NAGA deficiency (Kanzaki disease): different gene mutations cause peculiar structural changes in alpha-NAGAs resulting in different substrate specificities and clinical phenotypes. J. Dermatol. Sci., vol. 37, No. 1, (2005), p. 15-20.

Kenneth J Dean et al., "Fabry Disease, Practical Enzymology of the Sphingolipidoses", USA, Aln R. Liss, Inc., 1997, p. 173-216.

Eng CM et al., "A Phase 1/2 Clinical of Enzyme Replacement in Fabry Disease: Pharmacokinetic, Substrate Clearance, and Safety Studies", Am J Hum Genet, 68:711-722 (2001).

Eng CM et al., "Safety and Efficacy of Recombinant Human a—Galactosidase a Replacement Therapy in Fabry's Disease", N Engl J Med, 345:9-16 (2001).

Gotrib, Richard W., et al., The Entire Genomic Sequence and cDNA Expression of Mouse α-Galactosidase A1, Biochemical and Molecular Medicine, vol. 57, No. 2, 1996, pp. 139-148.

* cited by examiner

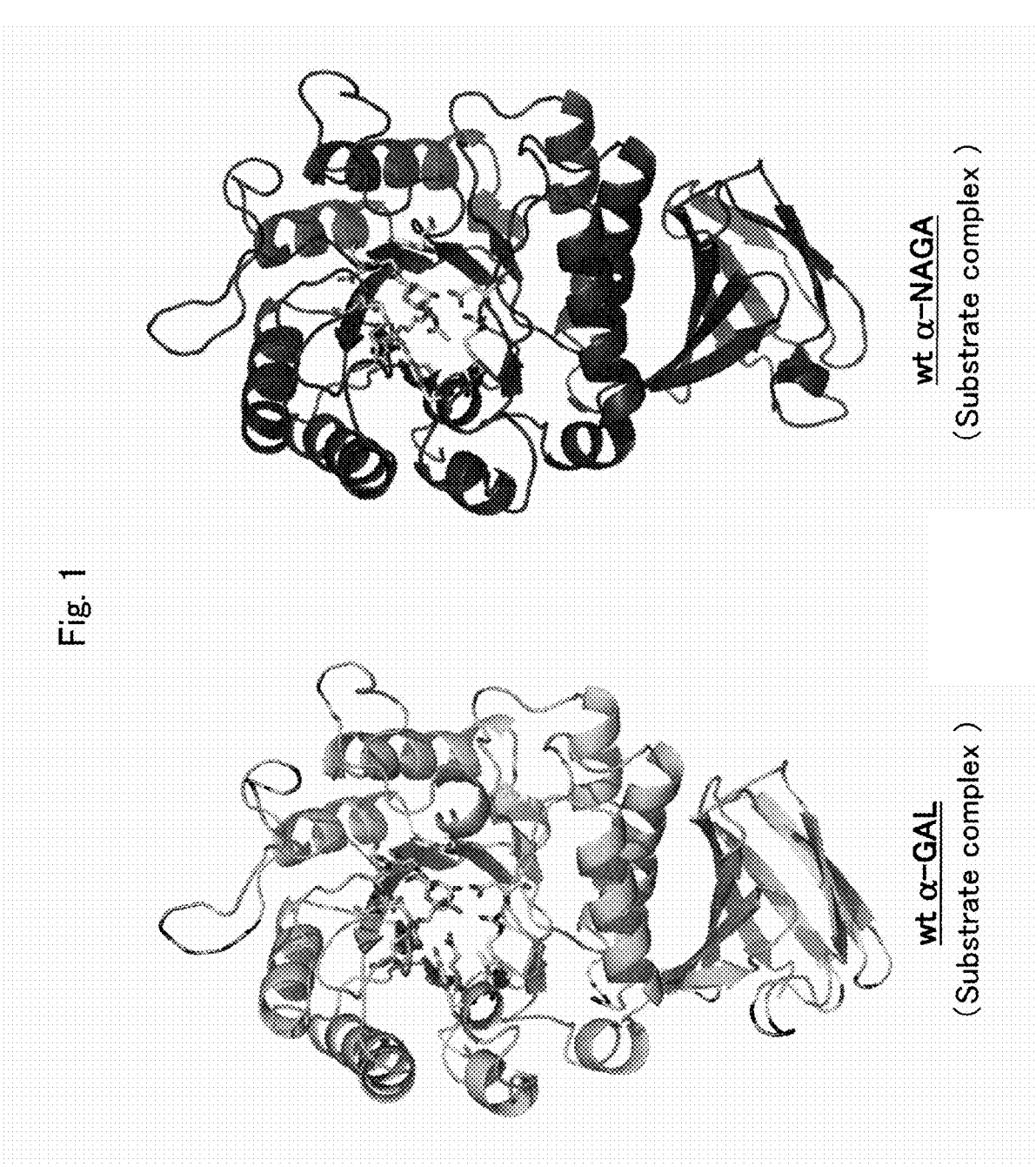

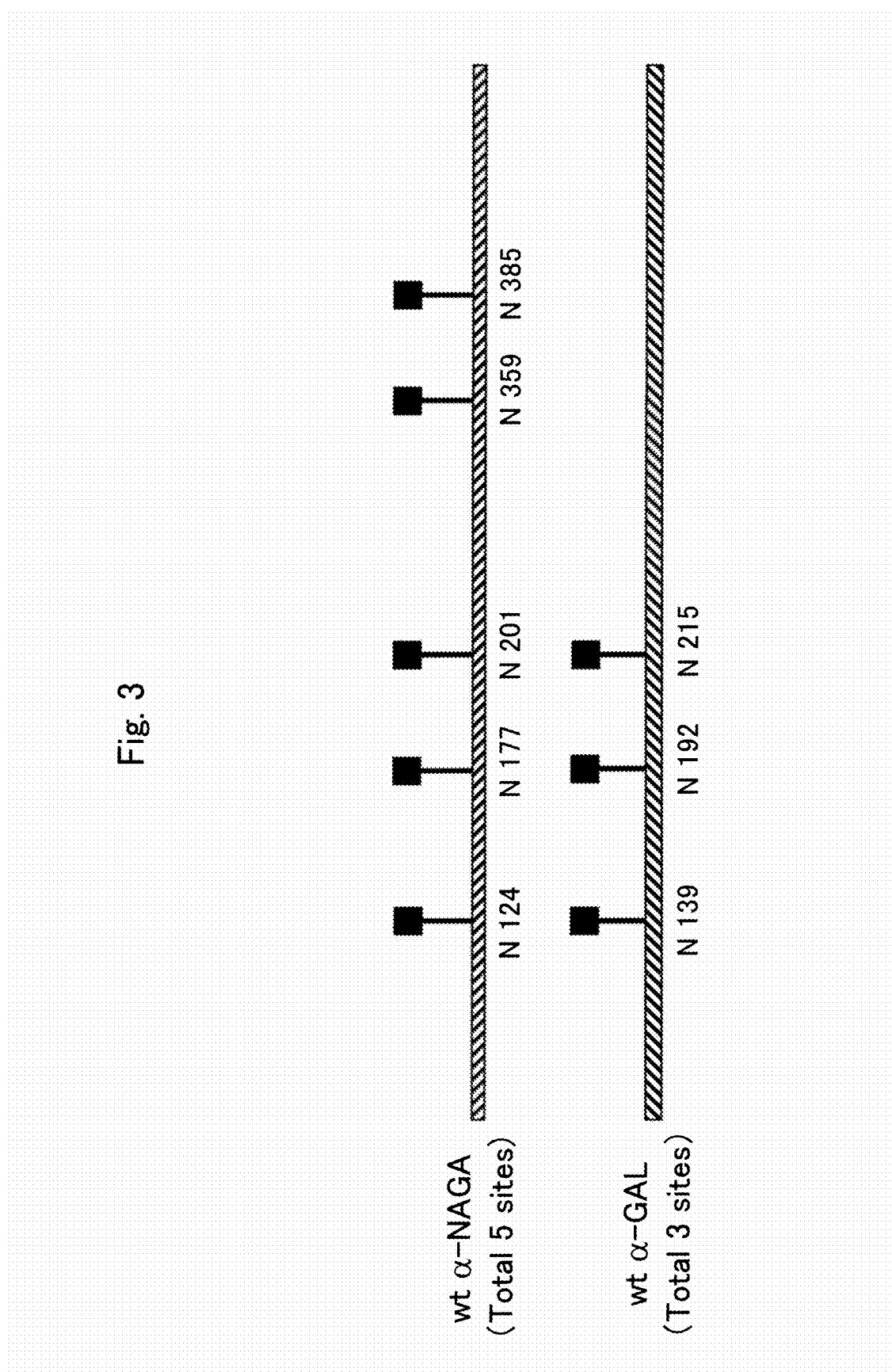

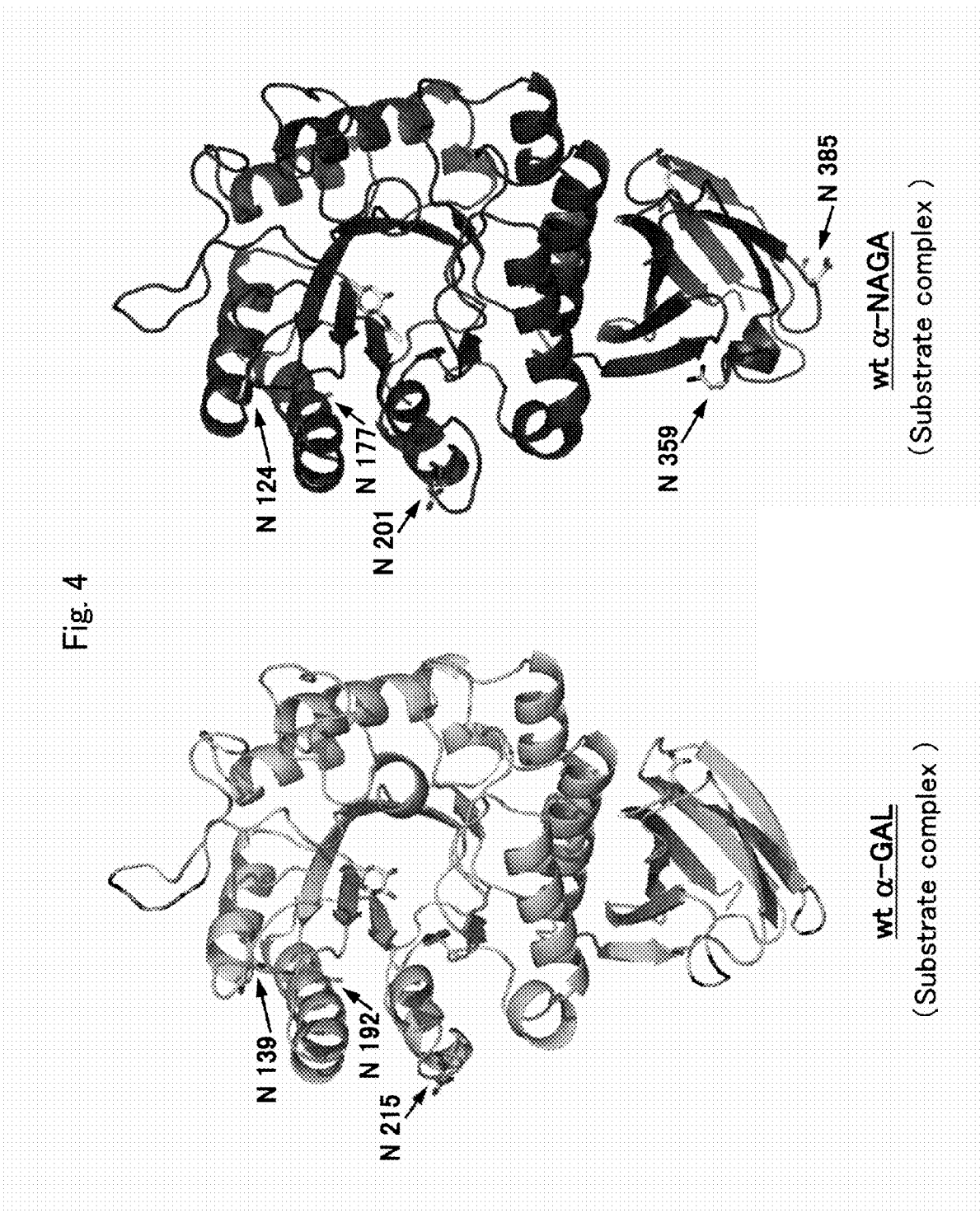

```
                          SEQUENCE LISTING

<160> NUMBER OF SEQ ID NOS: 24

<210> SEQ ID NO 1
<211> LENGTH: 1236
<212> TYPE: DNA
<213> ORGANISM: homo sapiens
<220> FEATURE:
<221> NAME/KEY: CDS
<222> LOCATION: (1)..(1236)

<400> SEQUENCE: 1 atg ctg ctg aag aca gtg ctc ttg ctg gga cat gtg gcc cag gtg ctg      48
Met Leu Leu Lys Thr Val Leu Leu Leu Gly His Val Ala Gln Val Leu
1               5                   10                  15 atg ctg gac aat ggg ctc ctg cag aca cca ccc atg ggc tgg ctg gcc      96
Met Leu Asp Asn Gly Leu Leu Gln Thr Pro Pro Met Gly Trp Leu Ala
            20                  25                  30 tgg gaa cgc ttc cgc tgc aac att aac tgt gat gag gac cca aag aac     144
Trp Glu Arg Phe Arg Cys Asn Ile Asn Cys Asp Glu Asp Pro Lys Asn
        35                  40                  45 tgc ata agt gaa cag ctc ttc atg gag atg gct gac cgg atg gca cag     192
Cys Ile Ser Glu Gln Leu Phe Met Glu Met Ala Asp Arg Met Ala Gln
    50                  55                  60 gat gga tgg cgg gac atg ggc tac aca tac cta aac att gat gac tgc     240
Asp Gly Trp Arg Asp Met Gly Tyr Thr Tyr Leu Asn Ile Asp Asp Cys
65                  70                  75                  80 tgg atc ggc ggt cgc gat gcc agt ggc cgc ctg atg cca gat ccc aag     288
Trp Ile Gly Gly Arg Asp Ala Ser Gly Arg Leu Met Pro Asp Pro Lys
                85                  90                  95 cgc ttc cct cat ggc att cct ttc ctg gct gac tac gtt cac tcc ctg     336
Arg Phe Pro His Gly Ile Pro Phe Leu Ala Asp Tyr Val His Ser Leu
            100                 105                 110 ggc ctg aag ttg ggt atc tac gcg gac atg ggc aac ttc acc tgc atg     384
Gly Leu Lys Leu Gly Ile Tyr Ala Asp Met Gly Asn Phe Thr Cys Met
        115                 120                 125 ggt tac cca ggc acc aca ctg gac aag gtg gtc cag gat gct cag acc     432
Gly Tyr Pro Gly Thr Thr Leu Asp Lys Val Val Gln Asp Ala Gln Thr
    130                 135                 140
```

```
ttc gcc gag tgg aag gta gac atg ctc aag ctg gat ggc tgc ttc tcc    480
Phe Ala Glu Trp Lys Val Asp Met Leu Lys Leu Asp Gly Cys Phe Ser
145                 150                 155                 160 acc ccc gag gag cgg gcc cag ggg tac ccc aag atg gct gct gcc ctg    528
Thr Pro Glu Glu Arg Ala Gln Gly Tyr Pro Lys Met Ala Ala Ala Leu
            165                 170                 175 aat gcc aca ggc cgc ccc atc gcc ttc tcc tgc agc tgg cca gcc tat    576
Asn Ala Thr Gly Arg Pro Ile Ala Phe Ser Cys Ser Trp Pro Ala Tyr
        180                 185                 190 gaa ggc ggc ctc ccc cca agg gtg aac tac agt ctg ctg gcg gac atc    624
Glu Gly Gly Leu Pro Pro Arg Val Asn Tyr Ser Leu Leu Ala Asp Ile
    195                 200                 205 tgc aac ctc tgg cgt aac tat gat gac atc cag gac tcc tgg tgg agc    672
Cys Asn Leu Trp Arg Asn Tyr Asp Asp Ile Gln Asp Ser Trp Trp Ser
210                 215                 220 gtg ctc tcc atc ctg aat tgg ttc gtg gag cac cag gac ata ctg cag    720
Val Leu Ser Ile Leu Asn Trp Phe Val Glu His Gln Asp Ile Leu Gln
225                 230                 235                 240 cca gtg gcc ggc cct ggg cac tgg aat gac cct gac atg ctg ctc att    768
Pro Val Ala Gly Pro Gly His Trp Asn Asp Pro Asp Met Leu Leu Ile
            245                 250                 255 ggg aac ttt ggt ctc agc tta gag caa tcc cgg gcc cag atg gcc ctg    816
Gly Asn Phe Gly Leu Ser Leu Glu Gln Ser Arg Ala Gln Met Ala Leu
        260                 265                 270 tgg acg gtg ctg gca gcc ccc ctc ttg atg tcc aca gac ctg cgt acc    864
Trp Thr Val Leu Ala Ala Pro Leu Leu Met Ser Thr Asp Leu Arg Thr
    275                 280                 285 atc tcc gcc cag aac atg gac att ctg cag aat cca ctc atg atc aaa    912
Ile Ser Ala Gln Asn Met Asp Ile Leu Gln Asn Pro Leu Met Ile Lys
290                 295                 300 atc aac cag gat ccc tta ggc atc cag gga cgc agg att cac aag gaa    960
Ile Asn Gln Asp Pro Leu Gly Ile Gln Gly Arg Arg Ile His Lys Glu
305                 310                 315                 320 aaa tct ctc atc gaa gtg tac atg cgg cct ctg tcc aac aag gct agc   1008
Lys Ser Leu Ile Glu Val Tyr Met Arg Pro Leu Ser Asn Lys Ala Ser
            325                 330                 335 gcc tta gtc ttc ttc agc tgc agg acc gat atg cct tat cgc tac cac   1056
Ala Leu Val Phe Phe Ser Cys Arg Thr Asp Met Pro Tyr Arg Tyr His
        340                 345                 350 tcc tcc ctt ggc cag ctg aac ttc acc ggg tct gtg ata tat gag gcc   1104
Ser Ser Leu Gly Gln Leu Asn Phe Thr Gly Ser Val Ile Tyr Glu Ala
    355                 360                 365 cag gac gtc tac tca ggt gac atc atc agt ggc ctc cga gat gaa acc   1152
Gln Asp Val Tyr Ser Gly Asp Ile Ile Ser Gly Leu Arg Asp Glu Thr
370                 375                 380 aac ttc aca gtg atc atc aac cct tca ggg gta gtg atg tgg tac ctg   1200
Asn Phe Thr Val Ile Ile Asn Pro Ser Gly Val Val Met Trp Tyr Leu
385                 390                 395                 400 tat ccc atc aag aac ctg gag atg tcc cag cag tga                   1236
Tyr Pro Ile Lys Asn Leu Glu Met Ser Gln Gln
            405                 410

<210> SEQ ID NO 2
<211> LENGTH: 411
<212> TYPE: PRT
<213> ORGANISM: homo sapiens

<400> SEQUENCE: 2

Met Leu Leu Lys Thr Val Leu Leu Leu Gly His Val Ala Gln Val Leu
1               5                   10                  15
```

Met Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 3
<211> LENGTH: 1236
<212> TYPE: DNA

```
<213> ORGANISM: Artificial
<220> FEATURE:
<223> OTHER INFORMATION: recombinant DNA
<220> FEATURE:
<221> NAME/KEY: CDS
<222> LOCATION: (1)..(1236)

<400> SEQUENCE: 3 atg ctg ctg aag aca gtg ctc ttg ctg gga cat gtg gcc cag gtg ctg        48
Met Leu Leu Lys Thr Val Leu Leu Leu Gly His Val Ala Gln Val Leu
1               5                   10                  15 atg ctg gac aat ggg ctc ctg cag aca cca ccc atg ggc tgg ctg gcc        96
Met Leu Asp Asn Gly Leu Leu Gln Thr Pro Pro Met Gly Trp Leu Ala
            20                  25                  30 tgg gaa cgc ttc cgc tgc aac att aac tgt gat gag gac cca aag aac       144
Trp Glu Arg Phe Arg Cys Asn Ile Asn Cys Asp Glu Asp Pro Lys Asn
        35                  40                  45 tgc ata agt gaa cag ctc ttc atg gag atg gct gac cgg atg gca cag       192
Cys Ile Ser Glu Gln Leu Phe Met Glu Met Ala Asp Arg Met Ala Gln
    50                  55                  60 gat gga tgg cgg gac atg ggc tac aca tac cta aac att gat gac tgc       240
Asp Gly Trp Arg Asp Met Gly Tyr Thr Tyr Leu Asn Ile Asp Asp Cys
65                  70                  75                  80 tgg atc ggc ggt cgc gat gcc agt ggc cgc ctg atg cca gat ccc aag       288
Trp Ile Gly Gly Arg Asp Ala Ser Gly Arg Leu Met Pro Asp Pro Lys
                85                  90                  95 cgc ttc cct cat ggc att cct ttc ctg gct gac tac gtt cac tcc ctg       336
Arg Phe Pro His Gly Ile Pro Phe Leu Ala Asp Tyr Val His Ser Leu
            100                 105                 110 ggc ctg aag ttg ggt atc tac gcg gac atg ggc aac ttc acc tgc atg       384
Gly Leu Lys Leu Gly Ile Tyr Ala Asp Met Gly Asn Phe Thr Cys Met
        115                 120                 125 ggt tac cca ggc acc aca ctg gac aag gtg gtc cag gat gct cag acc       432
Gly Tyr Pro Gly Thr Thr Leu Asp Lys Val Val Gln Asp Ala Gln Thr
    130                 135                 140 ttc gcc gag tgg aag gta gac atg ctc aag ctg gat ggc tgc ttc tcc       480
Phe Ala Glu Trp Lys Val Asp Met Leu Lys Leu Asp Gly Cys Phe Ser
145                 150                 155                 160 acc ccc gag gag cgg gcc cag ggg tac ccc aag atg gct gct gcc ctg       528
Thr Pro Glu Glu Arg Ala Gln Gly Tyr Pro Lys Met Ala Ala Ala Leu
                165                 170                 175 aat gcc aca ggc cgc ccc atc gcc ttc tcc tgc gag tgg cca ctc tat       576
Asn Ala Thr Gly Arg Pro Ile Ala Phe Ser Cys Glu Trp Pro Leu Tyr
            180                 185                 190 gaa ggc ggc ctc ccc cca agg gtg aac tac agt ctg ctg gcg gac atc       624
Glu Gly Gly Leu Pro Pro Arg Val Asn Tyr Ser Leu Leu Ala Asp Ile
        195                 200                 205 tgc aac ctc tgg cgt aac tat gat gac atc cag gac tcc tgg tgg agc       672
Cys Asn Leu Trp Arg Asn Tyr Asp Asp Ile Gln Asp Ser Trp Trp Ser
    210                 215                 220 gtg ctc tcc atc ctg aat tgg ttc gtg gag cac cag gac ata ctg cag       720
Val Leu Ser Ile Leu Asn Trp Phe Val Glu His Gln Asp Ile Leu Gln
225                 230                 235                 240 cca gtg gcc ggc cct ggg cac tgg aat gac cct gac atg ctg ctc att       768
Pro Val Ala Gly Pro Gly His Trp Asn Asp Pro Asp Met Leu Leu Ile
                245                 250                 255 ggg aac ttt ggt ctc agc tta gag caa tcc cgg gcc cag atg gcc ctg       816
Gly Asn Phe Gly Leu Ser Leu Glu Gln Ser Arg Ala Gln Met Ala Leu
            260                 265                 270 tgg acg gtg ctg gca gcc ccc ctc ttg atg tcc aca gac ctg cgt acc       864
Trp Thr Val Leu Ala Ala Pro Leu Leu Met Ser Thr Asp Leu Arg Thr
```

| | | | | | | | | | | | | | | | | |
|---|---|---|---|---|---|---|---|---|---|---|---|---|---|---|---|---|
| | | 275 | | | | 280 | | | | | 285 | | | | | |
| atc | tcc | gcc | cag | aac | atg | gac | att | ctg | cag | aat | cca | ctc | atg | atc | aaa | 912 |
| Ile | Ser | Ala | Gln | Asn | Met | Asp | Ile | Leu | Gln | Asn | Pro | Leu | Met | Ile | Lys | |
| | 290 | | | | 295 | | | | | 300 | | | | | | |
| atc | aac | cag | gat | ccc | tta | ggc | atc | cag | gga | cgc | agg | att | cac | aag | gaa | 960 |
| Ile | Asn | Gln | Asp | Pro | Leu | Gly | Ile | Gln | Gly | Arg | Arg | Ile | His | Lys | Glu | |
| 305 | | | | 310 | | | | | 315 | | | | | 320 | | |
| aaa | tct | ctc | atc | gaa | gtg | tac | atg | cgg | cct | ctg | tcc | aac | aag | gct | agc | 1008 |
| Lys | Ser | Leu | Ile | Glu | Val | Tyr | Met | Arg | Pro | Leu | Ser | Asn | Lys | Ala | Ser | |
| | | | 325 | | | | | 330 | | | | | 335 | | | |
| gcc | tta | gtc | ttc | ttc | agc | tgc | agg | acc | gat | atg | cct | tat | cgc | tac | cac | 1056 |
| Ala | Leu | Val | Phe | Phe | Ser | Cys | Arg | Thr | Asp | Met | Pro | Tyr | Arg | Tyr | His | |
| | | 340 | | | | | 345 | | | | | 350 | | | | |
| tcc | tcc | ctt | ggc | cag | ctg | aac | ttc | acc | ggg | tct | gtg | ata | tat | gag | gcc | 1104 |
| Ser | Ser | Leu | Gly | Gln | Leu | Asn | Phe | Thr | Gly | Ser | Val | Ile | Tyr | Glu | Ala | |
| | 355 | | | | | 360 | | | | | 365 | | | | | |
| cag | gac | gtc | tac | tca | ggt | gac | atc | atc | agt | ggc | ctc | cga | gat | gaa | acc | 1152 |
| Gln | Asp | Val | Tyr | Ser | Gly | Asp | Ile | Ile | Ser | Gly | Leu | Arg | Asp | Glu | Thr | |
| 370 | | | | | 375 | | | | | 380 | | | | | | |
| aac | ttc | aca | gtg | atc | atc | aac | cct | tca | ggg | gta | gtg | atg | tgg | tac | ctg | 1200 |
| Asn | Phe | Thr | Val | Ile | Ile | Asn | Pro | Ser | Gly | Val | Val | Met | Trp | Tyr | Leu | |
| 385 | | | | | 390 | | | | | 395 | | | | | 400 | |
| tat | ccc | atc | aag | aac | ctg | gag | atg | tcc | cag | cag | tga | | | | | 1236 |
| Tyr | Pro | Ile | Lys | Asn | Leu | Glu | Met | Ser | Gln | Gln | | | | | | |
| | | | 405 | | | | | 410 | | | | | | | | |

<210> SEQ ID NO 4
<211> LENGTH: 411
<212> TYPE: PRT
<213> ORGANISM: Artificial
<220> FEATURE:
<223> OTHER INFORMATION: recombinant protein

<400> SEQUENCE: 4

Met Leu Leu Lys Thr Val Leu Leu Gly His Val Ala Gln Val Leu
1               5                   10                  15

Met Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

```
Glu Gly Gly Leu Pro Pro Arg Val Asn Tyr Ser Leu Leu Ala Asp Ile
            195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
            290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
            355                 360                 365

Gln Asp Val Tyr Ser Gly Asp Ile Ile Ser Gly Leu Arg Asp Glu Thr
            370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 5
<211> LENGTH: 1278
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(1278)

<400> SEQUENCE: 5 atg cag ctg agg aac cca gaa cta cat ctg ggc tgc gcg ctt gcg ctt      48
Met Gln Leu Arg Asn Pro Glu Leu His Leu Gly Cys Ala Leu Ala Leu
1               5                   10                  15 cgc ttc ctg gcc ctc gtt tcc tgg gac atc cct ggg gct aga gca ctg      96
Arg Phe Leu Ala Leu Val Ser Trp Asp Ile Pro Gly Ala Arg Ala Leu
                20                  25                  30 gac aat ggg ctc ctg cag aca cca ccc atg ggc tgg ctg gcc tgg gaa     144
Asp Asn Gly Leu Leu Gln Thr Pro Pro Met Gly Trp Leu Ala Trp Glu
            35                  40                  45 cgc ttc cgc tgc aac att aac tgt gat gag gac cca aag aac tgc ata     192
Arg Phe Arg Cys Asn Ile Asn Cys Asp Glu Asp Pro Lys Asn Cys Ile
        50                  55                  60 agt gaa cag ctc ttc atg gag atg gct gac cgg atg gca cag gat gga     240
Ser Glu Gln Leu Phe Met Glu Met Ala Asp Arg Met Ala Gln Asp Gly
65                  70                  75                  80 tgg cgg gac atg ggc tac aca tac cta aac att gat gac tgc tgg atc     288
Trp Arg Asp Met Gly Tyr Thr Tyr Leu Asn Ile Asp Asp Cys Trp Ile
                85                  90                  95
```

| | | |
|---|---|---|
| ggc ggt cgc gat gcc agt ggc cgc ctg atg cca gat ccc aag cgc ttc<br>Gly Gly Arg Asp Ala Ser Gly Arg Leu Met Pro Asp Pro Lys Arg Phe<br>100 105 110 | | 336 |
| cct cat ggc att cct ttc ctg gct gac tac gtt cac tcc ctg ggc ctg<br>Pro His Gly Ile Pro Phe Leu Ala Asp Tyr Val His Ser Leu Gly Leu<br>115 120 125 | | 384 |
| aag ttg ggt atc tac gcg gac atg ggc aac ttc acc tgc atg ggt tac<br>Lys Leu Gly Ile Tyr Ala Asp Met Gly Asn Phe Thr Cys Met Gly Tyr<br>130 135 140 | | 432 |
| cca ggc acc aca ctg gac aag gtg gtc cag gat gct cag acc ttc gcc<br>Pro Gly Thr Thr Leu Asp Lys Val Val Gln Asp Ala Gln Thr Phe Ala<br>145 150 155 160 | | 480 |
| gag tgg aag gta gac atg ctc aag ctg gat ggc tgc ttc tcc acc ccc<br>Glu Trp Lys Val Asp Met Leu Lys Leu Asp Gly Cys Phe Ser Thr Pro<br>165 170 175 | | 528 |
| gag gag cgg gcc cag ggg tac ccc aag atg gct gct gcc ctg aat gcc<br>Glu Glu Arg Ala Gln Gly Tyr Pro Lys Met Ala Ala Ala Leu Asn Ala<br>180 185 190 | | 576 |
| aca ggc cgc ccc atc gcc ttc tcc tgc agc tgg cca gcc tat gaa ggc<br>Thr Gly Arg Pro Ile Ala Phe Ser Cys Ser Trp Pro Ala Tyr Glu Gly<br>195 200 205 | | 624 |
| ggc ctc ccc cca agg gtg aac tac agt ctg ctg gcg gac atc tgc aac<br>Gly Leu Pro Pro Arg Val Asn Tyr Ser Leu Leu Ala Asp Ile Cys Asn<br>210 215 220 | | 672 |
| ctc tgg cgt aac tat gat gac atc cag gac tcc tgg tgg agc gtg ctc<br>Leu Trp Arg Asn Tyr Asp Asp Ile Gln Asp Ser Trp Trp Ser Val Leu<br>225 230 235 240 | | 720 |
| tcc atc ctg aat tgg ttc gtg gag cac cag gac ata ctg cag cca gtg<br>Ser Ile Leu Asn Trp Phe Val Glu His Gln Asp Ile Leu Gln Pro Val<br>245 250 255 | | 768 |
| gcc ggc cct ggg cac tgg aat gac cct gac atg ctg ctc att ggg aac<br>Ala Gly Pro Gly His Trp Asn Asp Pro Asp Met Leu Leu Ile Gly Asn<br>260 265 270 | | 816 |
| ttt ggt ctc agc tta gag caa tcc cgg gcc cag atg gcc ctg tgg acg<br>Phe Gly Leu Ser Leu Glu Gln Ser Arg Ala Gln Met Ala Leu Trp Thr<br>275 280 285 | | 864 |
| gtg ctg gca gcc ccc ctc ttg atg tcc aca gac ctg cgt acc atc tcc<br>Val Leu Ala Ala Pro Leu Leu Met Ser Thr Asp Leu Arg Thr Ile Ser<br>290 295 300 | | 912 |
| gcc cag aac atg gac att ctg cag aat cca ctc atg atc aaa atc aac<br>Ala Gln Asn Met Asp Ile Leu Gln Asn Pro Leu Met Ile Lys Ile Asn<br>305 310 315 320 | | 960 |
| cag gat ccc tta ggc atc cag gga cgc agg att cac aag gaa aaa tct<br>Gln Asp Pro Leu Gly Ile Gln Gly Arg Arg Ile His Lys Glu Lys Ser<br>325 330 335 | | 1008 |
| ctc atc gaa gtg tac atg cgg cct ctg tcc aac aag gct agc gcc tta<br>Leu Ile Glu Val Tyr Met Arg Pro Leu Ser Asn Lys Ala Ser Ala Leu<br>340 345 350 | | 1056 |
| gtc ttc ttc agc tgc agg acc gat atg cct tat cgc tac cac tcc tcc<br>Val Phe Phe Ser Cys Arg Thr Asp Met Pro Tyr Arg Tyr His Ser Ser<br>355 360 365 | | 1104 |
| ctt ggc cag ctg aac ttc acc ggg tct gtg ata tat gag gcc cag gac<br>Leu Gly Gln Leu Asn Phe Thr Gly Ser Val Ile Tyr Glu Ala Gln Asp<br>370 375 380 | | 1152 |
| gtc tac tca ggt gac atc atc agt ggc ctc cga gat gaa acc aac ttc<br>Val Tyr Ser Gly Asp Ile Ile Ser Gly Leu Arg Asp Glu Thr Asn Phe<br>385 390 395 400 | | 1200 |
| aca gtg atc atc aac cct tca ggg gta gtg atg tgg tac ctg tat ccc<br>Thr Val Ile Ile Asn Pro Ser Gly Val Val Met Trp Tyr Leu Tyr Pro | | 1248 |

```
                        405                 410                 415
atc aag aac ctg gag atg tcc cag cag tga                                1278
Ile Lys Asn Leu Glu Met Ser Gln Gln
                420                 425

<210> SEQ ID NO 6
<211> LENGTH: 425
<212> TYPE: PRT
<213> ORGANISM: Artificial
<220> FEATURE:
<223> OTHER INFORMATION: recombinant protein

<400> SEQUENCE: 6
```

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Leu Gln Thr Pro Pro Met Gly Trp Leu Ala Trp Glu
        35                  40                  45

Arg Phe Arg Cys Asn Ile Asn Cys Asp Glu Asp Pro Lys Asn Cys Ile
    50                  55                  60

Ser Glu Gln Leu Phe Met Glu Met Ala Asp Arg Met Ala Gln Asp Gly
65                  70                  75                  80

Trp Arg Asp Met Gly Tyr Thr Tyr Leu Asn Ile Asp Asp Cys Trp Ile
                85                  90                  95

Gly Gly Arg Asp Ala Ser Gly Arg Leu Met Pro Asp Pro Lys Arg Phe
            100                 105                 110

Pro His Gly Ile Pro Phe Leu Ala Asp Tyr Val His Ser Leu Gly Leu
        115                 120                 125

Lys Leu Gly Ile Tyr Ala Asp Met Gly Asn Phe Thr Cys Met Gly Tyr
130                 135                 140

Pro Gly Thr Thr Leu Asp Lys Val Val Gln Asp Ala Gln Thr Phe Ala
145                 150                 155                 160

Glu Trp Lys Val Asp Met Leu Lys Leu Asp Gly Cys Phe Ser Thr Pro
                165                 170                 175

Glu Glu Arg Ala Gln Gly Tyr Pro Lys Met Ala Ala Ala Leu Asn Ala
            180                 185                 190

Thr Gly Arg Pro Ile Ala Phe Ser Cys Ser Trp Pro Ala Tyr Glu Gly
        195                 200                 205

Gly Leu Pro Pro Arg Val Asn Tyr Ser Leu Leu Ala Asp Ile Cys Asn
210                 215                 220

Leu Trp Arg Asn Tyr Asp Asp Ile Gln Asp Ser Trp Trp Ser Val Leu
225                 230                 235                 240

Ser Ile Leu Asn Trp Phe Val Glu His Gln Asp Ile Leu Gln Pro Val
                245                 250                 255

Ala Gly Pro Gly His Trp Asn Asp Pro Asp Met Leu Leu Ile Gly Asn
            260                 265                 270

Phe Gly Leu Ser Leu Glu Gln Ser Arg Ala Gln Met Ala Leu Trp Thr
        275                 280                 285

Val Leu Ala Ala Pro Leu Leu Met Ser Thr Asp Leu Arg Thr Ile Ser
290                 295                 300

Ala Gln Asn Met Asp Ile Leu Gln Asn Pro Leu Met Ile Lys Ile Asn
305                 310                 315                 320

Gln Asp Pro Leu Gly Ile Gln Gly Arg Arg Ile His Lys Glu Lys Ser
                325                 330                 335

```
Leu Ile Glu Val Tyr Met Arg Pro Leu Ser Asn Lys Ala Ser Ala Leu
                340                 345                 350

Val Phe Phe Ser Cys Arg Thr Asp Met Pro Tyr Arg Tyr His Ser Ser
            355                 360                 365

Leu Gly Gln Leu Asn Phe Thr Gly Ser Val Ile Tyr Glu Ala Gln Asp
        370                 375                 380

Val Tyr Ser Gly Asp Ile Ile Ser Gly Leu Arg Asp Glu Thr Asn Phe
385                 390                 395                 400

Thr Val Ile Ile Asn Pro Ser Gly Val Val Met Trp Tyr Leu Tyr Pro
                405                 410                 415

Ile Lys Asn Leu Glu Met Ser Gln Gln
                420                 425

<210> SEQ ID NO 7
<211> LENGTH: 1278
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(1278)

<400> SEQUENCE: 7 atg cag ctg agg aac cca gaa cta cat ctg ggc tgc gcg ctt gcg ctt      48
Met Gln Leu Arg Asn Pro Glu Leu His Leu Gly Cys Ala Leu Ala Leu
1               5                   10                  15 cgc ttc ctg gcc ctc gtt tcc tgg gac atc cct ggg gct aga gca ctg      96
Arg Phe Leu Ala Leu Val Ser Trp Asp Ile Pro Gly Ala Arg Ala Leu
            20                  25                  30 gac aat ggg ctc ctg cag aca cca ccc atg ggc tgg ctg gcc tgg gaa     144
Asp Asn Gly Leu Leu Gln Thr Pro Pro Met Gly Trp Leu Ala Trp Glu
        35                  40                  45 cgc ttc cgc tgc aac att aac tgt gat gag gac cca aag aac tgc ata     192
Arg Phe Arg Cys Asn Ile Asn Cys Asp Glu Asp Pro Lys Asn Cys Ile
    50                  55                  60 agt gaa cag ctc ttc atg gag atg gct gac cgg atg gca cag gat gga     240
Ser Glu Gln Leu Phe Met Glu Met Ala Asp Arg Met Ala Gln Asp Gly
65                  70                  75                  80 tgg cgg gac atg ggc tac aca tac cta aac att gat gac tgc tgg atc     288
Trp Arg Asp Met Gly Tyr Thr Tyr Leu Asn Ile Asp Asp Cys Trp Ile
                85                  90                  95 ggc ggt cgc gat gcc agt ggc cgc ctg atg cca gat ccc aag cgc ttc     336
Gly Gly Arg Asp Ala Ser Gly Arg Leu Met Pro Asp Pro Lys Arg Phe
            100                 105                 110 cct cat ggc att cct ttc ctg gct gac tac gtt cac tcc ctg ggc ctg     384
Pro His Gly Ile Pro Phe Leu Ala Asp Tyr Val His Ser Leu Gly Leu
        115                 120                 125 aag ttg ggt atc tac gcg gac atg ggc aac ttc acc tgc atg ggt tac     432
Lys Leu Gly Ile Tyr Ala Asp Met Gly Asn Phe Thr Cys Met Gly Tyr
    130                 135                 140 cca ggc acc aca ctg gac aag gtg gtc cag gat gct cag acc ttc gcc     480
Pro Gly Thr Thr Leu Asp Lys Val Val Gln Asp Ala Gln Thr Phe Ala
145                 150                 155                 160 gag tgg aag gta gac atg ctc aag ctg gat ggc tgc ttc tcc acc ccc     528
Glu Trp Lys Val Asp Met Leu Lys Leu Asp Gly Cys Phe Ser Thr Pro
                165                 170                 175 gag gag cgg gcc cag ggg tac ccc aag atg gct gct gcc ctg aat gcc     576
Glu Glu Arg Ala Gln Gly Tyr Pro Lys Met Ala Ala Ala Leu Asn Ala
            180                 185                 190
```

| | | |
|---|---|---|
| aca ggc cgc ccc atc gcc ttc tcc tgc gag tgg cca ctc tat gaa ggc<br>Thr Gly Arg Pro Ile Ala Phe Ser Cys Glu Trp Pro Leu Tyr Glu Gly<br>195　　　　　　　200　　　　　　　205 | | 624 |
| ggc ctc ccc cca agg gtg aac tac agt ctg ctg gcg gac atc tgc aac<br>Gly Leu Pro Pro Arg Val Asn Tyr Ser Leu Leu Ala Asp Ile Cys Asn<br>210　　　　　　　215　　　　　　　220 | | 672 |
| ctc tgg cgt aac tat gat gac atc cag gac tcc tgg tgg agc gtg ctc<br>Leu Trp Arg Asn Tyr Asp Asp Ile Gln Asp Ser Trp Trp Ser Val Leu<br>225　　　　　230　　　　　　　235　　　　　　　240 | | 720 |
| tcc atc ctg aat tgg ttc gtg gag cac cag gac ata ctg cag cca gtg<br>Ser Ile Leu Asn Trp Phe Val Glu His Gln Asp Ile Leu Gln Pro Val<br>245　　　　　　　250　　　　　　　255 | | 768 |
| gcc ggc cct ggg cac tgg aat gac cct gac atg ctg ctc att ggg aac<br>Ala Gly Pro Gly His Trp Asn Asp Pro Asp Met Leu Leu Ile Gly Asn<br>260　　　　　　　265　　　　　　　270 | | 816 |
| ttt ggt ctc agc tta gag caa tcc cgg gcc cag atg gcc ctg tgg acg<br>Phe Gly Leu Ser Leu Glu Gln Ser Arg Ala Gln Met Ala Leu Trp Thr<br>275　　　　　　　280　　　　　　　285 | | 864 |
| gtg ctg gca gcc ccc ctc ttg atg tcc aca gac ctg cgt acc atc tcc<br>Val Leu Ala Ala Pro Leu Leu Met Ser Thr Asp Leu Arg Thr Ile Ser<br>290　　　　　　　295　　　　　　　300 | | 912 |
| gcc cag aac atg gac att ctg cag aat cca ctc atg atc aaa atc aac<br>Ala Gln Asn Met Asp Ile Leu Gln Asn Pro Leu Met Ile Lys Ile Asn<br>305　　　　　　　310　　　　　　　315　　　　　　　320 | | 960 |
| cag gat ccc tta ggc atc cag gga cgc agg att cac aag gaa aaa tct<br>Gln Asp Pro Leu Gly Ile Gln Gly Arg Arg Ile His Lys Glu Lys Ser<br>　　　　　　　325　　　　　　　330　　　　　　　335 | | 1008 |
| ctc atc gaa gtg tac atg cgg cct ctg tcc aac aag gct agc gcc tta<br>Leu Ile Glu Val Tyr Met Arg Pro Leu Ser Asn Lys Ala Ser Ala Leu<br>340　　　　　　　345　　　　　　　350 | | 1056 |
| gtc ttc ttc agc tgc agg acc gat atg cct tat cgc tac cac tcc tcc<br>Val Phe Phe Ser Cys Arg Thr Asp Met Pro Tyr Arg Tyr His Ser Ser<br>355　　　　　　　360　　　　　　　365 | | 1104 |
| ctt ggc cag ctg aac ttc acc ggg tct gtg ata tat gag gcc cag gac<br>Leu Gly Gln Leu Asn Phe Thr Gly Ser Val Ile Tyr Glu Ala Gln Asp<br>370　　　　　　　375　　　　　　　380 | | 1152 |
| gtc tac tca ggt gac atc atc agt ggc ctc cga gat gaa acc aac ttc<br>Val Tyr Ser Gly Asp Ile Ile Ser Gly Leu Arg Asp Glu Thr Asn Phe<br>385　　　　　　　390　　　　　　　395　　　　　　　400 | | 1200 |
| aca gtg atc atc aac cct tca ggg gta gtg atg tgg tac ctg tat ccc<br>Thr Val Ile Ile Asn Pro Ser Gly Val Val Met Trp Tyr Leu Tyr Pro<br>　　　　　　　405　　　　　　　410　　　　　　　415 | | 1248 |
| atc aag aac ctg gag atg tcc cag cag tga<br>Ile Lys Asn Leu Glu Met Ser Gln Gln<br>420　　　　　　　425 | | 1278 |

<210> SEQ ID NO 8
<211> LENGTH: 425
<212> TYPE: PRT
<213> ORGANISM: Artificial
<220> FEATURE:
<223> OTHER INFORMATION: recombinant protein

<400> SEQUENCE: 8

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Leu Gln Thr Pro Pro Met Gly Trp Leu Ala Trp Glu
            35                  40                  45

Arg Phe Arg Cys Asn Ile Asn Cys Asp Glu Asp Pro Lys Asn Cys Ile
        50                  55                  60

Ser Glu Gln Leu Phe Met Glu Met Ala Asp Arg Met Ala Gln Asp Gly
 65                  70                  75                  80

Trp Arg Asp Met Gly Tyr Thr Tyr Leu Asn Ile Asp Asp Cys Trp Ile
                 85                  90                  95

Gly Gly Arg Asp Ala Ser Gly Arg Leu Met Pro Asp Pro Lys Arg Phe
                100                 105                 110

Pro His Gly Ile Pro Phe Leu Ala Asp Tyr Val His Ser Leu Gly Leu
            115                 120                 125

Lys Leu Gly Ile Tyr Ala Asp Met Gly Asn Phe Thr Cys Met Gly Tyr
        130                 135                 140

Pro Gly Thr Thr Leu Asp Lys Val Val Gln Asp Ala Gln Thr Phe Ala
145                 150                 155                 160

Glu Trp Lys Val Asp Met Leu Lys Leu Asp Gly Cys Phe Ser Thr Pro
                165                 170                 175

Glu Glu Arg Ala Gln Gly Tyr Pro Lys Met Ala Ala Ala Leu Asn Ala
            180                 185                 190

Thr Gly Arg Pro Ile Ala Phe Ser Cys Glu Trp Pro Leu Tyr Glu Gly
        195                 200                 205

Gly Leu Pro Pro Arg Val Asn Tyr Ser Leu Leu Ala Asp Ile Cys Asn
    210                 215                 220

Leu Trp Arg Asn Tyr Asp Asp Ile Gln Asp Ser Trp Trp Ser Val Leu
225                 230                 235                 240

Ser Ile Leu Asn Trp Phe Val Glu His Gln Asp Ile Leu Gln Pro Val
                245                 250                 255

Ala Gly Pro Gly His Trp Asn Asp Pro Asp Met Leu Leu Ile Gly Asn
            260                 265                 270

Phe Gly Leu Ser Leu Glu Gln Ser Arg Ala Gln Met Ala Leu Trp Thr
        275                 280                 285

Val Leu Ala Ala Pro Leu Leu Met Ser Thr Asp Leu Arg Thr Ile Ser
    290                 295                 300

Ala Gln Asn Met Asp Ile Leu Gln Asn Pro Leu Met Ile Lys Ile Asn
305                 310                 315                 320

Gln Asp Pro Leu Gly Ile Gln Gly Arg Ile His Lys Glu Lys Ser
                325                 330                 335

Leu Ile Glu Val Tyr Met Arg Pro Leu Ser Asn Lys Ala Ser Ala Leu
            340                 345                 350

Val Phe Phe Ser Cys Arg Thr Asp Met Pro Tyr Arg Tyr His Ser Ser
        355                 360                 365

Leu Gly Gln Leu Asn Phe Thr Gly Ser Val Ile Tyr Glu Ala Gln Asp
    370                 375                 380

Val Tyr Ser Gly Asp Ile Ile Ser Gly Leu Arg Asp Glu Thr Asn Phe
385                 390                 395                 400

Thr Val Ile Ile Asn Pro Ser Gly Val Val Met Trp Tyr Leu Tyr Pro
                405                 410                 415

Ile Lys Asn Leu Glu Met Ser Gln Gln
            420                 425

<210> SEQ ID NO 9
<211> LENGTH: 1290
<212> TYPE: DNA
<213> ORGANISM: homo sapiens
<220> FEATURE:
<221> NAME/KEY: CDS

<222> LOCATION: (1)..(1290)

<400> SEQUENCE: 9

| | | | | | | | | | | | | | | | | |
|---|---|---|---|---|---|---|---|---|---|---|---|---|---|---|---|---|
| atg | cag | ctg | agg | aac | cca | gaa | cta | cat | ctg | ggc | tgc | gcg | ctt | gcg | ctt | 48 |
| Met | Gln | Leu | Arg | Asn | Pro | Glu | Leu | His | Leu | Gly | Cys | Ala | Leu | Ala | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgc | ttc | ctg | gcc | ctc | gtt | tcc | tgg | gac | atc | cct | ggg | gct | aga | gca | ctg | 96 |
| Arg | Phe | Leu | Ala | Leu | Val | Ser | Trp | Asp | Ile | Pro | Gly | Ala | Arg | Ala | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | aat | gga | ttg | gca | agg | acg | cct | acc | atg | ggc | tgg | ctg | cac | tgg | gag | 144 |
| Asp | Asn | Gly | Leu | Ala | Arg | Thr | Pro | Thr | Met | Gly | Trp | Leu | His | Trp | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| cgc | ttc | atg | tgc | aac | ctt | gac | tgc | cag | gaa | gag | cca | gat | tcc | tgc | atc | 192 |
| Arg | Phe | Met | Cys | Asn | Leu | Asp | Cys | Gln | Glu | Glu | Pro | Asp | Ser | Cys | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| agt | gag | aag | ctc | ttc | atg | gag | atg | gca | gag | ctc | atg | gtc | tca | gaa | ggc | 240 |
| Ser | Glu | Lys | Leu | Phe | Met | Glu | Met | Ala | Glu | Leu | Met | Val | Ser | Glu | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tgg | aag | gat | gca | ggt | tat | gag | tac | ctc | tgc | att | gat | gac | tgt | tgg | atg | 288 |
| Trp | Lys | Asp | Ala | Gly | Tyr | Glu | Tyr | Leu | Cys | Ile | Asp | Asp | Cys | Trp | Met | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | ccc | caa | aga | gat | tca | gaa | ggc | aga | ctt | cag | gca | gac | cct | cag | cgc | 336 |
| Ala | Pro | Gln | Arg | Asp | Ser | Glu | Gly | Arg | Leu | Gln | Ala | Asp | Pro | Gln | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| ttt | cct | cat | ggg | att | cgc | cag | cta | gct | aat | tat | gtt | cac | agc | aaa | gga | 384 |
| Phe | Pro | His | Gly | Ile | Arg | Gln | Leu | Ala | Asn | Tyr | Val | His | Ser | Lys | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| ctg | aag | cta | ggg | att | tat | gca | gat | gtt | gga | aat | aaa | acc | tgc | gca | ggc | 432 |
| Leu | Lys | Leu | Gly | Ile | Tyr | Ala | Asp | Val | Gly | Asn | Lys | Thr | Cys | Ala | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| ttc | cct | ggg | agt | ttt | gga | tac | tac | gac | att | gat | gcc | cag | acc | ttt | gct | 480 |
| Phe | Pro | Gly | Ser | Phe | Gly | Tyr | Tyr | Asp | Ile | Asp | Ala | Gln | Thr | Phe | Ala | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gac | tgg | gga | gta | gat | ctg | cta | aaa | ttt | gat | ggt | tgt | tac | tgt | gac | agt | 528 |
| Asp | Trp | Gly | Val | Asp | Leu | Leu | Lys | Phe | Asp | Gly | Cys | Tyr | Cys | Asp | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| ttg | gaa | aat | ttg | gca | gat | ggt | tat | aag | cac | atg | tcc | ttg | gcc | ctg | aat | 576 |
| Leu | Glu | Asn | Leu | Ala | Asp | Gly | Tyr | Lys | His | Met | Ser | Leu | Ala | Leu | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| agg | act | ggc | aga | agc | att | gtg | tac | tcc | tgt | gag | tgg | cct | ctt | tat | atg | 624 |
| Arg | Thr | Gly | Arg | Ser | Ile | Val | Tyr | Ser | Cys | Glu | Trp | Pro | Leu | Tyr | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| tgg | ccc | ttt | caa | aag | ccc | aat | tat | aca | gaa | atc | cga | cag | tac | tgc | aat | 672 |
| Trp | Pro | Phe | Gln | Lys | Pro | Asn | Tyr | Thr | Glu | Ile | Arg | Gln | Tyr | Cys | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| cac | tgg | cga | aat | ttt | gct | gac | att | gat | gat | tcc | tgg | aaa | agt | ata | aag | 720 |
| His | Trp | Arg | Asn | Phe | Ala | Asp | Ile | Asp | Asp | Ser | Trp | Lys | Ser | Ile | Lys | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| agt | atc | ttg | gac | tgg | aca | tct | ttt | aac | cag | gag | aga | att | gtt | gat | gtt | 768 |
| Ser | Ile | Leu | Asp | Trp | Thr | Ser | Phe | Asn | Gln | Glu | Arg | Ile | Val | Asp | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| gct | gga | cca | ggg | ggt | tgg | aat | gac | cca | gat | atg | tta | gtg | att | ggc | aac | 816 |
| Ala | Gly | Pro | Gly | Gly | Trp | Asn | Asp | Pro | Asp | Met | Leu | Val | Ile | Gly | Asn | |
| | | | 260 | | | | | 265 | | | | | 270 | | | |

| | | | | | | | | | | | | | | | | |
|---|---|---|---|---|---|---|---|---|---|---|---|---|---|---|---|---|
| ttt | ggc | ctc | agc | tgg | aat | cag | caa | gta | act | cag | atg | gcc | ctc | tgg | gct | 864 |
| Phe | Gly | Leu | Ser | Trp | Asn | Gln | Gln | Val | Thr | Gln | Met | Ala | Leu | Trp | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| atc | atg | gct | gct | cct | tta | ttc | atg | tct | aat | gac | ctc | cga | cac | atc | agc | 912 |
| Ile | Met | Ala | Ala | Pro | Leu | Phe | Met | Ser | Asn | Asp | Leu | Arg | His | Ile | Ser | |
| | 290 | | | | | 295 | | | | | 300 | | | | | |

```
cct caa gcc aaa gct ctc ctt cag gat aag gac gta att gcc atc aat    960
Pro Gln Ala Lys Ala Leu Leu Gln Asp Lys Asp Val Ile Ala Ile Asn
305                 310                 315                 320 cag gac ccc ttg ggc aag caa ggg tac cag ctt aga cag gga gac aac   1008
Gln Asp Pro Leu Gly Lys Gln Gly Tyr Gln Leu Arg Gln Gly Asp Asn
            325                 330                 335 ttt gaa gtg tgg gaa cga cct ctc tca ggc tta gcc tgg gct gta gct   1056
Phe Glu Val Trp Glu Arg Pro Leu Ser Gly Leu Ala Trp Ala Val Ala
        340                 345                 350 atg ata aac cgg cag gag att ggt gga cct cgc tct tat acc atc gca   1104
Met Ile Asn Arg Gln Glu Ile Gly Gly Pro Arg Ser Tyr Thr Ile Ala
    355                 360                 365 gtt gct tcc ctg ggt aaa gga gtg gcc tgt aat cct gcc tgc ttc atc   1152
Val Ala Ser Leu Gly Lys Gly Val Ala Cys Asn Pro Ala Cys Phe Ile
370                 375                 380 aca cag ctc ctc cct gtg aaa agg aag cta ggg ttc tat gaa tgg act   1200
Thr Gln Leu Leu Pro Val Lys Arg Lys Leu Gly Phe Tyr Glu Trp Thr
385                 390                 395                 400 tca agg tta aga agt cac ata aat ccc aca ggc act gtt ttg ctt cag   1248
Ser Arg Leu Arg Ser His Ile Asn Pro Thr Gly Thr Val Leu Leu Gln
            405                 410                 415 cta gaa aat aca atg cag atg tca tta aaa gac tta ctt taa           1290
Leu Glu Asn Thr Met Gln Met Ser Leu Lys Asp Leu Leu
        420                 425

<210> SEQ ID NO 10
<211> LENGTH: 429
<212> TYPE: PRT
<213> ORGANISM: homo sapiens

<400> SEQUENCE: 10

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205
```

-continued

```
Trp Pro Phe Gln Lys Pro Asn Tyr Thr Glu Ile Arg Gln Tyr Cys Asn
    210                 215                 220
His Trp Arg Asn Phe Ala Asp Ile Asp Asp Ser Trp Lys Ser Ile Lys
225                 230                 235                 240
Ser Ile Leu Asp Trp Thr Ser Phe Asn Gln Glu Arg Ile Val Asp Val
                245                 250                 255
Ala Gly Pro Gly Gly Trp Asn Asp Pro Asp Met Leu Val Ile Gly Asn
            260                 265                 270
Phe Gly Leu Ser Trp Asn Gln Gln Val Thr Gln Met Ala Leu Trp Ala
        275                 280                 285
Ile Met Ala Ala Pro Leu Phe Met Ser Asn Asp Leu Arg His Ile Ser
    290                 295                 300
Pro Gln Ala Lys Ala Leu Leu Gln Asp Lys Asp Val Ile Ala Ile Asn
305                 310                 315                 320
Gln Asp Pro Leu Gly Lys Gln Gly Tyr Gln Leu Arg Gln Gly Asp Asn
                325                 330                 335
Phe Glu Val Trp Glu Arg Pro Leu Ser Gly Leu Ala Trp Ala Val Ala
            340                 345                 350
Met Ile Asn Arg Gln Glu Ile Gly Gly Pro Arg Ser Tyr Thr Ile Ala
        355                 360                 365
Val Ala Ser Leu Gly Lys Gly Val Ala Cys Asn Pro Ala Cys Phe Ile
    370                 375                 380
Thr Gln Leu Leu Pro Val Lys Arg Lys Leu Gly Phe Tyr Glu Trp Thr
385                 390                 395                 400
Ser Arg Leu Arg Ser His Ile Asn Pro Thr Gly Thr Val Leu Leu Gln
                405                 410                 415
Leu Glu Asn Thr Met Gln Met Ser Leu Lys Asp Leu Leu
            420                 425
```

<210> SEQ ID NO 11
<211> LENGTH: 45
<212> TYPE: DNA
<213> ORGANISM: homo sapiens
<220> FEATURE:
<221> NAME/KEY: CDS
<222> LOCATION: (1)..(45)

<400> SEQUENCE: 11

```
atg tct gca ctt ctg atc cta gct ctt gtt gga gct gca gtt gct     45
Met Ser Ala Leu Leu Ile Leu Ala Leu Val Gly Ala Ala Val Ala
1               5                   10                  15
```

<210> SEQ ID NO 12
<211> LENGTH: 15
<212> TYPE: PRT
<213> ORGANISM: homo sapiens

<400> SEQUENCE: 12

```
Met Ser Ala Leu Leu Ile Leu Ala Leu Val Gly Ala Ala Val Ala
1               5                   10                  15
```

<210> SEQ ID NO 13
<211> LENGTH: 24
<212> TYPE: DNA
<213> ORGANISM: Artificial
<220> FEATURE:
<223> OTHER INFORMATION: synthetic DNA

<400> SEQUENCE: 13
gatgctgctg aagacagtgc tctt                                              24

<210> SEQ ID NO 14
<211> LENGTH: 24
<212> TYPE: DNA
<213> ORGANISM: Artificial
<220> FEATURE:
<223> OTHER INFORMATION: synthetic DNA

<400> SEQUENCE: 14
tcactgctgg gacatctcca ggtt                                              24

<210> SEQ ID NO 15
<211> LENGTH: 21
<212> TYPE: DNA
<213> ORGANISM: Artificial
<220> FEATURE:
<223> OTHER INFORMATION: synthetic DNA

<400> SEQUENCE: 15
aaaccgttgc tagcttaagt t                                                 21

<210> SEQ ID NO 16
<211> LENGTH: 35
<212> TYPE: DNA
<213> ORGANISM: Artificial
<220> FEATURE:
<223> OTHER INFORMATION: synthetic DNA

<400> SEQUENCE: 16
cccatcgcct tctcctgcga gtggccagcc tatga                                  35

<210> SEQ ID NO 17
<211> LENGTH: 28
<212> TYPE: DNA
<213> ORGANISM: Artificial
<220> FEATURE:
<223> OTHER INFORMATION: synthetic DNA

<400> SEQUENCE: 17
gcaggagaag gcgatggggc ggcctgtg                                          28

<210> SEQ ID NO 18
<211> LENGTH: 35
<212> TYPE: DNA
<213> ORGANISM: Artificial
<220> FEATURE:
<223> OTHER INFORMATION: synthetic DNA

<400> SEQUENCE: 18
ttctcctgcg agtggccact ctatgaaggc ggcct                                  35

<210> SEQ ID NO 19
<211> LENGTH: 28
<212> TYPE: DNA
<213> ORGANISM: Artificial
<220> FEATURE:
<223> OTHER INFORMATION: synthetic DNA

<400> SEQUENCE: 19
tggccactcg caggagaagg cgatgggg                                          28

<210> SEQ ID NO 20
<211> LENGTH: 24
<212> TYPE: DNA
<213> ORGANISM: Artificial

```
<220> FEATURE:
<223> OTHER INFORMATION: synthetic DNA

<400> SEQUENCE: 20
acaatgcagc tgaggaaccc agaa                                              24

<210> SEQ ID NO 21
<211> LENGTH: 20
<212> TYPE: DNA
<213> ORGANISM: Artificial
<220> FEATURE:
<223> OTHER INFORMATION: synthetic DNA

<400> SEQUENCE: 21
gtccagtgct ctagccccag                                                   20

<210> SEQ ID NO 22
<211> LENGTH: 20
<212> TYPE: DNA
<213> ORGANISM: Artificial
<220> FEATURE:
<223> OTHER INFORMATION: synthetic DNA

<400> SEQUENCE: 22
agagcactgg acaatgggct                                                   20

<210> SEQ ID NO 23
<211> LENGTH: 24
<212> TYPE: DNA
<213> ORGANISM: Artificial
<220> FEATURE:
<223> OTHER INFORMATION: synthetic DNA

<400> SEQUENCE: 23
tcactgctgg gacatctcca ggtt                                              24

<210> SEQ ID NO 24
<211> LENGTH: 21
<212> TYPE: DNA
<213> ORGANISM: Artificial
<220> FEATURE:
<223> OTHER INFORMATION: synthetic DNA

<400> SEQUENCE: 24
gggtggacca tcctctagac t                                                 21
```

POLYNUCLEOTIDES ENCODING PROTEINS HAVING ACQUIRED α-GALACTOSIDASE ACTIVITY

CROSS-REFERENCE TO PRIOR APPLICATIONS

This is a divisional application of U.S. patent application Ser. No. 12/600,497 filed Jul. 27, 2010, which is a U.S. National Phase Application under 35 U.S.C. §371 of International Patent Application No. PCT/JP2008/059604 filed May 19, 2008, which claims the benefit of priority to Japanese Patent Application No. 2007-133536 filed May 18, 2007, all of which are incorporated by reference herein. The International Application was published in Japanese on Nov. 27, 2008 as WO 2008/143354 A1 under PCT Article 21(2).

TECHNICAL FIELD

The present invention relates to a pharmaceutical composition for enzyme replacement therapy, specifically a pharmaceutical composition for treating Fabry disease. In addition, the present invention relates to a novel highly functional enzyme with an altered substrate specificity, specifically a recombinant protein having α-galactosidase activity, which may be used for the pharmaceutical composition.

BACKGROUND ART

For hereditary enzyme deficiency, for which no radical treatments have been known to date, enzyme replacement therapy in which an enzyme is produced by genetic engineering and then administered to the blood vessel by intravenous drip or the like has been gradually developed. As an example of hereditary enzyme deficiency whose prevalence is relatively high and which is designated as a specified disease (intractable disease), Fabry disease (hereditary α-galactosidase deficiency, also called lysosomal disease, which is one of the genetic diseases), is well known (see Kenneth J. Dean et al., Fabry Disease, "Practical Enzymology of the Sphingolipidoses", U.S.A., Aln R. Liss, Inc., 1997, p. 173-216).

Fabry disease is a glycolipid metabolic disorder which develops as follows: As a result of a decrease in the activity or deficiency of an enzyme called "α-galactosidase" present in a lysosome, one of the human intracellular organelles, a glycolipid called globotriaosylceramide (GL-3; also referred to as ceramide trihexoside (CTH)), which is an in vivo substrate of the enzyme, is not degraded and thus accumulated within the body (for example, the blood vessels, skins, cornea, nerves, kidneys, and heart).

Since a gene encoding α-galactosidase lies on the X chromosome, this disease has an X-chromosomal mode inheritance. Therefore, in this disease, a definite clinical feature is displayed mainly in hemizygous males. It is believed that "classic Fabry disease", which takes a typical clinical course, develops in about one out of 40,000 male children. Symptoms such as pain in the hand and the foot, hypohidrosis, angiokeratoma, and corneal opacity appear during the childhood and adolescence; these symptoms progress and then cause systemic organ damage such as renal failure, heart failure, and cerebrovascular disorder in middle age or later, which become a cause of death. There is also "variant Fabry disease", which does not take such a typical clinical course as "classic Fabry disease" and which develops late and takes a relatively moderate course. In patients with this type of disease, remaining α-galactosidase activity is observed though it is low. As a variant Fabry disease, for example, "cardiac Fabry disease" is known, which causes the above-mentioned glycolipid accumulation mainly in the heart. Consequently, cardiac hypertrophy occurs, and disorders such as heart failure and arrhythmia are caused. On the other hand, in heterozygous female Fabry disease patients, various types of clinical features are observed in accordance with the characteristics of the X chromosome. Specifically, cases range from serious cases which are similar to those of hemizygous males to cases in which substantially no symptoms are observed. However, according to recent research, it has become clear that most heterozygous female Fabry disease patients develop some sort of symptoms with age. There is a viewpoint that they should not be regarded as "carriers" but as "patients".

Recently, enzyme replacement therapy has been established for Fabry disease as well, and a recombinant human α-galactosidase produced in a cell derived from mammals has been used widely as an active element of a Fabry disease therapeutic agent in the above therapy (see Eng C M et al., Am J Hum Genet, 68: 711-722 (2001); Eng C M et al., N Engl J Med, 345: 9-16 (2001); and Schiffmann R et al., Proc Natl Acad Sci USA, 97: 365-370 (2000)).

There have also been proposed a method in which a recombinant human α-galactosidase produced with a non-animal cell (for example, yeast) as a host may be used for the treatment of Fabry disease (enzyme replacement therapy) (see Japanese Unexamined Patent Application Publication No. 2002-369692), a gene therapeutic method in which an enzyme is replaced by introducing a gene encoding human α-galactosidase into a cell of an affected tissue to express the gene (see Japanese Unexamined Patent Application Publication (Translation of PCT Application) No. 2002-522509), and the like.

DISCLOSURE OF INVENTION

However, since an existing enzyme agent used for enzyme replacement for treating Fabry disease is often administered to patients who have no enzyme (human α-galactosidase) from the beginning, the enzyme contained in the therapeutic agent is recognized as a foreign substance in many patients administered with the enzyme agent, and an antibody is produced, resulting in a problem of adverse side effects at a high frequency, mainly, allergic reactions. Such a problem similarly occurs in the case where the enzyme is replaced using a gene therapeutic procedure.

In addition, such an enzyme agent used for enzyme replacement is administered in the blood vessels, but α-galactosidase itself is unstable in blood. Accordingly, in the actual therapy, the enzyme agent must be administered frequently (once every two weeks), and it may be necessary to increase the dosage per administration. Furthermore, human α-galactosidase (α-GAL) has a relatively small number of sugar chains (N-type sugar chains) to which mannose-6-phosphate (M6P) residue can bind for uptake by a cell (more specifically, by a lysosome in a cell) of an affected organ. Therefore, uptake of α-GAL by a cell via blood is difficult. In particular, the uptake efficiencies in the kidney or heart, organs predominantly affected by Fabry disease, are low, and thus the therapeutic effect for nephropathy or cardiopathy is hardly sufficient. Accordingly, in order to allow a certain amount of enzyme to be taken up by a target cell upon therapy, a large amount of enzyme is required. Consequently, it is necessary to administer an enzyme agent for enzyme replacement more frequently and in a larger amount. Such therapy places a large burden on patients physically, mentally and economically, and thus adversely affects the "quality of life (QOL)".

Accordingly, it is an object of the present invention to provide, a pharmaceutical composition for treating Fabry disease, which uses a protein having α-GAL activity, which shows no allergic side effect, which is highly stable in blood (in plasma), and can easily be taken up by a cell of an affected organ. It is also an object of the present invention to provide a novel highly functional enzyme with an altered substrate specificity, like the above-mentioned protein having α-GAL activity.

The present inventors conducted intensive studies in order to solve the above problems. As a result, the present inventors focused on "α-N-acetylgalactosaminidase (α-NAGA)", a protein having a substrate specificity different from that of α-GAL but which has overall structure very similar to that of α-GAL. The present inventors have thought that the above problem may be solved if a novel highly functional enzyme (an α-NAGA mutant), obtained by altering the substrate specificity of α-NAGA via alteration of the structure of the active site of α-NAGA to acquire α-GAL activity, is used as an active element of a pharmaceutical composition for treating Fabry disease that can be used for enzyme replacement therapy.

The following facts, however, are generally known in the art.

1) When a part of amino acids of a protein is substituted by a different amino acid, the state of mutual action (hydrogen bonding, hydrophobic bonding, etc.) between said amino acid and the amino acids flanking said amino acid may possibly alter. When the state of mutual action is altered, the three-dimensional structure of the protein having partially-substituted amino acids may change which may impair the primary function of the protein (specifically, an enzymatic activity in the case of an enzyme).

2) The above-mentioned alteration of structure due to partial substitution of the amino acids of the protein may lead to alteration of the surface structure of the protein. When a protein with an altered surface structure is administered to a living organism, the living organism would recognize that protein to be different from the original protein (i.e., foreign to the organism), thereby provoking immune response. When the protein is used as a pharmaceutical agent for administration to a living organism, such an immune response not only deteriorates the function of the protein but may also induce anaphylaxis, which could be a serious life-threatening problem.

Hence, a protein administered to a living organism as a pharmaceutical agent needs to be designed such that not only its function (activity) is retained but also no immune response is caused after the administration.

For the above reasons, even when an amino acid at the active site of α-NAGA, which resembles α-GAL, is substituted by a similar amino acid to one at the active site of α-GAL, preparation of a protein (α-NAGA mutant) having the α-GAL activity and the structure of α-NAGA is not always guaranteed, depending on the position and the type of the substituted amino acid.

In order to solve this problem, the present inventors identified an amino acid sequence of an α-NAGA mutant as a candidate agent for treating Fabry disease by performing simulation through a structural analysis by homology modeling so as to examine the specific aspect of amino acid substitution that allows retention of the α-NAGA surface structure and acquirement of the α-GAL activity at the same time. On that basis, the present inventors actually expressed this α-NAGA mutant to confirm that it has an activity of degrading α-GAL substrate. In addition, this α-NAGA mutant was administered to Fabry disease model mice to confirm that α-GAL activity was indeed distributed in the affected tissue.

From these studies, this α-NAGA mutant was found, for the first time, to be effective as a pharmaceutical agent for treating Fabry disease.

Thus, the present invention relates to the followings.

(1) A pharmaceutical composition for treating Fabry disease, comprising a protein which has acquired α-galactosidase activity by altering the structure of the active site of wild-type human α-N-acetylgalactosaminidase.

An example of the pharmaceutical composition of the invention includes the above-mentioned protein having the substrate specificity of α-galactosidase.

(2) A pharmaceutical composition for treating Fabry disease, comprising a protein of (a) or (b) below:

(a) a protein comprising an amino acid sequence of any one of (i) to (iii) below:

(i) an amino acid sequence comprising the amino acids 18-411 of the amino acid sequence represented by SEQ ID NO:2 where the amino acid 188 is substituted by an amino acid other than serine;

(ii) an amino acid sequence comprising the amino acids 18-411 of the amino acid sequence represented by SEQ ID NO:2 where the amino acid 191 is substituted by an amino acid other than alanine; and (iii) an amino acid sequence comprising the amino acids 18-411 of the amino acid sequence represented by SEQ ID NO:2 where the amino acid 188 is substituted by an amino acid other than serine while the amino acid 191 is substituted by an amino acid other than alanine; or (b) a protein comprising an amino acid sequence where one or several amino acids other than the substituted amino acid(s) above are deleted, substituted or added in any one of the amino acid sequence of (i) to (iii) in (a) above, and having α-galactosidase activity.

Examples of the pharmaceutical composition of the invention include the proteins of (a) above where the amino acid other than serine is glutamic acid or aspartic acid, where the amino acid other than alanine is any one selected from the group consisting of leucine, valine, isoleucine, phenylalanine and methionine, and where the amino acid other than serine is glutamic acid while the amino acid other than alanine is leucine.

(3) A method for treating Fabry disease, comprising administering the pharmaceutical composition according to (1) or (2) above to a Fabry disease patient.

(4) A protein that acquired α-galactosidase activity by altering the structure of the active site of wild-type human α-N-acetylgalactosaminidase, wherein the protein comprises a signal peptide from wild-type human α-N-galactosidase.

(5) A protein of (a) or (b) below:

(a) a protein comprising an amino acid sequence of any one of (i) to (iii) below:

(i) an amino acid sequence where the amino acid 202 of the amino acid sequence represented by SEQ ID NO:6 is substituted by an amino acid other than serine;

(ii) an amino acid sequence where the amino acid 205 of the amino acid sequence represented by SEQ ID NO:6 is substituted by an amino acid other than alanine; or (iii) an amino acid sequence where the amino acid 202 of the amino acid sequence represented by SEQ ID NO:6 is substituted by an amino acid other than serine while the amino acid 205 is substituted by an amino acid other than alanine;

(b) a protein comprising an amino acid sequence where one or several amino acids other than the substituted amino acid(s) above are deleted, substituted or added in any one of the amino acid sequence of (i) to (iii) above, and having α-galactosidase activity.

Examples of the protein of the invention include the proteins above where the amino acid other than serine is glutamic acid or aspartic acid, where the amino acid other than alanine is any one selected from the group consisting of leucine, valine, isoleucine, phenylalanine and methionine, and where the amino acid other than serine is glutamic acid while the amino acid other than alanine is leucine.

(6) A gene coding for the protein according to (4) or (5) above.

(7) A gene comprising DNA of (a) or (b) below:
(a) DNA comprising a nucleotide sequence of any one of (i) to (iii) below:
(i) a nucleotide sequence where the nucleotides 604-606 of the nucleotide sequence represented by SEQ ID NO:5 are substituted by nucleotides representing a codon of an amino acid other than serine;
(ii) a nucleotide sequence where the nucleotides 613-615 of the nucleotide sequence represented by SEQ ID NO:5 are substituted by nucleotides representing a codon of an amino acid other than alanine; or
(iii) a nucleotide sequence where the nucleotides 604-606 of the nucleotide sequence represented by SEQ ID NO:5 are substituted by nucleotides representing a codon of an amino acid other than serine while the nucleotides 613-615 are substituted by nucleotides representing a codon of an amino acid other than alanine; or
(b) DNA that hybridizes with DNA having a nucleotide sequence complementary to DNA comprising the nucleotide sequence of any one of (i) to (iii) above under stringent conditions, that has the same nucleotides as the nucleotides at the substituted site above at the corresponding position, and that codes for a protein having α-galactosidase activity.

Examples of the gene of the invention include the genes above where the amino acid other than serine is glutamic acid or aspartic acid, where the amino acid other than alanine is any one selected from the group consisting of leucine, valine, isoleucine, phenylalanine and methionine, and where the amino acid other than serine is glutamic acid while the amino acid other than alanine is leucine.

(8) A recombinant vector comprising the gene according to (6) or (7) above.

(9) A transformant comprising a recombinant vector according to (8) above.

(10) A method for producing a protein, comprising the steps of: culturing the transformant according to (9) above; and collecting a protein having α-galactosidase activity from the resulting cultured product.

BRIEF DESCRIPTION OF DRAWINGS

FIG. 1 gives schematic views showing the three-dimensional structures of whole subunits of wild-type α-GAL and wild-type α-NAGA.

FIG. 3 is a schematic view comparing the numbers and the positions of the N-glycosylation sites between the subunits of wild-type α-GAL and wild-type α-NAGA.

FIG. 4 gives schematic views in which the N-glycosylation sites (as stick models (except the substrates)) are shown in the structures of the subunits of wild-type α-GAL and wild-type α-NAGA, respectively.

FIG. 5(a) is a schematic view showing wild-type α-NAGA binding to its substrate, whereas FIG. 5(b) is a schematic view showing an α-NAGA mutant, i.e., α-NAGA (S188E/A191L), binding to a substrate of α-GAL.

BEST MODES FOR CARRYING OUT THE INVENTION

Figure 2A:
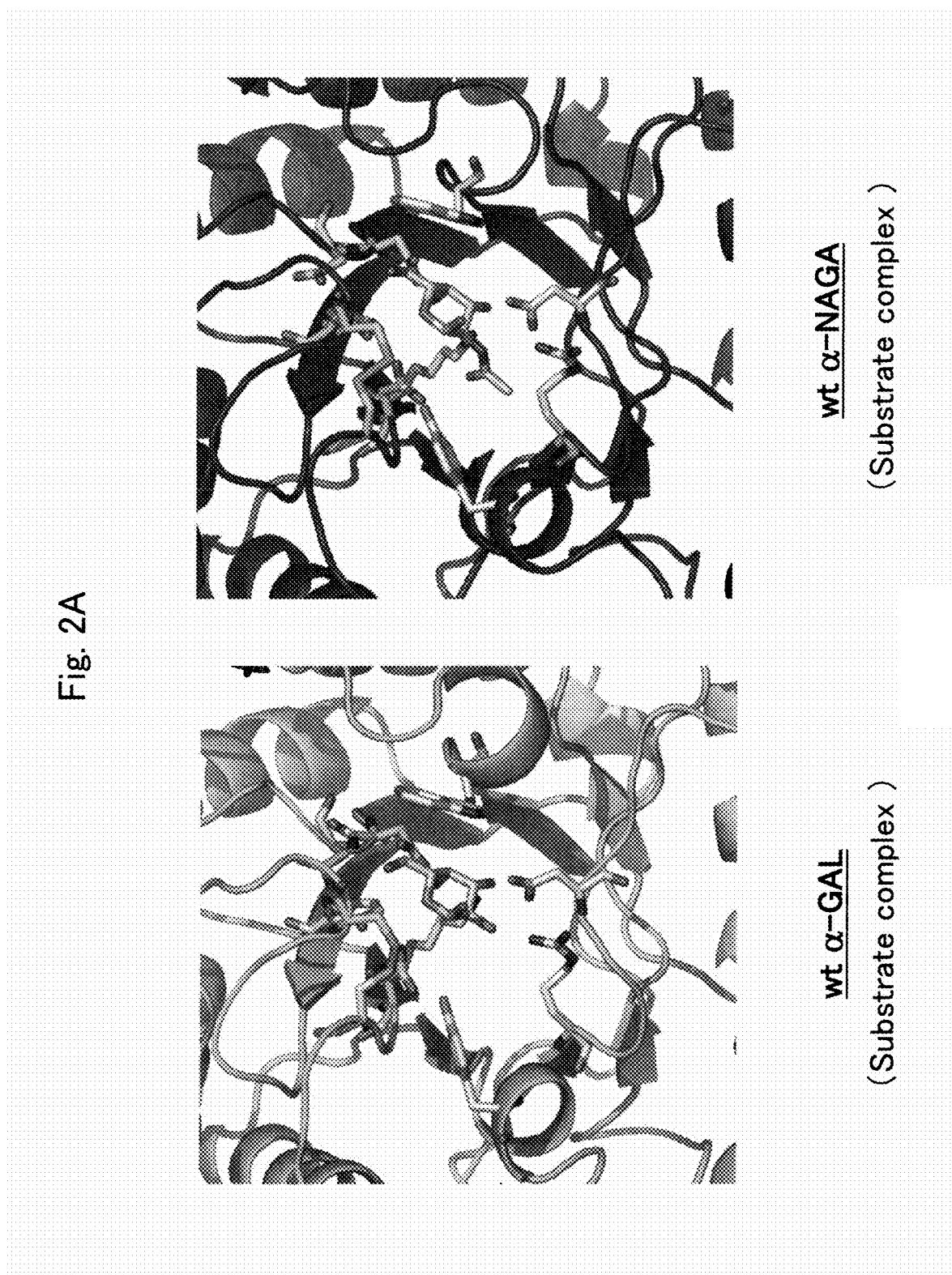
FIG. 2A gives schematic views showing the structures of the active sites of wild-type α-GAL and wild-type α-NAGA. Note that the amino acids (as stick model (except the substrates)) shown in the figure indicate the positions of the amino acid residues that are common between α-GAL and α-NAGA in the structure, among the amino acid residues in the vicinity of the substrates of wild-type α-GAL and wild-type α-NAGA.

Hereinafter, the present invention will be described in detail. The scope of the present invention should not be restricted by the descriptions below, while, in addition to exemplifications described below, various modifications can be made to the invention without departing from the spirit of the present invention.

This description includes the entirety of the description of Japanese Patent Application No. 2007-133536, which claims the priority of this application. In addition, all publications, for example, prior art documents, unexamined patent application publications, patent publications, and other patent documents cited herein are incorporated herein by reference.

1. GENERAL DESCRIPTION OF THE INVENTION (1) Definition of Terms

Herein, unless otherwise stated, the terms are defined as follows.

The terms "α-galactosidase" and "α-GAL" both refer to "human α-galactosidase A".

The terms "α-N-acetylgalactosaminidase" and "α-NAGA" both refer to "human α-galactosidase B", i.e., "human α-N-acetylgalactosaminidase".

The abbreviation "wt" stands for wild type.

The abbreviation "M6P" stands for "mannose-6-phosphate".

The term "α-GAL activity" refers to the later-described activity of hydrolyzing α-GAL substrate (see reaction formula (1) below), which is not limited to the activity of α-GAL protein (wild-type α-GAL).

The term "α-NAGA activity" refers to the later-described activity of hydrolyzing α-NAGA substrate (see reaction formula (2) below), which is not limited to the activity of α-NAGA protein (wild-type α-NAGA).

The phrase "acquired α-GAL activity" means that the binding reactivity with α-GAL substrate became relatively higher than that with α-NAGA substrate at the substrate binding site.

The phrase "have substrate specificity of α-GAL" means that the structure of an active site (particularly, position and type of an amino acid residue that plays an important role for the binding reactivity to the substrate) is the same as that of wild-type α-GAL.

The terms "amino acid 188" and "amino acid 191" refer to the positions of amino acids with respect to the amino acid sequence (SEQ ID NO:2) of wild-type α-NAGA (a position counted from the amino acid residue at the N-terminal (as amino acid 1) toward the C-terminal of this amino acid sequence).

The term "α-NAGA mutant" basically refers to any wild-type α-NAGA mutant, without being limited to a particular mutant (amino acid mutant). Herein, a mutant protein having serine at amino acid 188 substituted by glutamic acid, and alanine at amino acid 191 substituted by leucine in the amino acid sequence (SEQ ID NO:2) of wild-type α-NAGA (and thus referred to as "α-NAGA (S188E/A191L)") may be referred to (defined) as an α-NAGA mutant.

The term "α-GAL signal peptide-fused α-NAGA" generally refers to a protein having the signal peptide moiety of wild-type α-NAGA (a peptide moiety consisting of amino acids 1-17 of the amino acid sequence represented by SEQ ID NO:2) replaced with the signal peptide moiety of wild-type α-GAL (a peptide moiety consisting of amino acids 1-31 of the amino acid sequence represented by SEQ ID NO:10). Here, although the signal peptide moiety is generally removed upon extracellular secretion following the intracellular expression of the protein, according to the present invention, the protein after the extracellular secretion may also be referred to as "α-GAL signal peptide-fused α-NAGA" for the sake of convenience.

The terms "α-GAL signal peptide-fused α-NAGA mutant" and "α-GAL signal peptide-fused α-NAGA (S188E/A191L)" generally refer to a protein having the signal peptide moiety of an α-NAGA mutant (for example, a peptide moiety consisting of amino acids 1-17 of the amino acid sequence represented by SEQ ID NO:2) replaced with the signal peptide moiety of wild-type α-GAL (a peptide moiety consisting of amino acids 1-31 of the amino acid sequence represented by SEQ ID NO:10). Here, although the signal peptide moiety is generally removed upon extracellular secretion following the intracellular expression of the protein, according to the present invention, the protein after the extracellular secretion may also be referred to as "α-GAL signal peptide-fused α-NAGA mutant" and "α-GAL signal peptide-fused α-NAGA (S188E/A191L)" for the sake of convenience.

(2) Description of Sequence Listing

Enzyme proteins of the nucleotide sequences and amino acid sequences represented by SEQ ID NOS:1-10 in the present description are shown in Table A below. In Table A, the term "main body" refers to a part that becomes the mature protein without the signal peptide moiety. The symbol "+" represents binding between the indicated signal peptide and the main body.

TABLE A

| SEQ ID NO | Protein |
| --- | --- |
| SEQ ID NO: 1 (nucleotide sequence) | wt α-NAGA |
| SEQ ID NO: 2 (amino acid sequence) | (signal peptide of wt α-NAGA + main body of wt α-NAGA) |
| SEQ ID NO: 3 (nucleotide sequence) | α-NAGA mutant (α-NAGA (S188E/A191L)) |
| SEQ ID NO: 4 (amino acid sequence) | (signal peptide of wt α-NAGA + main body of α-NAGA mutant) |
| SEQ ID NO: 5 (nucleotide sequence) | signal peptide of wt α-GAL + |
| SEQ ID NO: 6 (amino acid sequence) | main body of wt α-NAGA |
| SEQ ID NO: 7 (nucleotide sequence) | signal peptide of wt α-GAL + |
| SEQ ID NO: 8 (amino acid sequence) | main body of α-NAGA mutant |
| SEQ ID NO: 9 (nucleotide sequence) | wt α-GAL |
| SEQ ID NO: 10 (amino acid sequence) | (signal peptide of wt α-GAL + main body of wt α-GAL) |

(3) Summary of the Invention

The present invention provides a pharmaceutical composition for treating Fabry disease that can be effectively used for enzyme replacement therapy for Fabry disease and that can exert an excellent therapeutic effect, as well as a recombinant protein serving as an excellent novel highly functional enzyme which can be used as an active element of the pharmaceutical composition.

For an existing agent used for enzyme replacement for treating Fabry disease, recombinant human α-GAL produced in a cell derived from a mammal, such as a CHO cell or a human fibroblast, is used. However, the use of this human α-GAL causes problems such as allergic side effects, instability in blood, and a low uptake efficiency by a cell of an affected organ, and thus places a very large burden on patients in the actual therapy. Accordingly, a solution to these problems has been desired.

In order to solve these problems, the present inventors studied whether or not an enzyme other than α-GAL can be used as an enzyme used for enzyme replacement for treating Fabry disease. Specifically, the present inventors focused on "α-N-acetylgalactosaminidase (α-NAGA)", which is a lysosomal enzyme similar to α-GAL (meaning that the localization of α-NAGA in a cell is the same as that of α-GAL), and whose overall structure is very similar to that of α-GAL but with different substrate specificity.

α-GAL used to be called α-galactosidase A. An isozyme called α-galactosidase B having biochemical properties very similar to those of α-GAL was believed to exist. It was known that α-galactosidase B had higher stability than that of α-GAL, but did not have the ability to degrade globotriaosylceramide (ceramide trihexoside (CTH)), which is accumulated within the body due to Fabry disease. Afterward, it became clear that α-galactosidase B was actually α-N-acetylgalactosaminidase (α-NAGA). α-NAGA is encoded by a gene which is considered to be originated from the same ancestor gene as that of a gene encoding α-GAL. The cDNA of α-NAGA has been cloned, and it is known that the gene encodes a protein composed of total of 411 amino acid residues containing a signal peptide composed of 17 amino acid residues. In addition, when the structure of human α-NAGA is compared with that of human α-GAL, homology thereof is 57.9% at the nucleotide sequence level, and 52.2% at the amino acid sequence level. Furthermore, like human α-GAL, human α-NAGA is an enzyme that exists in the form of a homodimer.

On the basis of the above knowledge, the present inventors first constructed three-dimensional structural models of α-NAGA and α-GAL to compare them. More specifically, a three-dimensional structural model of human α-NAGA was constructed with reference to the structural information of chicken α-NAGA (ID: 1KTC) registered with Protein Data Bank (PDB), and this structure was compared with the three-dimensional structure of human α-GAL (ID: 1R47) registered with PDB. As a result, it was found that the three-dimensional structure of human α-NAGA was very similar to the three-dimensional structure of human α-GAL with respect to the entire structure and the active site. Regarding the active site, to be exact, only a few amino acid residues are different from each other. However, among these amino acid residues, there are important amino acid residues present at the substrate-binding site, which affect the difference between the substrate specificities of α-GAL and α-NAGA. In this regard, it was found that there is a significant difference in the three-dimensional structures between the active sites of α-GAL and α-NAGA.

Figure 2B:
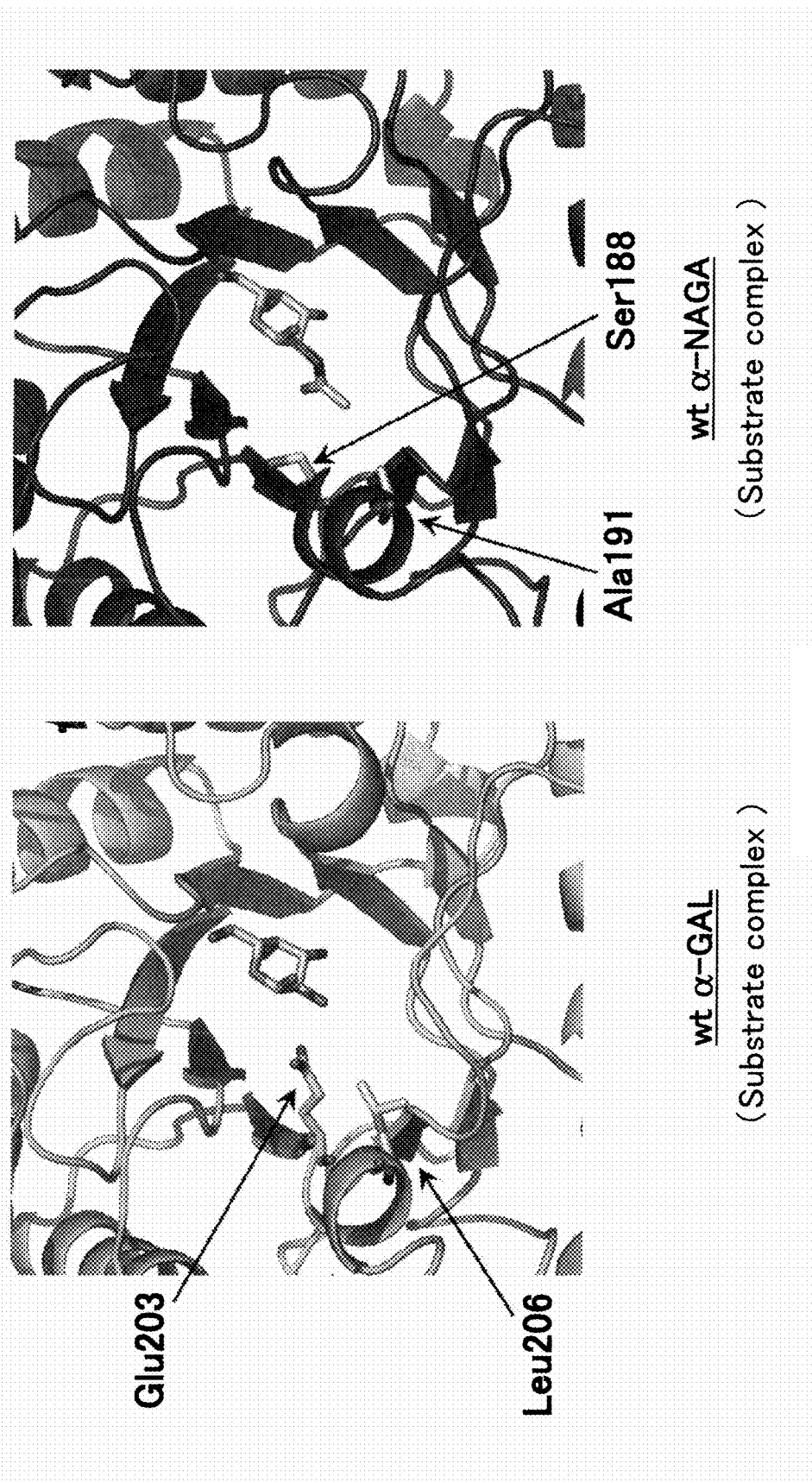
FIG. 2B gives schematic views showing the structures of the active sites of wild-type α-GAL and wild-type α-NAGA. Note that the amino acids (as stick model (except the substrates)) shown in the figure indicate the positions of the amino acid residues that are different between α-GAL and α-NAGA in the structure, among the amino acid residues in the vicinity of the substrates of wild-type α-GAL and wild-type α-NAGA.

Thus, α-NAGA is an enzyme which differs from α-GAL in a part of the structure of the substrate-binding site at the active site but is very similar to α-GAL with respect to the structure and properties regarding the other parts including the catalytic site (see FIGS. 1, 2A, and 2B). Therefore, the catalytic reaction mechanism of α-NAGA is very similar to the catalytic reaction mechanism of α-GAL with respect to, for example, the types of reaction substrate and reaction product.

Hence, the present inventors focused on α-NAGA as described above and found that when the substrate specificity of α-NAGA is modified to have α-galactosidase activity by altering the structure of the active site (in particular, the substrate-binding site) by gene manipulation of α-NAGA (for example, by substituting the α-NAGA-type amino acid residues that play the key role among the amino acid residues related to the substrate recognition of α-NAGA by the α-GAL-type amino acid residues), a novel excellent highly functional enzyme that can be used for treating Fabry disease can be created.

The reasons why the present inventors focused on α-NAGA further include the following points (i) to (iii):

(i) α-NAGA is the responsible enzyme of Schindler disease and Kanzaki disease (note that a disease that develops due to abnormality of the same enzyme as an enzyme that develops Schindler disease and that has a clinical phenotype different from that of Schindler disease is called Kanzaki disease), and deficiency of α-NAGA is a cause of the development of Schindler disease and Kanzaki disease. In general, however, the development of Schindler disease or Kanzaki disease is very rare even in Fabry disease patients. Accordingly, almost all Fabry disease patients can be said to have α-NAGA normally. Therefore, it is believed that even when a protein in which only the substrate specificity of α-NAGA is modified into the substrate specificity of α-GAL is administered as an enzyme agent for enzyme replacement, the antigenicity thereof rarely appears as if wild-type α-NAGA is administered, and thus there is substantially no probability that an adverse immune reaction such as an allergic side effect is induced.

(ii) α-NAGA functions in the form of a homodimer as α-GAL does but in general, α-NAGA is more stable than α-GAL upon homodimer formation. The three-dimensional structure model constructed by the present inventors also supports this stability. Specifically, it was confirmed that, upon formation of the dimer of human α-NAGA, two bonds via electrostatic interaction were observed between Asp45 and Arg350 in the two subunits, whereas such bonds were not observed in α-GAL. Accordingly, it is believed that, like α-NAGA, an α-NAGA mutant also has higher stability in blood (in plasma), as compared to α-GAL, and is very suitable for enzyme replacement therapy. In addition, if the dimer proportion is increased due to the above stability, it is expected that the uptake efficiency by a lysosome in a cell is also improved in relation to point (iii) below. Furthermore, it is advantageous in that the effect can be maintained as an enzyme preparation for a long period of time before administration.

(iii) It is necessary that an enzyme used for enzyme replacement therapy can be taken up by a lysosome in a cell of an affected organ. In general, the transportation from a cell membrane to a lysosome is performed via a calcium-independent M6P receptor, which recognizes mannose-6-phosphate (M6P) present in sugar chain portions of the enzyme. Accordingly, an enzyme having a larger number of sugar chains (N-type sugar chains) that allow binding by the M6P residue is preferable because an uptake efficiency by a lysosome is higher. Regarding the number of the above sugar chains, it has become clear, by an X-ray crystal structure analysis, that three sugar chains per subunit (at three positions, Asn139, Asn192 and Asn215; six sugar chains in the case where a dimer is formed) are present in α-GAL. In contrast, in α-NAGA, five sugar chains per subunit (ten sugar chains in the case where a dimer is formed) are present (see FIGS. 3 and 4). Among these sugar chains, three sugar chains (at three positions, Asn124, Asn177 and Asn201) correspond to the positions of the sugar chains in α-GAL, and two other sugar chains (at two positions, Asn359 and Asn385) are specific to α-NAGA. Accordingly, it is believed that an uptake efficiency of α-NAGA in blood by a lysosome in a cell of an affected organ is higher than that in the case of α-GAL.

From the above standpoints, the present inventors focused on the amino acid 188 (serine (Ser)) and the amino acid 191 (Ala (alanine)) among an amino-acid residue group constituting the substrate-binding site of α-NAGA. The present inventors attempted to prepare a recombinant enzyme (mutant enzyme) in which the 188th serine (Ser) was substituted by glutamic acid (Glu) and the 191st alanine was substituted by leucine (Leu). Subsequently, this recombinant enzyme was expressed using fibroblasts derived from a Fabry disease patient, collected, and analyzed. As a result, high α-GAL activity was observed. In addition, the stability of this recombinant enzyme in blood was significantly higher than that of wild-type α-GAL. By using such a recombinant enzyme with altered substrate specificity, a pharmaceutical composition for treating Fabry disease that can effectively be used for enzyme replacement for treating Fabry Disease can be provided which is superior to the existing pharmaceutical compositions.

2. PROTEIN

A protein of the present invention is a protein that can be used as an active element of a later-described pharmaceutical composition of the invention for treating Fabry disease, specifically a mutant enzyme of α-N-acetylgalactosaminidase (α-NAGA).

More specifically, the protein of the present invention is a protein of (1a) or (1b) below, preferably a protein of (1c) below.

(1a) a protein which has acquired α-galactosidase (α-GAL) activity by altering the structure of the active site (in particular, the substrate-binding site) of wild-type α-NAGA, preferably a protein having the substrate specificity of α-GAL.

(1b) a protein of (1a) above with a signal peptide. Here, the type of the signal peptide is not particularly limited, and it may be a signal peptide derived from wild-type α-NAGA or other protein.

(1c) a protein of (1b) above, where the signal peptide is derived from wild-type α-GAL.

Herein, the phrase "acquired α-GAL activity" means, as already mentioned above, that the binding reactivity to a substrate of α-GAL becomes relatively higher than the binding reactivity to a substrate of α-NAGA at the substrate-binding site of α-NAGA. Accordingly, the above structural alteration is not limited to a structural alteration that binding between α-NAGA and the substrate thereof completely impossible. Thus, the structural alteration may be one that makes the binding reactivity to the substrate of α-GAL significantly higher than the binding reactivity to the substrate of α-NAGA, which has originally been relatively significantly higher than the binding reactivity to the substrate of α-GAL. Furthermore, the phrase "having the substrate specificity of α-GAL", as already mentioned above, means that the structure of the active site (in particular, the positions and the types of amino acid residues which play an important role in the binding reactivity to a substrate) is the same as that of α-GAL.

In the present invention, the term "substrate of α-GAL" refers to a natural compound such as a glycolipid, e.g., globotriaosylceramide (ceramide trihexoside (CTH)), which has a galactose residue bound to the non-reducing end via α-bond, or a synthetic compound, e.g., 4-methylumbelliferyl-α-D-galactoside. The term "substrate of α-NAGA" refers to a natural compound such as an oligosaccharide, glycoprotein or glycolipid having an N-acetylgalactosamine residue bound to the non-reducing end via α-bond, or a synthetic compound, e.g., 4-methylumbelliferyl-α-N-acetyl-D-galactosaminide.

Here, a catalytic reaction of wild-type α-GAL is represented by reaction formula (1) below, and a catalytic reaction of wild-type α-NAGA is represented by reaction formula (2) below.

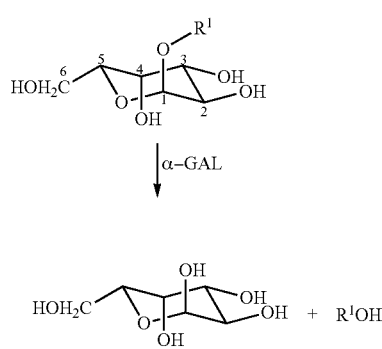

(1)

[In reaction formula (1), when the substrate is a natural compound, $R^1$ represents "a group derived from a sugar complex", and when the substrate is a synthetic compound, $R^1$ represents "a 4-methylumbelliferyl group".]

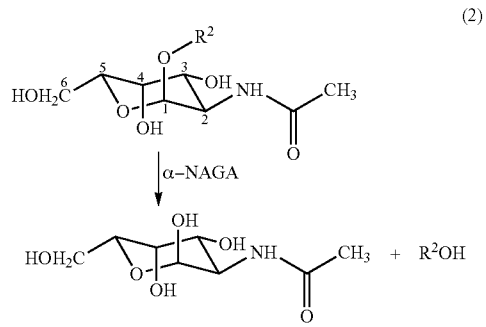

(2)

[In reaction formula (2), when the substrate is a natural compound, $R^2$ represents "a group derived from a sugar complex", and when the substrate is a synthetic compound, $R^2$ represents "a 4-methylumbelliferyl group".]

Preferable examples of the protein of the present invention include proteins comprising the amino acid sequence of the following (2a) or (2b), and having α-GAL activity.

(2a) an amino acid sequence in which at least one of the amino acids 188 and 191 included in the amino acid sequence of wild-type α-NAGA is substituted by another amino acid, preferably, an amino acid sequence in which both of the amino acids 188 and 191 are substituted by other amino acids.

(2b) an amino acid sequence in which one or several amino acids except the amino acids 188 and 191 included in the amino acid sequence of (2a) above are deleted, substituted or added.

Information on the amino acid sequence (SEQ ID NO:2) of the subunit of wild-type α-NAGA (homodimer) and information on the nucleotide sequence (SEQ ID NO:1) encoding the above amino acid sequence are published, for example, as "accession number: NM_000262" from GenBank, and registered in "entry name: NAGAB_HUMAN", accession number: P17050" with Swiss-Prot. Similarly, information on the amino acid sequence (SEQ ID NO:10) of the subunit of wild-type α-GAL (homodimer) and information on the nucleotide sequence (SEQ ID NO:9) encoding the above amino acid sequence are published, for example, as "accession number: NP_000160" from GenBank, and registered in "entry name: AGAL_HUMAN", accession number: P06280" with Swiss-Prot.

Herein, examples of the above "amino acid sequence in which one or several amino acids are deleted, substituted or added" preferably include amino acid sequences in which about one to ten amino acids, and preferably about one to five amino acids are deleted, substituted or added.

Furthermore, regarding "the protein composed of an amino acid sequence in which one or several amino acids are deleted, substituted or added", it is important that the protein can stably exhibit α-GAL activity. Therefore, for example, all or some (preferably, all) of the amino acids 28-31, the amino acids 77-81, the amino acids 117-127, the amino acids 150-158, the amino acid 192, the amino acids 209-220 and the amino acids 242-254, which are believed to be important for the binding performance (substrate-binding performance) with an α-galactose residue of a substrate of α-GAL and the catalytic reactivity to the substrate (in particular, the 156th and 217th aspartic acids (Asp: D) at the catalytic site; the 45th aspartic acid (Asp: D) and the 350th arginine (Arg: R) that are believed to be important for forming a homodimer; and the amino acids 124, 177, 201, 359 and 385 (all of which being asparagine (Asn: N)) as N-type-sugar-chain-binding sites)

are preferably not mutated (deleted, substituted or added) from the amino acid sequence of wild-type α-NAGA.

The other amino acid residue substituting for the amino acid residue 188 is not particularly limited as long as the amino acid residue is not serine (Ser: S). For example, glutamic acid (Glu: E) and aspartic acid (Asp: D) are preferable, and glutamic acid is more preferable. Similarly, the other amino acid residue substituting for the amino acid residue 191 is not particularly limited as long as the amino acid residue is not alanine (Ala: A). For example, leucine (Leu: L), valine (Val: V), isoleucine (Ile: I), phenylalanine (Phe: F) and methionine (Met: M) are preferable, and leucine is more preferable. Particularly preferable amino acids for substitution among them are glutamic acid for the amino acid 188 and leucine for the amino acid 191. Note that, preferably, the amino acids after the substitution do not substantially affect the structure composed of the rest of the unsubstituted amino acids. From this point of view, in a particularly preferable substitution embodiment, the amino acid residue 188 is glutamic acid and the amino acid residue 191 is leucine.

Figure 5:
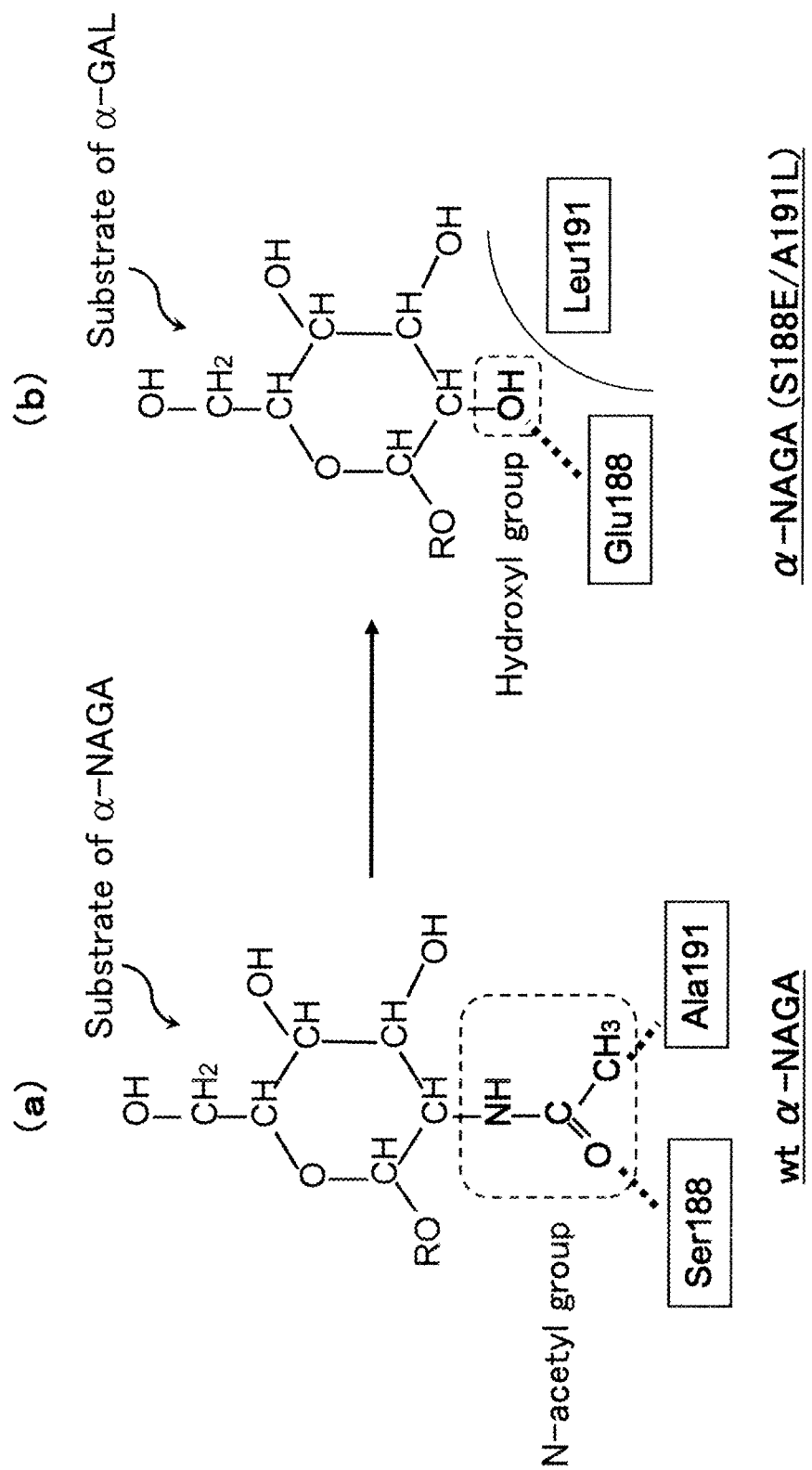

By substituting the amino acid 188 and the amino acid 191 present at the substrate-binding sites as described above, the following effects can be achieved. Specifically, as exemplified in FIG. 5, regarding the amino acid residue 188, the interaction with the N-acetyl group (in particular, the oxygen atom) in the substrate of α-NAGA can be canceled, while producing a binding action with the hydroxyl group in the substrate of α-GAL. Regarding the amino acid residue 191, the interaction with the N-acetyl group (in particular, the methyl group) in the substrate of α-NAGA can be canceled, while limiting the binding space of the substrate (in particular, the space into which the N-acetyl group is incorporated). As a result, the recombinant enzyme (recombinant protein) obtained after the substitution of the amino acids has a binding reactivity to the substrate of α-GAL higher than the binding reactivity to the substrate of α-NAGA, and thus can serve as an enzyme with α-GAL activity significantly higher than α-NAGA activity. The recombinant enzyme having an amino acid sequence in which at least the amino acid 188 (serine) is substituted by glutamic acid and the amino acid 191 (alanine) is substituted by leucine is particularly preferable from the standpoint that the above-described effects can satisfactorily be achieved.

In addition, the protein of the present invention is preferably a protein described in (3a) or (3b) below:

(3a) a protein containing any one of the amino acid sequences described in (i) to (iii) below:

(i) an amino acid sequence composed of the amino acids 18-411 of the amino acid sequence represented by SEQ ID NO:2 in which the amino acid 188 is substituted by an amino acid other than serine;

(ii) an amino acid sequence composed of the amino acids 18-411 of the amino acid sequence represented by SEQ ID NO:2 in which the amino acid 191 is substituted by an amino acid other than alanine; or (iii) an amino acid sequence composed of the amino acids 18-411 of the amino acid sequence represented by SEQ ID NO:2 in which the amino acid 188 is substituted by an amino acid other than serine while the amino acid 191 is substituted by an amino acid other than alanine; or (3b) a protein containing any one of the amino acid sequences described in (i) to (iii) of (3a) above in which one or several amino acids other than the amino acid(s) at the substituted site(s) are deleted, substituted or added, and having α-galactosidase activity.

The amino acid sequence represented by SEQ ID NO:2 is an amino acid sequence composed of 411 amino acids constituting wild-type α-NAGA.

Specifically, the protein described in (3a) above is a protein composed of the amino acid sequence represented by SEQ ID NO:2 substituted as described in (i) to (iii), where it consists of an amino acid sequence ranging from the amino acids 18 to 411 and excluding the amino acids 1-17 that constitute the signal peptide of wild-type α-NAGA. As described above, the amino acid residues 188 and 191 are each one of the amino acids constituting the substrate-binding sites.

Here, a preferable example of the amino acid sequence containing an amino acid sequence ranging from the amino acids 18 to 411 may be an amino acid sequence having a signal peptide linked to the N-terminal of the amino acid sequence ranging from the amino acids 18 to 411. The signal peptide is not limited as long as it allows the protein to pass through a cell membrane of an affected organ. For example, a signal peptide is preferably a signal peptide of a lysosomal enzyme such as wild-type α-NAGA or wild-type α-GAL or a signal peptide of a secretase such as preprotrypsin, more preferably a signal peptide of wild-type α-NAGA or wild-type α-GAL, and still more preferably a signal peptide of wild-type α-GAL. The signal peptide of wild-type α-NAGA, as already described above, is a peptide composed of the amino acids 1-17 of the amino acid sequence of wild-type α-NAGA represented by SEQ ID NO:2. The signal peptide of wild-type α-GAL is a peptide composed of the amino acids 1-31 included in the amino acid sequence of wild-type α-GAL represented by SEQ ID NO:10. The signal peptide of preprotrypsin is a peptide composed of the amino acid sequence represented by SEQ ID NO:12.

As the protein described in (3a), a protein containing the amino acid sequence described in (iii) is particularly preferable among proteins containing the amino acid sequences described in (i), (ii) and (iii).

A preferable example of the protein described in (3a) above includes a protein in which "the amino acid other than serine" described in (i) and (iii) above is glutamic acid or aspartic acid. Similarly, another preferable example of the protein described in (3a) above includes a protein in which "the amino acid other than alanine" described in (ii) and (iii) is one selected from the group consisting of leucine, valine, isoleucine, phenylalanine and methionine.

Furthermore, a particularly preferable example of the protein described in (3a) above includes a protein in which "the amino acid other than serine" described in (i) to (iii) is glutamic acid and "the amino acid other than alanine" described in (i) to (iii) is leucine. A preferable example of such protein includes a protein (α-NAGA (S188E/A191L)) in which the 188th serine is substituted by glutamic acid and the 191st alanine is substituted by leucine in the amino acid sequence of wild-type α-NAGA (SEQ ID NO:2) (see FIG. 6 and SEQ ID NO:4). In general, the alphabetical notation of an amino acid is expressed in three letters (e.g., "Ser") or one letter (e.g., "S"). The alphabetical letter preceding the number (e.g., "188") representing the position of an amino acid counted from the N-terminal represents an amino acid in one-letter notation before the substitution, while the alphabetical letter following the number represents an amino acid in one-letter notation after the substitution. Accordingly, for example, the notation "S188E" represents that the 188th Ser is substituted by Glu (the same similarly applies hereinafter).

The protein described in (3b) above is not limited as long as the protein contains an amino acid sequence in which one or several (for example, about one to ten, and preferably about one to five) amino acids other than the amino acid(s) located at the substituted site(s) are deleted, substituted or added in any one of the amino acid sequences described in (i) to (iii) above included in the protein described in (3a) above, and has α-galactosidase activity. Herein, the term "the substituted site" refers to, among the 394 amino acid residues constituting the amino acid sequences described in (i) to (iii), the amino acid residue corresponding to the position of the amino acid 188 in the amino acid sequence represented by SEQ ID NO:2 (provided that the amino acid sequence is limited to the amino acid sequence described in (i) or (iii)), and the amino acid residue corresponding to the position of the amino acid 191 in the amino acid sequence represented by SEQ ID NO:2 (provided that the amino acid sequence is limited to the amino acid sequence described in (ii) or (iii)). More specifically, the former amino acid residue refers to the amino acid residue 171 in the amino acid sequence described in (i) or (iii), and the latter amino acid residue refers to the amino acid residue 174 in the amino acid sequence described in (ii) or (iii).

Note that it is important that the protein described in (3b) above is a protein that can stably exhibit α-GAL activity. Therefore, for example, amino acid residues which are believed to be important for binding performance (substrate-binding performance) with an α-galactose residue of a substrate of α-GAL and the catalytic reactivity to the substrate are preferably amino acid residues that are not mutated (deleted, substituted or added) from the amino acid sequences described in (i) to (iii) above. Preferable examples of such amino acid residues include, among the amino acid residues constituting the amino acid sequences described in (i) to (iii) above, amino acid residues corresponding to the positions of the amino acids 28-31, the amino acids 77-81, the amino acids 117-127, the amino acids 150-158, the amino acid 192, the amino acids 209-220, and the amino acids 242-254 (in particular, the aspartic acids 156 and 217 (Asp: D) at the catalytic site) in the amino acid sequence represented by SEQ ID NO:2.

Similarly, amino acid residues which are believed to be important for forming a homodimer are also preferably amino acid residues that are not mutated (deleted, substituted or added) from the amino acid sequences described in (i) to (iii) above. Preferable examples of such amino acid residues include, among the amino acid residues constituting the amino acid sequences described in (i) to (iii) above, amino acid residues corresponding to the positions of the amino acids 45 and 350 (specifically, the 45th aspartic acid (Asp: D) and the 350th arginine (Arg: R)) in the amino acid sequence represented by SEQ ID NO:2.

Furthermore, amino acid residues which are N-type-sugar-chain-binding sites are also preferably not mutated (deleted, substituted or added) from the amino acid sequences described in (i) to (iii) above. Preferable examples of such amino acid residues include, among the amino acid residues constituting the amino acid sequences described in (i) to (iii) above, amino acid residues corresponding to the positions of the amino acids 124, 177, 201, 359 and 385 (all of which being asparagine (Asn: N)) in the amino acid sequence represented by SEQ ID NO:2.

In addition, a protein of the invention is preferably a protein of (4a) or (4b) below.

(4a) a protein containing any one of the amino acid sequences described in (i) to (iii) below:
(i) an amino acid sequence having the amino acid 202 substituted by an amino acid other than serine in the amino acid sequence represented by SEQ ID NO:6;
(ii) an amino acid sequence having the amino acid 205 substituted by an amino acid other than alanine in the amino acid sequence represented by SEQ ID NO:6; or (iii) an amino acid sequence having the amino acid 202 substituted by an amino acid other than serine and the amino acid 205 substituted by an amino acid other than alanine in the amino acid sequence represented by SEQ ID NO:6; or (4b) a protein containing an amino acid sequence in which one or several amino acids other than those located at the substituted site(s) are deleted, substituted or added in any one of the amino acid sequences described in (i) to (iii) above, and having α-galactosidase activity.

The amino acid sequence represented by SEQ ID NO:6 is an amino acid sequence (with a total of 425 amino acids) in which the amino acids 1-17 corresponding to the signal peptide moiety are altered by the signal peptide moiety of wild-type α-GAL in an amino acid sequence composed of 411 amino acids constituting wild-type α-NAGA, which is a so-called fusion protein. Here, the signal peptide moiety of the wild-type α-GAL, as already described above, is a peptide moiety of the amino acids 1-31 among the amino acid sequence constituting the wild-type α-GAL represented by SEQ ID NO:10.

In the amino acid sequence constituting the protein of (4a) above, the amino acid residues 188 and 191 are each one of the amino acids constituting the substrate-binding sites.

As the protein described in (4a) above, a protein including the amino acid sequence described in (iii) above is particularly preferable among proteins having the amino acid sequence described in (i), (ii) or (iii) above.

A particularly preferable example of the protein described in (4a) is a protein in which "the amino acid other than serine" described in (i) and (iii) is glutamic acid or aspartic acid. Similarly, another preferable example of the protein described in (4a) is a protein in which "the amino acid other than alanine" described in (ii) and (iii) is one selected from the group consisting of leucine, valine, isoleucine, phenylalanine and methionine.

Furthermore, a particularly preferable example of the protein described in (4a) includes a protein in which "the amino acid other than serine" described in (i) to (iii) above is glutamic acid while "the amino acid other than alanine" described in (i) to (iii) above is leucine. A preferable example of such protein includes a protein (α-GAL signal peptide-fused α-NAGA (S202E/A205L)) having the 202nd serine substituted by glutamic acid and the 205th alanine substituted by leucine in the amino acid sequence represented by SEQ ID NO:6.

The protein described in (4b) is not limited as long as it includes an amino acid sequence in which one or several (for example, about 1-10, and preferably about 1-5) amino acids other than the amino acid(s) located at the substituted site(s) are deleted, substituted or added in any one of the amino acid sequences described in (i) to (iii) included in the protein described in (4a) above, and has α-GAL activity. Herein, the term "the substituted site" refers to the amino acid residue 202 (provided that the amino acid sequence is limited to the amino acid sequence described in (i) or (iii)) and the amino acid residue 205 (provided that the amino acid sequence being limited to the amino acid sequence described in (ii) or (iii)) among the 425 amino acid residues constituting the amino acid sequences described in (i) to (iii) above.

Note that it is important that the protein described in (4b) above is a protein that can stably exhibit α-GAL activity. Therefore, for example, amino acid residues which are believed to be important for binding performance (substrate-binding performance) with an α-galactose residue of an α-GAL substrate and the catalytic reactivity to the substrate are preferably amino acid residues that are not mutated (deleted, substituted or added) from the amino acid sequences described in (i) to (iii). Preferable examples of such amino acid residues include amino acid residues 42-45, 91-95, 131-141, 164-172, 206, 223-234 and 256-268 (in particular, the 170th and 231st aspartic acids (Asp: D) at the catalytic site) among the 425 amino acid residues constituting the amino acid sequences described in (i) to (iii) above.

Similarly, amino acid residues which are believed to be important for forming a homodimer are also preferably not mutated (deleted, substituted or added) from the amino acid sequences described in (i) to (iii) above. Preferable examples of such amino acid residues include amino acid residues 59 and 364 (specifically, the 59th aspartic acid (Asp: D) and the 364th arginine (Arg: R)) among the 425 amino acid residues constituting the amino acid sequences described in (i) to (iii) above.

Furthermore, amino acid residues which are N-type-sugar-chain-binding sites are also preferably not mutated (deleted, substituted or added) from the amino acid sequences described in (i) to (iii) above. Preferable examples of such amino acid residues include amino acid residues 138, 191, 215, 373 and 399 (all of which being asparagine (Asn: N)) among the 425 amino acid residues constituting the amino acid sequences described in (i) to (iii) above.

With respect to the above-described proteins of the present invention, α-GAL activity can be measured as follows. For example, a target protein is expressed in a cell derived from a mammal, such as a CHO cell or a human fibroblast, and collected therefrom. The protein (enzyme solution) is then mixed with 4-methylumbelliferyl-α-D-galactoside (a synthetic substrate obtained from α-D-galactose and 4-methylumbelliferone (fluorogenic substrate)), and the mixture is allowed to react under an acidic condition. The amount of 4-methylumbelliferone released is detected as a unit quantity of the enzyme solution per unit time to measure the α-GAL activity.

α-NAGA activity can also be measured as follows. A target protein is expressed and collected in a similar manner to the measurement for the α-GAL activity above. The protein (enzyme solution) is then mixed with 4-methylumbelliferyl-α-N-acetyl-D-galactosaminide (a synthetic substrate obtained from α-N-acetyl-D-galactosamine and 4-methylumbelliferone (fluorogenic substrate)), and the mixture is allowed to react under an acidic condition. The amount of 4-methylumbelliferone which can be released is detected as a unit quantity of the enzyme solution per unit time to measure the α-NAGA activity.

In the above methods of measuring α-GAL activity and α-NAGA activity, various types of known detection methods can be employed for detecting the fluorogenic substrate. For example, a detection method using a fluorophotometer or the like is preferable. The target protein can be expressed by incorporating a gene encoding the protein into a known expression vector or the like, and then introducing the vector into a cell.

3. RECOMBINANT GENE

A gene of the invention codes for the above-described protein of the invention.

Preferable examples of a gene of the invention include genes including DNA described in (1a) or (1b) below. Although the DNAs described in (1a) and (1b) are preferably structural genes of the protein of the present invention, the gene including any of these DNAs is not limited thereto and it may consist of the DNA alone or it may contain the DNA together with other known nucleotide sequences required for gene expression (such as a transcriptional promoter, SD sequence, Kozak sequence and a terminator).

(1a) DNA containing any one of the nucleotide sequences described in (i) to (iii) below;

(i) a nucleotide sequence of the nucleotides 52-1236 of the nucleotide sequence represented by SEQ ID NO:1 in which the nucleotides 562-564, "agc", are substituted by nucleotides representing a codon of an amino acid other than serine;

(ii) a nucleotide sequence of the nucleotides 52-1236 of the nucleotide sequence represented by SEQ ID NO:1 in which the nucleotides 571-573, "gcc", are substituted by nucleotides representing a codon of an amino acid other than alanine; or (iii) a nucleotide sequence of the nucleotides 52-1236 of the nucleotide sequence represented by SEQ ID NO:1 in which the nucleotides 562-564, "agc", are substituted by nucleotides representing a codon of an amino acid other than serine while the nucleotides 571-573 are substituted by nucleotides representing a codon of an amino acid other than alanine; or (1b) DNA which encodes a protein having α-galactosidase activity and which hybridizes with DNA composed of a nucleotide sequence complementary to DNA containing any one of the nucleotide sequences described in (i) to (iii) of (1a) above under stringent conditions, wherein nucleotides are the same as the nucleotides at the substituted site above at the corresponding position.

In the present invention, the term "codon" refers not to only the triple base linkage (triplet) of an RNA sequence after transcription but also the triple base linkage of a DNA sequence. Accordingly, codons in the case of a DNA sequence are denoted using thymine (T) instead of uracil (U).

The nucleotide sequence represented by SEQ ID NO:1 is a nucleotide sequence composed of 1,236 nucleotides encoding wild-type α-NAGA.

More specifically, the DNA described in (1a) above is DNA composed of a nucleotide sequence containing the nucleotides 52-1236 of the nucleotide sequence represented by SEQ ID NO:1 and excluding the nucleotides 1-51 that encodes a signal peptide of wild-type α-NAGA, in which nucleotides are replaced as described in (i) to (iii).

Here, a preferable example of the nucleotide sequence containing the nucleotides 52-1236 includes a nucleotide sequence in which a nucleotide sequence (polynucleotide) encoding a signal peptide is linked to the 5' side of the nucleotides 52-1236. The signal peptide is not limited as long as it allows the protein to pass through a cell membrane of an affected organ. For example, the signal peptide is preferably a signal peptide of a lysosomal enzyme such as wild-type α-NAGA or wild-type α-GAL, or a signal peptide of a secretase such as preprotrypsin, more preferably a signal peptide of wild-type α-NAGA or wild-type α-GAL, and still more preferably a signal peptide of wild-type α-GAL. A nucleotide sequence encoding the signal peptide of wild-type α-NAGA is a nucleotide sequence composed of the nucleotides 1-51 of the nucleotide sequence of wild-type α-NAGA represented by SEQ ID NO:1. A nucleotide sequence encoding the signal peptide of wild-type α-GAL is a nucleotide sequence composed of the nucleotides 1-93 of the nucleotide sequence of wild-type α-GAL represented by SEQ ID NO:9. A nucleotide sequence encoding the signal peptide of preprotrypsin is a nucleotide sequence represented by SEQ ID NO:11.

As the DNA described in (1a) above, DNA containing the nucleotide sequence described in (iii) is particularly preferable among the DNAs containing the nucleotide sequence described in (i), (ii) or (iii).

In addition, the DNA described in (1a) above is preferably DNA in which "the nucleotides representing a codon of an amino acid other than serine" described in (i) and (iii) are nucleotides representing a codon of glutamic acid or aspartic acid. Similarly, the DNA described in (1a) above is preferably DNA in which "the nucleotides representing a codon of an amino acid other than alanine" described in (ii) and (iii) are nucleotides representing a codon of one selected from the group consisting of leucine, valine, isoleucine, phenylalanine and methionine. Herein, regarding nucleotides representing a codon of each of the above amino acids (wherein the nucleotide at the left end is defined as the nucleotide at the 5' side), nucleotides representing a codon of glutamic acid are "gag" or "gaa" (preferably "gag"), and nucleotides representing a codon of aspartic acid are "gat" or "gac". Similarly, nucleotides representing a codon of leucine are "ctc", "ctt", "cta" or "ctg" (preferably "ctc"), nucleotides representing a codon of valine are "gtt", "gtc", "gta" or "gtg", nucleotides representing a codon of isoleucine are "att", "atc" or "ata", nucleotides representing a codon of phenylalanine are "ttt" or "ttc", and nucleotides representing a codon of methionine are "atg". Nucleotides representing a codon of serine include "agt" in addition to "agc" mentioned above, and nucleotides representing a codon of alanine include "gct", "gca" and "gcg" in addition to "gcc" mentioned above.

Furthermore, a particularly preferable DNA described in (1a) above is DNA in which "the nucleotides representing a codon of an amino acid other than serine" described in (i) to (iii) are nucleotides representing a codon of glutamic acid, and "the nucleotides representing a codon of an amino acid other than alanine" are nucleotides representing a codon of leucine. A preferable example of such DNA includes DNA composed of a nucleotide sequence (SEQ ID NO:3) in which the nucleotides 562-564 representing a codon of serine included in the nucleotide sequence of wild-type α-NAGA (SEQ ID NO:1) are substituted by nucleotides representing a codon of glutamic acid ("agc"→"gag"), and the nucleotides 571-573 representing a codon of alanine are substituted by nucleotides representing a codon of leucine ("gcc"→"ctc"). In this exemplification, the nucleotides 562-564 after the substitution may be nucleotides other than "gag" as long as they represent a codon of glutamic acid. Similarly, the nucleotides 571-573 after the substitution may be nucleotides other than "ctc" mentioned above as long as they represent a codon of leucine.

Such mutant DNA can be prepared in accordance with a site-directed mutagenesis method described in, for example, Molecular Cloning, A Laboratory Manual 2nd ed., Cold Spring Harbor Laboratory Press (1989), Current Protocols in Molecular Biology, John Wiley & Sons (1987-1997). Specifically, such DNA can be prepared by a known method such as a Kunkel method or a Gapped duplex method using a kit for introducing a mutation utilizing the site-directed mutagenesis method. Preferable examples of the kit include Quick-Change™ Site-Directed Mutagenesis Kit (manufactured by Stratagene), GeneTailor™ Site-Directed Mutagenesis System (manufactured by Invitrogen Corporation), and TaKaRa Site-Directed Mutagenesis System (e.g., Mutan-K or Mutan-Super Express Km: manufactured by Takara Bio Inc.).

Alternatively, as described in Examples below, such DNA can be prepared by performing PCR under appropriate conditions using PCR primers designed such that a missense mutation is introduced to give nucleotides representing a codon of a desired amino acid, and using, as a template, for example, DNA containing a nucleotide sequence encoding wild-type α-NAGA. A DNA polymerase used for the PCR is not limited, but a DNA polymerase with high accuracy is preferable. Preferable examples thereof include Pwo DNA (Polymerase Roche Diagnostics K.K.), Pfu DNA polymerase (Promega), platinum Pfx DNA polymerase (Invitrogen Corporation), KOD DNA polymerase (Toyobo Co., Ltd.) and KOD-plus-polymerase (Toyobo Co., Ltd.). Reaction conditions for the PCR can appropriately be determined in accordance with, for example, the optimum temperature of the DNA polymerase used, and the length and the type of DNA to be synthesized. For example, preferable conditions include a total of 20 to 200 cycles of "5 to 30 seconds at 90° C. to 98° C. (thermal denaturation and dissociation)→5 to 30 seconds at 50° C. to 65° C. (annealing) ∝330 to 1,200 seconds at 65° C. to 80° C. (synthesis and elongation)".

The DNA described in (1b) above can be obtained from a cDNA library or a genomic library by a known hybridization method such as colony hybridization, plaque hybridization or Southern blotting by using DNA containing any one of the nucleotide sequences described in any one of (i) to (iii) (i.e., DNA described in (1a)), DNA composed of a nucleotide sequence complementary to this DNA, or a fragment thereof as a probe. A library may be prepared by a known method, or a commercially available cDNA library or genomic library may be used. The library is not limited thereto.

As to a detailed procedure of the hybridization method, refer to, for example, Molecular Cloning, A Laboratory Manual 2nd ed. (Cold Spring Harbor Laboratory Press (1989)) as needed.

The term "stringent conditions" used upon performing a hybridization method refers to conditions during washing after hybridization, and specifically, a salt concentration of a buffer in the range of 15 to 330 mM and a temperature in the range of 25° C. to 65° C., and preferably, a salt concentration in the range of 15 to 150 mM and a temperature in the range of 45° C. to 55° C. More specifically, an example of the stringent conditions includes 80 mM at 50° C. In addition to the salt concentration, the temperature and the like, in consideration of other conditions such as the probe concentration, the length of the probe and the reaction time may also be considered to appropriately determine the conditions for obtaining the DNA described in (1b).

The DNA to be hybridized is a nucleotide sequence having a homology of preferably at least 40% or more, more preferably 60% or more, still more preferably 90% or more, particularly preferably 95% or more, and most preferably 99% or more relative to the nucleotide sequence of the DNA described in (1a) above.

Furthermore, in the DNA described in (1b) above, nucleotides are the same as the nucleotides at the substituted site above at the corresponding position.

Herein, the term "substituted site" refers to a site of the nucleotide substitution performed in the nucleotide sequences described in any one of (i) to (iii) contained in the DNA described in (1a) above. Specifically, the term refers to a site of nucleotides (triplet) representing a substituting codon caused by the nucleotide substitution. More specifically, the term "substituted site" refers to nucleotides corresponding to the positions of the nucleotides 562-564 of the nucleotide sequence represented by SEQ ID NO:1 (provided that the nucleotide sequences is limited to the nucleotide sequences described in (i) and (iii)), and nucleotides corresponding to the positions of the nucleotides 571-573 of the nucleotide sequence represented by SEQ ID NO:1 (provided that the nucleotide sequences is limited to the nucleotide sequences described in (ii) and (iii)) among the 1,185 nucleotides constituting the nucleotide sequences described in (i) to (iii). More specifically, the former nucleotides refer to the nucleotides 511-513 of the nucleotide sequences described in (i)

and (iii) above, and the latter nucleotides refer to the nucleotides 520-522 of the nucleotide sequences described in (ii) and (iii) above.

In addition, the "nucleotides" in the phrase "nucleotides corresponding to the nucleotides at the substituted site" refer to nucleotides (triplet) which are positioned to oppose nucleotides (triplet) complementary to the nucleotides at the substituted site in a hybrid prepared by hybridizing the DNA described in (1b) above with a strand complementary to the DNA described in (1a) above. For example, when the nucleotide sequence of the DNA described in (1b) above does not have a mutation such as deletion or addition, as compared with the DNA described in (1a) above (that is, when the lengths (the numbers of nucleotides) of both DNAs are the same), the nucleotides 511-513 and/or the nucleotides 520-522 of the nucleotide sequence of the DNA described in (1b) are the "nucleotides" in the phrase "nucleotides corresponding to the nucleotides at the substituted site".

It is important that the DNA described in (1b) above is DNA that encodes a protein having α-GAL activity. Therefore, for example, nucleotides representing a codon of an amino acid residue which is believed to be important for the binding performance (substrate-binding performance) with an α-galactose residue of a substrate of α-GAL and the catalytic reactivity to the substrate are preferably nucleotides that are not mutated (deleted, substituted or added) from the nucleotide sequences described in (i) to (iii) above. Preferable examples of such nucleotides of the nucleotide sequences described in (i) to (iii) include nucleotides corresponding to the positions of the nucleotides 82-93 (4 codons), 229-243 (5 codons), 349-381 (11 codons), 448-474 (9 codons), 574-576 (1 codon), 625-660 (12 codons) and 724-762 (13 codons) of the nucleotide sequence represented by SEQ ID NO:1 among the nucleotide sequences described in (i) to (iii). Among these nucleotides, nucleotides corresponding to the nucleotides 466-468 and 649-651, which represent codons of amino acid residues at catalytic sites, are particularly preferable.

Furthermore, in the DNA described in (1b) above, nucleotides representing a codon of an amino acid residue which is believed to be important for forming a homodimer are also preferably nucleotides that are not mutated (deleted, substituted or added) from the nucleotide sequences described in (i) to (iii). Preferable examples of such nucleotides of the nucleotide sequences described in (i) to (iii) include nucleotides corresponding to the positions of the nucleotides 133-135 and 1,048-1,050 of the nucleotide sequence represented by SEQ ID NO:1 among the nucleotide sequences described in (i) to (iii) above.

Furthermore, in the DNA described in (1b) above, nucleotides representing a codon of an amino acid residue as an N-type-sugar-chain-binding site are also preferably nucleotides that are not mutated (deleted, substituted or added) from the nucleotide sequences described in (i) to (iii) above. Preferable examples of such nucleotides of the nucleotide sequences described in (i) to (iii) above include nucleotides corresponding to the positions of the nucleotides 370-372, 529-531, 601-603, 1,075-1,077 and 1,153-1,155 of the nucleotide sequence represented by SEQ ID NO:1 among the nucleotide sequences described in (i) to (iii).

A particularly preferable example of the DNA described in (1b) above is DNA composed of a nucleotide sequence which is not completely identical to the nucleotide sequence of the DNA described in (1a) above but which is completely identical to the amino acid sequence after translation (i.e., DNA obtained by performing a silent mutation on the DNA described in (1a) above).

Preferable examples of a gene of the invention also include genes including DNA described in (2a) or (2b) below. Although the DNAs described in (2a) and (2b) are both preferably structural genes of the protein of the present invention, the gene including either of these DNAs is not limited thereto and it may consist of the DNA alone or it may contain the DNA together with other known nucleotide sequences required for gene expression (such as a transcriptional promoter, SD sequence, Kozak sequence and a terminator).

(2a) DNA containing any one of the nucleotide sequences described in (i) to (iii) below;

(i) a nucleotide sequence having the nucleotides 604-606, "agc", of the nucleotide sequence represented by SEQ ID NO:5 substituted by nucleotides representing a codon of an amino acid other than serine;

(ii) a nucleotide sequence having the nucleotides 613-615, "gcc", of the nucleotide sequence represented by SEQ ID NO:5 substituted by nucleotides representing a codon of an amino acid other than alanine; or (iii) a nucleotide sequence having the nucleotides 604-606, "agc", of the nucleotide sequence represented by SEQ ID NO:5 substituted by nucleotides representing a codon of an amino acid other than serine, and the nucleotides 613-615, "gcc", substituted by nucleotides representing a codon of an amino acid other than alanine; or (2b) DNA which encodes a protein having α-galactosidase activity and which hybridizes with DNA composed of a nucleotide sequence complementary to DNA containing a nucleotide sequences described in any one of (i) to (iii) of (2a) above under stringent conditions, wherein nucleotides are the same as the nucleotides at the substituted site above at the corresponding position.

The nucleotide sequence represented by SEQ ID NO:5 is a nucleotide sequence having the nucleotides 1-51 coding for a signal peptide moiety of a nucleotide sequence composed of 1,236 nucleotides encoding wild-type α-NAGA altered by a nucleotide sequence coding for a signal peptide moiety of wild-type α-GAL, namely, a nucleotide sequence coding for a so-called fusion protein. Here, the nucleotide sequence coding for the signal peptide moiety of the wild-type α-GAL, as already described above, is a sequence of nucleotides 1-93 of the nucleotide sequence coding for wild-type α-GAL represented by SEQ ID NO:9.

As the DNA described in (2a), DNA containing the nucleotide sequence described in (iii) is particularly preferable among the DNAs containing the nucleotide sequence described in (i), (ii) or (iii).

In addition, a preferable example of the DNA described in (2a) above includes DNA in which "the nucleotides representing a codon of an amino acid other than serine" described in (i) and (iii) are nucleotides representing a codon of glutamic acid or aspartic acid. Similarly, a preferable example of the DNA described in (2a) above also includes DNA in which "the nucleotides representing a codon of an amino acid other than alanine" described in (ii) and (iii) are nucleotides representing a codon of one selected from the group consisting of leucine, valine, isoleucine, phenylalanine and methionine. Herein, the explanation for the DNA described in (1a) above similarly applies to the nucleotides representing a codon of each of the above amino acids.

Furthermore, a particularly preferable example of the DNA described in (2a) above includes DNA in which "the nucleotides representing a codon of an amino acid other than serine" described in (i) to (iii) are nucleotides representing a codon of glutamic acid, and "the nucleotides representing a codon of an amino acid other than alanine" are nucleotides representing a codon of leucine. A preferable example of such DNA is DNA composed of a nucleotide sequence (SEQ ID NO:7) in which the nucleotides 604-606 representing a codon of serine are substituted by nucleotides representing a codon of glutamic acid ("agc"→"gag"), and the nucleotides 613-615 representing a codon of alanine are substituted by nucleotides representing a codon of leucine ("gcc"→"ctc") in the nucleotide sequence represented by SEQ ID NO:5. In this exemplification, the nucleotides 604-606 after the substitution are not limited and may be nucleotides other than "gag" mentioned above as long as they represent a codon of glutamic acid. Similarly, the nucleotides 613-615 after the substitution are not limited and may be nucleotides other than "ctc" mentioned above as long as they represent a codon of leucine.

As to preparation of such substituted-type DNA mutant, the explanation for the DNA described in (1a) above similarly applies.

The DNA described in (2b) above can be obtained from a cDNA library or a genomic library by a known hybridization method by using DNA containing the nucleotide sequence described in any one of (i) to (iii) (i.e., DNA described in (2a)), DNA composed of a nucleotide sequence complementary to this DNA, or a fragment thereof as a probe. As to the type, procedure and conditions of the hybridization as well as each library, the explanation for the DNA described in (1a) above similarly applies.

The DNA to be hybridized has a nucleotide sequence having a homology of preferably at least 40% or more, more preferably 60% or more, still more preferably 90% or more, particularly preferably 95% or more, and most preferably 99% or more to the nucleotide sequence of the DNA described in (2a) above.

Furthermore, in the DNA described in (2b) above, nucleotides are the same as the nucleotides at the substituted site above at the corresponding position.

Herein, the term "substituted site" refers to a site of the nucleotide substitution performed in any one of the nucleotide sequences described in (i) to (iii) contained in the DNA described in (2a) above. Specifically, the term refers to a site of nucleotides (triplet) representing an altered codon resulting from the nucleotide substitution. More specifically, the term "substituted site" refers to the nucleotides 604-606 (provided that the nucleotide sequence is limited to the nucleotide sequences described in (i) and (iii)), and the nucleotides 613-615 (provided that the nucleotide sequence is limited to the nucleotide sequences described in (ii) and (iii)) among the 1,275 nucleotides constituting the nucleotide sequences described in (i) to (iii).

In addition, the "nucleotides" in the phrase "nucleotides corresponding to the nucleotides at the substituted site" refer to nucleotides (triplet) which are positioned to oppose nucleotides (triplet) complementary to the nucleotides at the substituted site in a hybrid prepared by hybridizing the DNA described in (2b) above with a strand complementary to the DNA described in (2a) above. For example, when the nucleotide sequence of the DNA described in (2b) above does not have a mutation such as deletion or addition, as compared to the DNA described in (2a) above (that is, when the lengths (the numbers of nucleotides) of both DNAs are the same), the nucleotides 604-606 and/or the nucleotides 613-615 of the nucleotide sequence of the DNA described in (2b) are the "nucleotides" in the phrase "nucleotides corresponding to the nucleotides at the substituted site".

It is important that the DNA described in (2b) above is DNA that encodes a protein having α-GAL activity. Therefore, for example, nucleotides representing a codon of an amino acid residue which is believed to be important for the binding performance (substrate-binding performance) with an α-galactose residue of a substrate of α-GAL and the catalytic reactivity to the substrate are preferably nucleotides that are not mutated (deleted, substituted or added) from the nucleotide sequences described in (i) to (iii). Preferable examples of such nucleotides of the nucleotide sequences described in (i) to (iii) include the nucleotides 124-135 (4 codons), 271-285 (5 codons), 391-423 (11 codons), 490-516 (9 codons), 616-618 (1 codon), 667-702 (12 codons) and 766-804 (13 codons) among the nucleotide sequences described in (i) to (iii) above. Among these nucleotides, the nucleotides 508-510 and 691-693, which represent codons of amino acid residues at a catalytic site, are particularly preferable.

Furthermore, in the DNA described in (2b) above, nucleotides representing a codon of an amino acid residue which is believed to be important for forming a homodimer are also preferably not mutated (deleted, substituted or added) from the nucleotide sequences described in (i) to (iii). Preferable examples of such nucleotides of the nucleotide sequences described in (i) to (iii) include the nucleotides 175-177 and 1,090-1,092 among the nucleotide sequences.

Furthermore, in the DNA described in (2b) above, nucleotides representing a codon of an amino acid residue as an N-type-sugar-chain-binding site are also preferably not mutated (deleted, substituted or added) from the nucleotide sequences described in (i) to (iii) above. Preferable examples of such nucleotides of the nucleotide sequences described in (i) to (iii) above include the nucleotides 412-414, 571-573, 643-645, 1,117-1,119 and 1,195-1,197 among the nucleotide sequences.

A particularly preferable example of the DNA described in (2b) above is DNA composed of a nucleotide sequence which is not completely identical to the nucleotide sequence of the DNA described in (2a) above but which is completely identical to the amino acid sequence after translation (i.e., DNA obtained by performing a silent mutation on the DNA described in (2a) above).

Regarding the above-described gene encoding the protein of the present invention, codons corresponding to each of the amino acids after translation are not particularly limited. Accordingly, the gene encoding the protein of the present invention may contain DNA representing codons which are generally used (preferably, codons whose frequency of use is high) in a mammal such as human after transcription, or DNA representing codons which are generally used (preferably, codons whose frequency of use is high) in, for example, a microorganism such as *E. coli* or yeast or a plant after transcription.

4. RECOMBINANT VECTOR AND TRANSFORMANT

Generally, in order to express the protein of the present invention, first, a recombinant vector is constructed by introducing the above-described gene of the present invention into an expression vector. In this step, as needed, a transcriptional promoter, SD sequence (in the case where a host is a prokaryotic cell) and Kozak sequence (in the case where a host is a eukaryotic cell) may be linked upstream of the gene to be incorporated into the expression vector, in advance. Alternatively, a terminator may be linked downstream from the gene in advance. Furthermore, an enhancer, a splicing signal, a poly-A addition signal, a selective marker and the like may also be linked in advance. The above elements, such as a transcriptional promoter, required for expressing a gene may be contained in the gene from the beginning. In the case where these elements are contained in the expression vector from the beginning, they may be utilized. The usage embodiments of the elements are not particularly limited.

As a method of incorporating the gene into an expression vector, various types of methods using a known gene recombination technique, for example, a method using a restriction enzyme or a method using a topoisomerase, can be employed. The expression vector is not limited as long as it can retain a gene encoding a protein of the present invention, examples being plasmid DNA, bacteriophage DNA, retrotransposon DNA, a retrovirus vector and artificial chromosome DNA. A vector suitable for a host cell used can appropriately be selected and used.

Subsequently, the constructed recombinant vector is introduced into a host to obtain a transformant, and the transformant is cultured. Thus, the protein of the present invention can be expressed. The term "transformant" used in the present invention refers to a product resulting from introduction of a foreign gene into a host. For example, the transformant includes a product in which a foreign gene is introduced by introducing plasmid DNA or the like into a host (transformation) and a product in which a foreign gene is introduced by infecting a host with a virus or a phage (transduction).

The host is not limited as long as the host can express a protein of the present invention after introduction of the recombinant vector, and can appropriately be selected. Examples of the host include known hosts such as animal cells, e.g., a human cell and a mouse cell, plant cells, bacteria, yeast and the like.

Where an animal cell is used as a host, for example, a human fibroblast, a CHO cell, a simian COS-7 cell, Vero, a mouse L cell, a rat GH3, or a human FL cell is used. Alternatively, insect cells such as an Sf9 cell or an Sf21 cell can also be used.

Where a bacterium is used as a host, for example, *E. coli* or *Bacillus subtilis* is used.

Where yeast is used as a host, for example, *Saccharomyces cerevisiae* or *Schizosaccharomyces pombe* is used.

Where a plant cell is used as a host, for example, a tobacco BY-2 cell is used.

The method of obtaining a transformant is not limited and can appropriately be selected in consideration of the combination of the types of a host and an expression vector used. Preferable examples of the method include an electroporation method, a lipofection method, a heat shock method, a PEG method, a calcium phosphate method, a DEAE-dextran method, and a method of infecting a virus such as a DNA virus or an RNA virus.

In the resulting transformant, the codon type of a gene contained in the recombinant vector is not limited. The codon type may be identical to or different from the codon type of a host actually used.

5. METHOD OF PRODUCING PROTEIN

A protein of the present invention (a protein having α-GAL activity) can be produced, for example, by altering the structure of the active site (in particular, the substrate-binding site) of wild-type α-NAGA so that a substrate of α-GAL can bind thereto. If the substrate of α-GAL can bind to the active site, the substrate can be hydrolyzed via catalysis by the catalytic site of wild-type α-NAGA.

Such a structural alteration is performed as follows. For example, as described above, in the amino acid sequence constituting the active site (substrate-binding site) of wild-type α-NAGA, (i) the 188th serine is substituted by another amino acid such as glutamic acid or aspartic acid, (ii) the 191st alanine is substituted by another amino acid such as leucine, valine, isoleucine, phenylalanine or methionine, or (iii) both the 188th serine and the 191st alanine are substituted as described in (i) and (ii) above by a gene recombination technique. The structural alteration can be achieved by making the structure of the side chain(s) of the amino acid(s) after the replacement from that before the replacement. Consequently, the substrate specificity of wild-type α-NAGA can be altered. In particular, the above-described structural alteration is preferably performed by substituting the 188th serine with glutamic acid and the 191st alanine with leucine. Thereby, the substrate specificity of α-GAL can be imparted to α-NAGA. In the above structural alteration, an amino acid substitution that brings about a significant structural alteration is the substitution of the 191st alanine with leucine or the like. More specifically, the side chain of the amino acid 191 is altered from "—$CH_3$", i.e., the side chain of alanine, to a bulky side chain, such as "—$CH_2$—$CH(CH_3)$—$CH_3$", i.e., the side chain of leucine. As a result, the space of the active site where the N-acetyl group in a substrate of α-NAGA is to be incorporated is restricted, thereby reducing the binding performance of the protein with the substrate. Instead, the binding performance with a substrate of α-GAL is increased accordingly.

The above-described method for producing a protein of the invention may be carried out, without limitation, by using wild-type α-NAGA containing the signal peptide from wild-type α-GAL, as the wild-type α-NAGA to be subjected to structural alteration, or the method may be carried out via a step of adding (binding) a signal peptide from wild-type α-GAL to an α-NAGA mutant obtained by structural alteration or, if the α-NAGA mutant includes a signal peptide of wild-type α-NAGA, via a step of replacing this signal peptide with a signal peptide from wild-type α-GAL.

Hence, a preferable example of a method for producing the protein of the invention includes a method for producing a protein having α-GAL activity, comprising altering the structure of the active site of wild-type human α-N-acetylgalactosaminidase including a signal peptide from wild-type human α-galactosidase such that a substrate of α-galactosidase can bind thereto.

Moreover, a preferable example of a method for producing the protein of the invention also includes a method for producing a protein having α-GAL activity, comprising adding (binding) a signal peptide from wild-type α-GAL to a protein having the structure of the active site of wild-type α-NAGA altered such that an α-GAL substrate can bind thereto, or comprising replacing a signal peptide moiety of a protein having the structure of the active site of wild-type α-NAGA altered such that an α-GAL substrate can bind thereto with a signal peptide from wild-type α-GAL.

The above-mentioned replacement of the signal peptide moiety may be carried out according to a conventional gene recombination technique by using known nucleotide sequence information and amino acid sequence information on wild-type α-NAGA and wild-type α-GAL.

The protein of the present invention can be produced specifically by a method including a step of culturing the above-described transformant and a step of collecting a protein having α-galactosidase activity from the resulting cultured product. Herein, the term "cultured product" refers to all of a culture supernatant, cultured cells, cultured bacteria, cell debris and bacterial debris. The cultivation of the transformant can be performed in accordance with a general method used for culturing a host. The target protein is accumulated within the cultured product.

As a medium used for the cultivation, any known natural or synthetic medium may be used as long as it contains a carbon source, a nitrogen source, inorganic salts and the like that can be utilized by the host, and as long as the transformant can be cultured efficiently.

In order to prevent loss of a recombinant vector contained in the transformant and loss of a gene encoding a target protein, the cultivation may be performed under a selection pressure. Specifically, in the case where a selective marker is a drug-resistance gene, a corresponding drug can be added to the medium. In the case where a selective marker is an auxotrophic complementary gene, a corresponding nutritional factor can be removed from the medium. For example, in the case where a human fibroblast transduced with a vector containing the G418-resistant gene is cultured, G418 (G418 sulfate) may be added during cultivation, as needed.

In the case where a transformant or the like transformed with an expression vector using an inducible promoter as a promoter is cultured, a favorable inducer (for example, IPTG) may be added to the medium, as needed.

The conditions for culturing the transformant are not particularly limited as long as productivity of the target protein and growth of the host are not interfered. In general, the culture is performed at a temperature in the range of 10° C. to 40° C., and preferably in the range of 20° C. to 37° C. for 5 to 100 hours. The pH can be adjusted using an inorganic or organic acid, an alkaline solution, or the like. Examples of the culture method include solid culture, static culture, shaking culture and aeration-agitation culture.

Once the target protein is produced in bacteria or in cells at the end of cultivation, the target protein can be collected by disrupting the bacteria or the cells. As a method of disrupting the bacteria or the cells, for example, a high-pressure treatment using a French press or a homogenizer, an ultrasonic treatment, a milling treatment using glass beads or the like, an enzyme treatment using lysozyme, cellulase, pectinase, or the like, a freeze-thawing treatment, a treatment with a hypotonic solution, or a bacteriolysis-inducing treatment using a phage can be employed. After the disruption, the disruption residue (which contains an insoluble fraction of a cell extract) of the bacteria or the cells can be removed, as needed. Examples of the method of removing the residue include centrifugal separation and filtration. The efficiency of the removal of residue can be increased using, for example, a flocculant or a filter aid, as needed. The supernatant obtained after the removal of the residue is a soluble fraction of the cell extract, and can be used as a crude protein solution.

When the target protein is produced in bacteria or in cells, alternatively, the bacteria of the cells themselves may be collected by centrifugal separation, membrane separation or the like, and used undisrupted.

On the other hand, when the target protein is produced outside the bacteria or outside the cells, the medium is used directly, or the bacteria or the cells are removed by centrifugal separation, filtration or the like. Subsequently, the target protein is collected from the cultured product by extraction through ammonium sulfate precipitation, as needed, and further isolated and purified by dialysis and chromatography (such as gel filtration, ion-exchange chromatography or affinity chromatography).

When the target protein is produced by using bacteria or cells (in or outside the bacteria or cells) as described above, the signal peptide moiety is generally removed upon transportation from the endoplasmic reticulum inside the bacteria or cells to the cytoplasm or upon secretion outside the bacteria or cells, leaving a mature protein to be collected without the signal peptide moiety. The present invention, however, is not limited thereto, and, for example, a protein having two or more (consecutive) signal peptide moieties required for the transportation from the endoplasmic reticulum to the cytoplasm or for the secretion outside the bacteria or cells may be expressed so that a protein having at least one signal peptide moiety left after the transportation or secretion is collected. In this case, if the resulting target protein should be used as an active element of a pharmaceutical composition or the like, the signal peptide moiety may, for example, be cleaved or broken down with an enzyme to use the protein in a form of a mature protein.

The production yield of a protein obtained by culturing a transformant or the like can be determined, for example, by SDS-PAGE (polyacrylamide gel electrophoresis) in terms of unit per culture solution, per wet weight or dry weight of bacteria, per protein in a crude enzyme solution, or the like.

In addition to the protein synthesis system using a transformant described above, a target protein can be produced by using a cell-free protein synthesis system in which no living cells are used.

The cell-free protein synthesis system is a system in which a target protein is synthesized in an artificial container such as a test tube using a cell extract. A cell-free protein synthesis system which can be used also includes a cell-free transcription system in which RNA is synthesized using DNA as a template.

In this case, the cell extract used is preferably derived from the host cell described above. Examples of the cell extract that can be used include extracts derived from eukaryotic cells and prokaryotic cells, more specifically, extracts of a CHO cell, a rabbit reticulocyte, a mouse L-cell, a HeLa cell, wheat germ, budding yeast or *E. coli*. The cell extract may be, without limitation, concentrated or diluted upon use, or they may be used without further treatment.

The cell extract can be obtained, for example, by ultrafiltration, dialysis or polyethylene glycol (PEG) precipitation.

Alternatively, such cell-free protein synthesis can be performed using a commercially available kit. Examples of the kit include a reagent kit PROTEIOS™ (Toyobo Co., Ltd.), TNT™ System (Promega), a synthesis device PG-Mate™ (Toyobo Co., Ltd.) and RTS (Roche Diagnostics K.K.).

The target protein produced by cell-free protein synthesis can be purified as described above by appropriately selecting means such as chromatography.

6. PHARMACEUTICAL COMPOSITION FOR TREATING FABRY DISEASE (i) Pharmaceutical Composition as Enzyme Agent Used for Enzyme Replacement or the Like As described above, the protein of the present invention can exert various excellent effects regarding the treatment of Fabry disease, and thus can preferably be used as an active element of a pharmaceutical composition for treating Fabry disease (a therapeutic agent for Fabry disease). In other words, the present invention provides a pharmaceutical composition for treating Fabry disease comprising the above-described protein of the present invention. Preferably, the pharmaceutical composition is specifically in a form of an enzyme agent that can be used for enzyme replacement therapy.

The protein of the present invention, which serves as an active element in the pharmaceutical composition, may be used, without limitation, in the form of a salt, a hydrate or the like, as needed, or in an appropriately chemically-modified state in consideration of storage stability (particularly for maintaining enzymatic activity) as a therapeutic agent.

The pharmaceutical composition may contain components other than the protein of the present invention. Examples of the other components include various types of pharmaceutically acceptable components (such as various types of pharmacologically acceptable carriers) that are required in accordance with the usage (the usage embodiment) of the pharmaceutical composition. The other components can appropriately be contained such that the effects achieved by the protein of the present invention and the like are not impaired.

In the case where the pharmaceutical composition is used as an enzyme agent for enzyme replacement, the mixing ratio of the protein of the present invention, and the types and mixing ratios of other components used can appropriately be determined in accordance with a method for preparing a known enzyme agent for enzyme replacement (in particular, an enzyme agent used for enzyme replacement therapy for Fabry disease).

The method of administrating the pharmaceutical composition is not limited. When the pharmaceutical composition is an enzyme agent used for enzyme replacement, parenteral administration such as intravenous drip is generally used. A pharmaceutical preparation that can be used in various administration methods such as parenteral administration may be prepared by appropriately selecting and using an excipient, a filler, an extender, a binder, a humectant, a disintegrant, a lubricant, a surfactant, a dispersant, a buffer, a preservative, a solubilizer, an antiseptic, a flavoring agent, a soothing agent, a stabilizing agent, an isotonizing agent or the like, all of which are generally used in the production of medicine according to a routine method.

The form of the pharmaceutical composition is not limited. When the pharmaceutical composition is an enzyme agent used for enzyme replacement, an intravenous injection (including drip infusion) is generally used. For example, the pharmaceutical composition can be provided in the form of, for example, a single-dose ampule or a multi-dose container.

In general, the dosage of the pharmaceutical composition can appropriately be determined in a wide range by considering the mixing ratio of the active element in the pharmaceutical preparation as well as the age and body weight of the subject (patient) to be administered with the pharmaceutical composition, the type, condition and the like of the disease, in addition to the administration route, the number of administrations, the term of administration, and the like. In particular, in the case where the pharmaceutical composition is an enzyme agent used for enzyme replacement, the number of doses is preferably about one in every two to four weeks, while the amount thereof per dose is such that the protein or the like (recombinant enzyme) of the present invention, as an active element, is administered, for example, for preferably about 0.1 to 10 mg/kg, more preferably about 0.1 to 5 mg/kg, and still more preferably about 0.2 to 1 mg/kg relative to the body weight of a patient.

In the present invention, the protein (recombinant enzyme) of the present invention, which serves as an active element, is excellent in stability in blood and the uptake efficiency thereof by a cell of an affected organ is high. Therefore, even when the protein is used in a smaller amount than a conventional protein, the effect of enzyme replacement can be the same as or stronger than that achieved with the conventional protein. In addition, since allergic side effects are negligible, physical, mental and economical burdens on patients can be markedly reduced.

(ii) Pharmaceutical Composition as Gene Therapeutic Agent

As described above, the gene of the present invention encodes a protein of the present invention which can produce various excellent effects regarding the treatment of Fabry disease, and thus can be used as an active element of a pharmaceutical composition for treating Fabry disease (a therapeutic agent for Fabry disease (a gene therapeutic agent)). That is, the present invention provides a pharmaceutical composition for treating Fabry disease, comprising the above-described gene of the present invention.

In the case where the pharmaceutical composition is used as a gene therapeutic agent, a method in which the gene is directly administered by injection, or a method in which a vector incorporating a nucleic acid is administered, may be employed. Examples of the vector include an adenovirus vector, an adeno-associated virus vector, a herpesvirus vector, a vaccinia virus vector, a retrovirus vector and a lentivirus vector. By using these virus vectors, the gene therapeutic agent can be administered efficiency. A commercially available gene transfer kit (for example, product name: AdenoExpress, manufactured by Clontech) can also be used.

In addition, in the case where the pharmaceutical composition is used as a gene therapeutic agent, the composition may be introduced into a phospholipid endoplasmic reticulum such as liposome, and the endoplasmic reticulum may be administered. Specifically, an endoplasmic reticulum retaining a gene of the present invention is introduced into a predetermined cell by a lipofection method. The resulting cell is then administered, for example, intravenously or intra-arterially. Alternatively, such a cell can be locally administered to an organ affected by Fabry disease. For example, in the case where the pharmaceutical composition is administered to an adult, the dose is preferably about 0.1 μg/kg to 1,000 mg/kg, and more preferably about 1 μg/kg to 100 mg/kg per day relative to the body weight of the patient.

7. METHOD OF TREATING FABRY DISEASE

The present invention comprises a method of treating Fabry disease, comprising administering the pharmaceutical composition of the invention to a Fabry disease patient. The present invention also comprises the use of the pharmaceutical composition of the invention for treating Fabry disease, and the use of the pharmaceutical composition or the protein of the present invention for producing a drug for treating Fabry disease.

The pharmaceutical composition used in the therapeutic method of the present invention may be a pharmaceutical composition containing a protein of the present invention ("section 6 (i)" above), a pharmaceutical composition containing a gene of the present invention ("section 6 (ii)" above), or a combination of these pharmaceutical compositions, which may be appropriately selected, without limitation, in consideration of the state of the patient, the presence or absence of adverse side effects, the administration effect and the like. Here, each of the pharmaceutical compositions to be administered to a Fabry disease patient is preferably administered in the usage embodiment as an enzyme agent for enzyme replacement or as a gene therapeutic agent described above.

In particular, when the pharmaceutical compositions are used in combination as described above, for example, the proportion of dosage, the number of doses and the term of administration of each of the pharmaceutical compositions can appropriately be determined to suit each patient. For example, a preferable method and dosage for administration of each of the pharmaceutical compositions and the like are as described above.

The present invention will now be described more specifically by means of Examples, but the present invention is not limited thereto.

EXAMPLE 1

Selection of Mutation Site to be Introduced into α-N-Acetylgalactosaminidase (α-NAGA)

In order to design a novel enzyme in which the substrate specificity of human α-NAGA is altered by a substrate specificity similar to that of human α-GAL, mutation sites (position of amino acids) to be introduced into human α-NAGA were determined by comparison and study using three-dimensional structure models of the proteins. The procedure and results of the determination are specifically described below.

1. Data Used

The amino acid sequence data of human α-NAGA and human α-GAL registered with Swiss-Prot as shown below were used (see Table 1).

The three-dimensional structure data of chicken α-NAGA and human α-GAL proteins registered with Protein Data Bank (PDB) as shown below were used (see Table 2).

(1) Amino Acid Sequence Data
Used data base: Swiss-Prot

TABLE 1

| | entry name | accession number |
|---|---|---|
| Human α-NAGA | NAGAB_HUMAN | P17050 |
| Human α-GAL | AGAL_HUMAN | P06280 |

(2) Protein Three-Dimensional Structure Data
Used data base: Protein Data Bank (PDB)

TABLE 2

| | PDB ID |
|---|---|
| Chicken α-NAGA | 1KTC (see *1 below) |
| Human α-GAL | 1R47 (see *2 below) |

*1: Garman S C et al., Structure (Camb), 2002, 10(3): 425-34.
*2: Garman S C et al., J. Mol. Biol., 2004, 19; 337(2): 319-35.

2. Construction of Three-Dimensional Structure Model of Human α-NAGA

A three-dimensional structure model of human α-NAGA was constructed based on the structure of chicken α-NAGA by using an existing method, a homology modeling method (see Sutcliffe M J et al., Prot. Eng., 1987, 1, 377-84; and Sutcliffe M J et al., Prot. Eng., 1987, 1, 385-92). The structure of chicken α-NAGA (substrate complex) registered with PDB was used as a structure of a template used for homology modeling. The degree of matching (identity) of amino acids between human α-NAGA and chicken α-NAGA is 75%, which satisfies the condition (identity ≥30%) for constructing a structural model by the homology modeling method. The construction of a structural model by the homology modeling method was performed using existing software MODELLER (available through access to MODELLER CBSU Web). Furthermore, a model of a substrate complex of human α-NAGA was constructed by adapting a substrate bound to chicken α-NAGA into the constructed structural model of human α-NAGA in accordance with the position of the substrate.

3. Comparison of Three-Dimensional Structures Contributing to Substrate Specificity of Human α-GAL and that of Human α-NAGA The three-dimensional structure of human α-NAGA is similar to that of human α-GAL, and catalytic domains of both human α-NAGA and human α-GAL have a $(\beta\alpha)_8$-barrel structure. Amino acid residues (catalytic residues) required for catalytic action present in the active sites (including a catalytic site and a substrate-binding site) are localized at the C-terminal side of each strand of the $(\beta\alpha)_8$-barrel structure. In FIGS. 1, 2A and 2B, the three-dimensional structures of human α-NAGA and human α-GAL are shown as a ribbon model, and amino acid residues at the catalytic sites and the substrate-binding site in each of the structure are shown as a stick model. In order to compare the positional relationships between the substrate and the residues at the catalytic site and the substrate-binding site in the structure, the structure of α-NAGA was superimposed on the structure of α-GAL by the superimposing method developed by Kabsch (see Kabsch W. et al., Acta Crystallogr; 1976: A32, 827-828; and Kabsch W. et al., Acta Crystallogr; 1978: A34, 922-923). Subsequently, in the structural model of human α-NAGA, amino acid residues involved in the binding of the substrate were selected by extracting amino acid residues adjacent to the substrate. The results are shown in Table 3. The right column of Table 3 shows 14 amino acid residues selected from human α-NAGA, and the left column shows amino acid residues in human α-GAL which positionally correspond to those 14 amino acid residues.

TABLE 3

| Human α-GAL | Human α-NAGA |
|---|---|
| Trp47 | Trp33 |
| Asp92 | Asp78 |
| Asp93 | Asp79 |
| Tyr134 | Tyr119 |
| Cys142 | Cys127 |
| Lys168 | Lys154 |
| Asp170 (*) | Asp156 (*) |
| Cys172 | Cys158 |
| Glu203 | Ser188 |
| Leu206 | Ala191 |
| Tyr207 | Tyr192 |
| Arg227 | Arg213 |
| Asp231 (*) | Asp217 (*) |
| Asp266 | Asp252 |

(*) catalytic residue

These amino acid residues were compared with each other by superimposing the structure of human α-NAGA on that of human α-GAL to detect residues that were identical to each other and residues that were different from each other, thereby defining similarity and difference between the amino acid sequences of human α-GAL and human α-NAGA.

4. Similarity Between Human α-GAL and Human α-NAGA

Figure 2C:
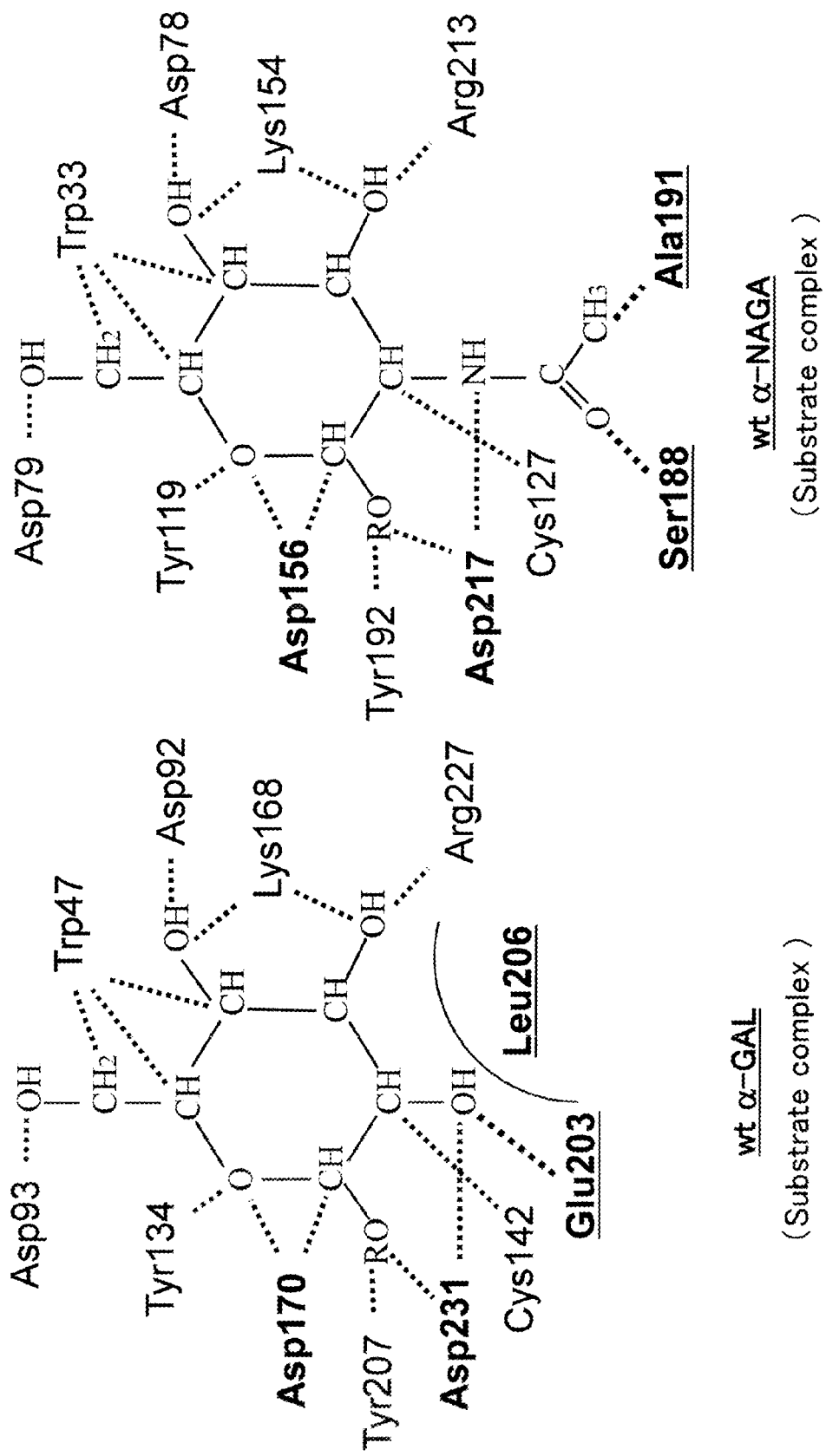
FIG. 2C gives diagrams showing the interaction sites between the amino acids constituting the active site of wild-type α-GAL or wild-type α-NAGA and the substrate thereof.

As a result, it was found that among the 14 extracted residues, 12 residues including Asp156 and Asp217 as the catalytic sites of human α-NAGA, were identical between α-NAGA and α-GAL. Atom positions of these amino acid residues were also satisfactorily superimposed with each other, and thus, it was confirmed that the atom positions of these amino acid residues in the structures were strictly similar to each other. FIG. 2A shows positions of the amino acid residues common to α-NAGA and α-GAL in the three-dimensional structures. FIG. 2C shows the interaction between each of the amino acid residues and the substrate. It is believed that all of these residues are involved with the substrate via a hydrogen bond or a hydrophobic bond. Note that, in FIG. 2C, the amino acids which are not underlined are amino acids common to α-NAGA and α-GAL, and the underlined amino acids are amino acids different between α-NAGA and α-GAL.

5. Difference Between Human α-GAL and Human α-NAGA

There are two residues which are different between human α-GAL and human α-NAGA (see FIG. 2C). In α-GAL, the amino acid residues corresponding to Ser188 and Ala191 of α-NAGA are Glu203 and Leu206, respectively. FIG. 2B shows positions of the amino acid residues which are different between α-NAGA and α-GAL in the three-dimensional structure.

As shown in FIG. 2C, in α-GAL, the carbon atom at the 2-position of the sugar (six-membered ring) in the substrate of α-GAL or α-NAGA, was bound by an "—OH group (a hydroxyl group)" or an "—NH—C(CH$_3$)=O group (an N-acetyl group)", respectively.

In α-NAGA, the hydroxyl group of the side chain of Ser188 is presumably bound to the oxygen atom of the N-acetyl group in the substrate via a hydrogen bond, and the methyl group of the side chain of Ala191 is presumably bound to the methyl group of the N-acetyl group in the substrate via a hydrophobic bond. Based on these presumptions, it was believed that Ser188 and Ala191 of α-NAGA are important residues for recognizing the N-acetyl group in the substrate.

On the other hand, it has been reported that, in human α-GAL, Glu203 and Leu206, which are different from the corresponding residues of α-NAGA, are important for recognizing a substrate of α-GAL (Garman S C et al., J. Mol. Biol., 2004, 19; 337(2): 319-35). Furthermore, it has been found by an X-ray crystal structure analysis that the carboxyl group of the side chain of Glu203 of α-GAL forms a hydrogen bond with the hydroxyl group of the substrate. In addition, Leu206 of α-GAL is a residue having a bulky side chain, and occupies a part of the space of the substrate-binding site of α-GAL. On the other hand, the hydroxyl group (at the 2-position) in the substrate of α-GAL is a functional group which is not bulky. It is obvious that the hydroxyl group is smaller than, for example, the N-acetyl group in the substrate of α-NAGA. Accordingly, it is believed that, in the binding between α-GAL and the substrate, the size of the space of the substrate-binding site of α-GAL is suitable for the size of the hydroxyl group in the substrate of α-GAL. Accordingly, in α-GAL, two residues, Glu203 and Leu206, appeared to contribute to the strength of the substrate specificity.

6. Verification of Substrate Specificity with Three-Dimensional Structure Models Furthermore, in order to verify the interaction of α-NAGA with the substrate and the interaction of α-GAL with the substrate, structural models in which the substrates were exchanged with each other, that is, (i) a complex model combining the substrate of α-GAL with α-NAGA, and (ii) a complex model combining the substrate of α-NAGA with α-GAL, were constructed to examine the influence of the two residues which are different between α-NAGA and α-GAL on the substrates.

According to the results, in the complex model in which the substrate of α-GAL was docked into the α-NAGA structure model, the side chain of Ser188 of α-NAGA did not interact with the hydroxyl group at the 2-position of the substrate of α-GAL. In addition, a clearance space was formed between Ala191 and the substrate of α-GAL, and thus, interaction with the hydroxyl group was not observed. On the other hand, in the complex model in which the substrate of α-NAGA was docked into the α-GAL structure, it was confirmed that the N-acetyl group at the 2-position of the substrate of α-NAGA collides against Glu203 and Leu206 of α-GAL. Consequently, it was predicted that binding of the substrate was blocked by the presence of these two residues.

These predicted results supported the experimental results described above. Thus, it was supported that Ser188 and Ala191 of α-NAGA and Glu203 and Leu206 of α-GAL were important for the substrate specificity of α-NAGA and α-GAL, respectively.

7. Amino-Acid Residue Substitution for Modifying Substrate Specificity of Human α-NAGA to Substrate Specificity Similar to That of Human α-GAL As described above, the amino acid sequences between human α-GAL and human α-NAGA are completely identical including the catalytic site, except for the two residues which recognize the functional group bound to the carbon atom at the 2-position of the sugar (six-membered ring) in each of the substrates. This indicates the possibility of maintaining the catalytic activity as it is before substitution while altering only the substrate specificity from α-NAGA specific to α-GAL specific or vice versa by substituting these two residues that highly contribute to the substrate specificity. In order to alter the substrate specificity of human α-NAGA to express α-GAL activity, an amino-acid substitution at these two positions is important. By substituting Ser188 of human α-NAGA by Glu, the recognition of the N-acetyl group of the substrate of α-NAGA via a hydrogen bond can be canceled, and instead an interaction with a hydroxyl group of the substrate of α-GAL via a hydrogen bond can be introduced. Furthermore, by replacing Ala191 of human α-NAGA by Leu, the space in which an N-acetyl group is to be incorporated upon binding of a substrate of α-NAGA will be occupied by the bulky side chain of Leu, and this steric hindrance inhibits binding of the substrate. It was expected that, in α-NAGA, these effects would cancel the original recognition of a substrate of α-NAGA and would result a high specificity with a substrate of α-GAL.

8. Evaluation of Human α-NAGA Amino-Acid Substitution Model

In order to confirm the effect of substituting Ser188 and Ala191 of α-NAGA by Glu and Leu, respectively, on the adjacent structure, an α-NAGA mutant (α-NAGA (S188E/A191L)) model was constructed, and the three-dimensional structure of the α-NAGA mutant model was compared with that of wild α-NAGA. As a result, it was confirmed that the above substitutions did not affect the conformation composed of the adjacent amino acid residues. Accordingly, it was supposed that the α-NAGA mutant obtained by introducing these mutations into human α-NAGA can exist without any conformational problems.

In addition, a complex model in which a substrate of α-GAL was docked into the structure of the α-NAGA mutant was constructed. As a result, it was confirmed that the side chain of Glu188 of the α-NAGA mutant exists within a distance capable of forming a hydrogen bond with the hydroxyl group at the 2-position of the substrate (see FIG. 5(b)). Furthermore, in a complex model in which a substrate of α-NAGA was docked into the structure of the α-NAGA mutant, it was supposed that the N-acetyl group at the 2-position of the substrate causes a steric hindrance with the side chain of Leu191, which inhibited binding with the substrate.

According to the above results, it was expected that the α-NAGA mutant loses the specificity to the original substrate of α-NAGA and acquires a high specificity to the substrate of α-GAL (that is, the α-NAGA mutant substantially loses α-NAGA activity and acquires α-GAL activity).

Figure 6:
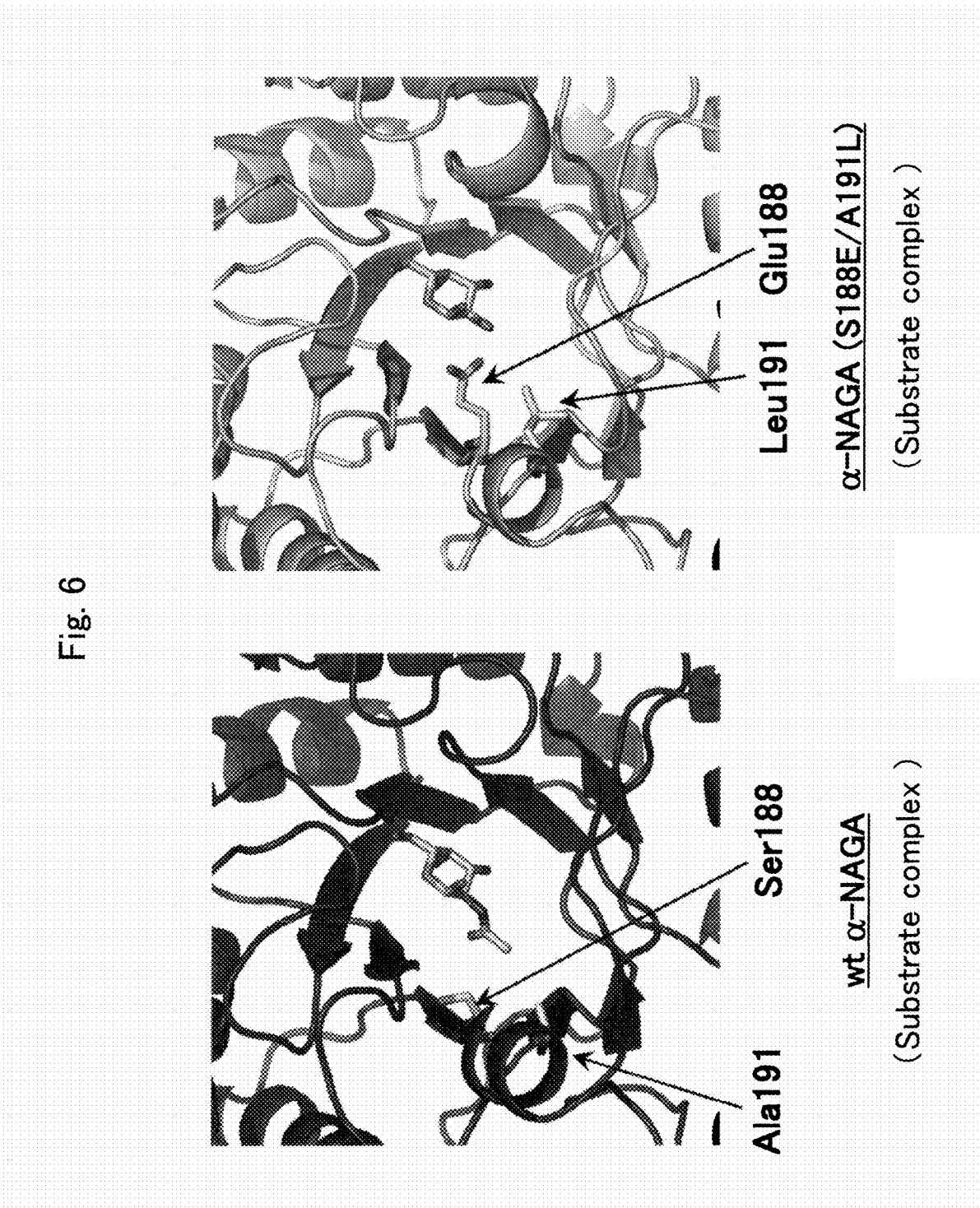
FIG. 6 gives schematic views showing the structures of the active sites of wild-type α-NAGA and an α-NAGA mutant, i.e., α-NAGA (S188E/A191L), respectively.

The structure of the constructed α-NAGA mutant (α-NAGA (S188E/A191L)) is shown in FIG. 6.

9. Other Candidates of Human α-NAGA Amino-Acid Substitution

The above-described modification of the substrate specificity is achieved by two effects, i.e., the inhibitory effect of binding to the substrate of α-NAGA through a steric hindrance and the formation effect of a hydrogen bond with a substrate of α-GAL. Regarding the above-described amino-acid substitutions, the possibility of substitution to other amino acids was studied.

First, for the above binding inhibitory effect, a substitution by Leu, i.e., the same amino acid as α-GAL, was performed as a first candidate. Furthermore, for a substitution resulting the same effect, a substitution by a hydrophobic amino-acid residue, Val, Ile, Phe or Met was considered.

In addition, for the above hydrogen bond formation effect, a substitution with Glu, i.e., the same amino acid as α-GAL, was performed as a first candidate. Furthermore, for a substitution resulting the same effect, a substitution by Asp, which also has a carboxyl group as Glu, was considered.

10. Amino Acid Sequence of Wild-Type Human α-NAGA and Amino Acid Sequence of α-NAGA Mutant The amino acid sequence of wild-type human α-NAGA is represented by "SEQ ID NO:2", and the amino acid sequence of the α-NAGA mutant (α-NAGA (S188E/A191L)) is represented by "SEQ ID NO:4".

EXAMPLE 2

Preparation of α-GAL Signal Peptide-Fused α-NAGA Mutant

According to the following procedure, "α-GAL signal peptide-fused α-NAGA mutant (α-GAL signal peptide-fused α-NAGA (S188E/A191L))", in which a signal peptide of α-GAL is fused with an α-NAGA mutant, i.e., α-NAGA (S188E/A191L).

1. Preparation of α-N-Acetylgalactosaminidase (α-NAGA) Retrovirus Vector

An α-NAGA cDNA clone (*Homo sapiens* N-acetylgalactosaminidase, alpha, m-RNA, Gene Bank Accession: BC000095, IMAGE: 3504221) was purchased from Open Biosystems. The coding sequence of α-NAGA was amplified by PCR with the following reaction mixture composition under the following reaction conditions, using the purchased α-NAGA cDNA as a template with primers described below and KOD-plus-polymerase (Toyobo Co., Ltd.).

NAGA-5' primer:
5'-GATGCTGCTGAAGACAGTGCTCTT-3'    (SEQ ID NO: 13)

NAGA-3' primer:
5'-TCACTGCTGGGACATCTCCAGGTT-3'    (SEQ ID NO: 14)

<Reaction Mixture Composition>

| | |
|---|---|
| Template (10 ng/μL): | 2 μL |
| 10 × buffer: | 10 μL |
| 2.5 mM dNTP: | 10 μL |
| 25 mM MgSO$_4$: | 4 μL |
| KOD-plus-polymerase: | 2 μL |
| NAGA-5' primer (10 μM): | 2 μL |
| NAGA-3' primer (10 μM): | 2 μL |
| Sterilized water: | 68 μL |
| Total: | 100 μL |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (90 seconds)" was performed for a total of 35 times, and the reaction mixture was then cooled at 4° C.

The prepared α-NAGA DNA fragment was purified by agarose gel electrophoresis.

An α-NAGA DNA fragment whose ends were phosphorylated with T4 polynucleotide kinase (New England Biolabs: NEB) was ligated with a retrovirus vector pCX4Neo prepared by cleaving with a restriction enzyme Hpa I (Blunt end) (NEB) and then dephosphorylating using Alkaline Phosphatase, Calf Intestine (NEB) (Tsuyoshi Akagi et al., Proc. Natl. Acad. Sci. USA, 100, 13567-13572 (2003)). α-NAGA pCX4Neo resulting from the ligation reaction was transformed into DH5a competent cells (Invitrogen Corporation) and seeded on an ampicillin-containing LB plate. Ampicillin-resistant colonies were then obtained.

Each of the resulting resistant colonies was suspended in an LB medium, which was used as a template to perform a colony PCR with the following reaction mixture composition under the following reaction conditions, with primers below and PCR Master Mix (manufactured by Promega).

NAGA-5' primer:
5'-GATGCTGCTGAAGACAGTGCTCTT-3'    (SEQ ID NO: 13)

pCX4-3' primer
5'-AAACCGTTGCTAGCTTAAGTT-3'    (SEQ ID NO: 15)

<Reaction Mixture Composition>

| | |
|---|---|
| Template (1 colony/10 μL): | 1 μL |
| PCR Master Mix: | 10 μL |
| NAGA-5' primer (10 μM): | 0.5 μL |
| pCX4-3' primer (10 μM): | 0.5 μL |
| Sterilized water: | 8 μL |
| Total: | 20 μL |

<Reaction Conditions>

The reaction mixture was heated at 95° C. for two minutes. Subsequently, a cycle consisting of "thermal denaturation and dissociation: 95° C. (30 seconds)→annealing: 55° C. (30 seconds)→synthesis and elongation: 72° C. (90 seconds)" was performed for a total of 40 times, and the reaction mixture was then cooled at 4° C.

A clone in which α-NAGA DNA was integrated in the forward orientation was selected from the resulting amplified product. More specifically, an *E. coli* template in which an amplified fragment of 1.4 kb was obtained was selected as a clone having the α-NAGA DNA integrated in the forward orientation. The selected *E. Coli* clone of α-NAGA pCX4Neo was mass-cultured to obtain 1 mg or more (1 mg/mL) of α-NAGA pCX4Neo plasmid DNA.

2. Preparation of α-NAGA Mutant

First, α-NAGA-(S188E) was prepared, based on which an α-NAGA mutant, i.e., α-NAGA (S188E/A191L), was prepared. The preparation method was carried out with reference to the instruction manual of the GeneTailor Site-Directed Mutagenesis System (Invitrogen Corporation), as needed.

First, α-NAGA pCX4Neo (100 ng) was methylated with DNA Methylase (4 U). α-NAGA-(S188E) was prepared by amplifying the DNA with the following reaction mixture composition under the following reaction conditions, using the methylated α-NAGA pCX4Neo as a template with a NAGA S188E-GT-5' primer (S188E missense mutation introduced is underlined) and a NAGA S188E-GT-3' primer which were designed such that the missense mutation (S188E) from 188th serine (S) to glutamic acid (E) was introduced, and KOD-plus-polymerase.

```
NAGA S188E-GT-5' primer:
                               (SEQ ID NO: 16)
5'-CCCATCGCCTTCTCCTGCGAGTGGCCAGCCTATGA-3'

NAGA S188E-GT-3' primer:
                               (SEQ ID NO: 17)
5'-GCAGGAGAAGGCGATGGGGCGGCCTGTG-3'
```

<Reaction Mixture Composition>

| Template (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| NAGA S188E-GT-5' primer (10 μM): | 1 μL |
| NAGA S188E-GT-3' primer (10 μM): | 1 μL |
| Sterilized water: | 34 μL |
| Total: | 50 μL |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (8 minutes)" was performed for a total of 35 times, and the reaction mixture was then cooled at 4° C.

The amplified DNA fragment (α-NAGA-(S188E) pCX4Neo) was transformed into DH5a-T1 competent cells (Invitrogen Corporation) having McrBC endonuclease which cleaves methylated DNA. Since α-NAGA pCX4Neo, which was used as a template, had been methylated, it was cleaved by McrBC endonuclease and could not form colonies. On the other hand, since a plasmid having an S188E mutation had not been methylated, it was not cleaved and could form colonies. The formed several colonies were then cultured, and the plasmid DNA was then extracted and purified. The introduction of the S188E mutation was confirmed by a known nucleotide sequencing method using a sequencer.

Next, α-NAGA (S188E/A191L) was prepared by PCR amplification with the following reaction mixture composition under the following reaction conditions, using the purified α-NAGA-(S188E) pCX4Neo as a template with a NAGA A191L-GT-5' primer (an A191L missense mutation introduced is underlined) and a NAGA A191L-GT-3' primer which were designed such that the missense mutation (A191L) from the 191st alanine (A) to leucine (L) was introduced, and KOD-plus-polymerase.

```
NAGA A191L-GT-5' primer:
                               (SEQ ID NO: 18)
5'-TTCTCCTGCGAGTGGCCACTCTATGAAGGCGGCCT-3'

NAGA A191L-GT-3' primer:
                               (SEQ ID NO: 19)
5'-TGGCCACTCGCAGGAGAAGGCGATGGGG-3'
```

<Reaction Mixture Composition>

| Template (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| NAGA A191L-GT-5' primer (10 μM): | 1 μL |
| NAGA A191L-GT-3' primer (10 μM): | 1 μL |
| Sterilized water: | 34 μL |
| Total: | 50 μL |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (8 minutes)" was performed for a total of 35 times, and the reaction mixture was then cooled at 4° C.

The amplified DNA fragment (α-NAGA (S188E/A191L) pCX4Neo) was transformed into DH5a-T1 competent cells. The plasmid DNA was then extracted and purified. The introduction of the A191L mutation, in addition to the S188E mutation, was confirmed by a known nucleotide sequencing method using a sequencer.

3. Preparation of α-GAL Signal Peptide-Fused α-NAGA and α-GAL Signal Peptide-Fused α-NAGA-Mutant When α-NAGA gene was introduced into an animal cell, the amount of the recombinant α-NAGA enzyme protein secreted into the culture supernatant was found to be little, with the majority remaining in the cell. Accordingly, in order to allow secretion of α-NAGA (wild-type) and α-NAGA mutant (α-NAGA (S188E/A191L)) into the culture supernatant in a large amount, recombinant α-NAGA enzyme proteins were produced whose signal peptide moieties (signal peptide moieties from α-NAGA) were replaced with signal peptide moieties from α-GAL that were known to be secreted into a culture supernatant in a large amount.

α-GAL cDNA was obtained by employing known nucleotide sequence information and cloning method. First, α-GAL cDNA was used as a template together with GLA-5' and SgGALNAGA2-3' primers, to amplify a nucleotide sequence encoding the signal peptide of α-GAL by PCR using the following reaction mixture composition under the following conditions. Here, the SigGALNAGA2-3' primer has a sequence homologous to 3'-terminal moiety of a nucleotide sequence encoding the signal peptide of α-GAL and a sequence homologous to 5'-terminal of a nucleotide sequence encoding α-NAGA. This PCR resulted in a DNA fragment having a nucleotide sequence encoding the signal peptide of α-GAL as an amplified product (hereinafter, referred to as PCR product A).

```
GLA-5' primer:
5'-ACAATGCAGCTGAGGAACCCAGAA-3' (SEQ ID NO: 20)

SigGALNAGA2-3' primer:
5'-GTCCAGTGCTCTAGCCCCAG-3'     (SEQ ID NO: 21)
```

<Reaction Mixture Composition>

| | |
|---|---|
| Template (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| GLA-5' primer (10 μM): | 1 μL |
| SigGALNAGA2-3' primer (10 μM): | 1 μL |
| Sterilized water: | 34 μL |
| Total: | 50 μL (PCR product A) |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (8 minutes)" was performed for a total of 35 times, and the reaction mixture was then cooled at 4° C.

Next, cDNA of each of α-NAGA and α-NAGA (S188E/A191L) was used as a template together with SigGALNAGA2-5' and NAGA-3' primers, to amplify a cDNA region consisting of a nucleotide sequence without a nucleotide sequence encoding the signal peptide of α-NAGA, by PCR using the following reaction mixture composition under the following conditions. Here, the SigGALNAGA2-5' primer has a sequence homologous to 3'-terminal moiety of a nucleotide sequence encoding the signal peptide of α-GAL and a sequence homologous to 5'-terminal moiety of α-NAGA. This PCR resulted in a DNA fragment having a nucleotide sequence encoding part other than the signal peptide moiety of α-NAGA or α-NAGA (S188E/A191L) as an amplified product (hereinafter, referred to as PCR product B).

```
SigGALNAGA2-5' primer:
5'-AGAGCACTGGACAATGGGCT-3'    (SEQ ID NO: 22)

NAGA-3' primer:
5'-TCACTGCTGGGACATCTCCAGGTT-3' (SEQ ID NO: 23)
```

<Reaction Mixture Composition>

| | |
|---|---|
| Template (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| SigGALNAGA2-5' primer (10 μM): | 1 μL |
| NAGA-3' primer (10 μM): | 1 μL |
| Sterilized water: | 34 μL |
| Total: | 50 μL (PCR product B) |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (a minute and 20 seconds)" was performed for a total of 35 times, and the reaction mixture was then cooled at 4° C.

Finally, the PCR products A and B resulting from the PCR above were used as templates for amplification using GLA-5' and NAGA-3' primers, with the following reaction mixture composition under the following conditions.

<Reaction Mixture Composition>

| | |
|---|---|
| PCR product A (6 ng/μL): | 1 μL |
| PCR product B (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| GLA-5' primer (10 μM): | 1 μL |
| NAGA-3' primer (10 μM): | 1 μL |
| Sterilized water: | 34 μL |
| Total: | 50 μL |

<Reaction Conditions>

The reaction mixture was heated at 94° C. for two minutes. Subsequently, a cycle consisting of "thermal denaturation and dissociation: 94° C. (15 seconds)→annealing: 60° C. (30 seconds)→synthesis and elongation: 68° C. (a minute and 20 seconds)" was performed for a total of 35 times, and the reaction mixture was then cooled at 4° C.

This PCR gave, as amplified products, a DNA fragment having a nucleotide sequence coding for α-GAL signal peptide-fused α-NAGA and a DNA fragment having a nucleotide sequence coding for α-GAL signal peptide-fused α-NAGA (S188E/A191L). Each of the resulting DNA fragments was separated by electrophoresis with a low-melt agarose gel, followed by purification using a commercially available DNA fragment purification kit.

Then, each of the purified DNA fragment having its terminal phosphorylated with T4 polynucleotide kinase (NEB) was ligated with a retrovirus vector pCX4Neo that has gone through cleavage with restriction enzyme Hpa I (blunt end) (NEB) followed by dephosphorylation with Alkaline Phosphatase, Calf Intestine (NEB) (Tsuyoshi Akagi et al., Proc. Natl. Acad. Sci. USA, 100, 13567-13572 (2003)) by a conventional gene recombinant technique. The α-GAL signal peptide-fused α-NAGA pCX4Neo and the α-GAL signal peptide-fused α-NAGA (S188E/A191L) pCX4Neo resulting from the ligation reaction were each transformed into DH5a competent cells (Invitrogen Corporation), seeded on an ampicillin-containing LB plate to obtain an ampicillin-resistant colony.

Each of the resulting resistant colonies was suspended in an LB medium. The cell solution was used as a template to perform colony PCR with the following primers and PCR Master mix (Promega) using the following reaction mixture composition under the following conditions.

```
pCX4-5' primer:
5'-GGGTGGACCATCCTCTAGACT-3'    (SEQ ID NO: 24)

NAGA-3' primer:
5'-TCACTGCTGGGACATCTCCAGGTT-3' (SEQ ID NO: 23)
```

<Reaction Mixture Composition>

| | |
|---|---|
| Template (1 colony/10 μL): | 1 μL |
| PCR Master mix: | 10 μL |
| pCX4-5' primer (10 μM): | 0.5 μL |
| NAGA-3' primer (10 μM): | 0.5 μL |
| Sterilized water: | 8 μL |
| Total: | 20 μL |

<Reaction Conditions>

The reaction mixture was heated at 95° C. for two minutes. Subsequently, a cycle consisting of "thermal denaturation and dissociation: 95° C. (30 seconds)→annealing: 55° C. (30 seconds)→synthesis and elongation: 72° C. (a minute and 20 seconds)" was performed for a total of 40 times, and the reaction mixture was then cooled at 4° C.

From the amplified product resulting from this PCR, clones having the DNA fragment of α-GAL signal peptide-fused α-NAGA or α-GAL signal peptide-fused α-NAGA (S188E/A191L) integrated in the forward orientation were selected. Specifically, *E. coli* templates with the 1.4 kb amplified product were selected as the clones having the DNA fragment of α-GAL signal peptide-fused α-NAGA or α-GAL signal peptide-fused α-NAGA (S188E/A191L) integrated in the forward orientation. *E. coli* clones of the selected α-GAL signal peptide-fused α-NAGA pCX4Neo and α-GAL signal peptide-fused α-NAGA (S188E/A191L) pCX4Neo were mass-cultured to obtain plasmid DNA of 1 mg or more (1 mg/mL).

EXAMPLE 3

Preparation of Recombinant Retrovirus Expressing α-GAL Signal Peptide-Fused α-NAGA or α-GAL Signal Peptide-Fused α-NAGA-Mutant Packaging cells of retrovirus (Phoenix Ampho Batch#: F-14727 Transformed Human Embryonic Kidney HEK293) were purchased from ATCC (Coligan, J. E. et al., Curr. Protocols Immunol., Suppl. 31, 10.28.1-10.28.17 (1999)). The *Phoenix* Ampho cells were cultured in a DMEM (high glucose) medium supplemented with 10% immobilized FBS and an antibiotic at 37° C. under 5% $CO_2$ concentration.

In order to prepare recombinant retroviruses, α-GAL signal peptide-fused α-NAGA pCX4Neo-retrovirus vector or α-GAL signal peptide-fused α-NAGA (S188E/A191L) pCX4Neo-retrovirus vector was transfected into the *Phoenix* Ampho cells. In this transfection, 2 mL of OPTI-MEM medium (Invitrogen Corporation) containing 1 μg of the retrovirus vector, 1 μg of pCLAMP (R K Naviaux et al., J. Virol., 70, 5701-5705 (1996)) and 18 μL of Dofect-GT1 (transfection reagent; Dojindo Laboratories) was added to the *Phoenix* Ampho cells ($5\times10^5$/60-mm dish), and the mixture was incubated at 37° C. for four hours. Subsequently, the culture medium was altered by a normal culture medium, and the resulting mixture was cultured for 48 hours. After the cultivation, the supernatant was collected and centrifuged at 1,000 rpm for 10 minutes. Recombinant retrovirus contained in the supernatant was dispensed and stocked at −80° C.

EXAMPLE 4

Establishment of CHO-K1 Cell Lines which Stably Express α-GAL Signal Peptide-Fused α-NAGA and α-GAL Signal Peptide-Fused α-NAGA Mutant Each of the recombinant retroviruses expressing α-GAL signal peptide-fused α-NAGA and α-GAL signal peptide-fused α-NAGA (S188E/A191L) prepared in Example 3 was used to infect CHO-K1 cell to establish stably expressing cells for α-GAL signal peptide-fused α-NAGA and α-GAL signal peptide-fused α-NAGA (S188E/A191L). Specifically, the establishment was performed through the following steps (i) to (v):

(i) $1\times10^5$ CHO-K1 cells were seeded on a 60-mm dish and cultured in an αMEM medium supplemented with 10% immobilized FBS and an antibiotic at 37° C. overnight.

(ii) Polybrene (Sigma H-9266, Hexadimethrine Bromide) was added to the culture medium to a final concentration of 2 μg/mL, and cultivation was performed at 37° C. for 30 minutes.

(iii) The culture medium was removed. Subsequently, 1 mL of a virus solution was added and was adsorbed at 37° C. for 60 minutes.

(iv) The virus solution was removed. Subsequently, 5 mL of a culture medium was added, and cultured overnight.

(v) Cultivation was performed with a selective medium supplemented with G418 (250 μg/mL), thereby establishing CHO-K1 cells. The selective medium was changed once every three days for 14 days or more. Whether or not the established cell expressed the target protein was confirmed by the enzymatic activity and a Western blotting method (for detail, see below).

[Confirmation of Expression of Target Protein by Western Blotting Method]

In order to examine whether or not the α-GAL signal peptide-fused α-NAGA-expressing CHO-K1 cells and the α-GAL signal peptide-fused α-NAGA (S188E/A191L)-expressing CHO-K1 cells, established with retroviruses, expressed the target protein, Western blotting was performed. An anti-α-NAGA polyclonal antibody obtained by a known method of preparing an antibody was provided as an antibody used in this Western blotting.

As the samples for the Western blotting, supernatants of the α-GAL signal peptide-fused α-NAGA-expressing CHO-K1 cells and α-GAL signal peptide-fused α-NAGA (S188E/A191L)-expressing CHO-K1 cells were used. SDS-PAGE was performed as follows. The concentration of a protein of the sample was measured. Subsequently, an equivalent volume of 2×SDS sample buffer (62.5 mM Tris-HCl, pH 6.8, 4% SDS, 30% glycerol, and 0.2% BPB) was added to the sample containing 5 μg of the protein. The mixture was boiled for five minutes, and the resulting sample was then applied to a 4% to 20% gel (PAG mini: Daiichi Pure Chemicals Co., Ltd.) to perform electrophoresis at a constant current of 30 mA for two hours.

After the electrophoresis, in order to transfer the protein onto a PVDF membrane (Immobilon-P, MILLIPORE), the gel was immersed in a blotting buffer (25 mM Tris-HCl, pH 8.3, 192 mM glycan, and 20% methanol) for 20 minutes, and placed on a PVDF membrane equilibrated with the blotting buffer. Transfer was then performed using a Hoefer TE 70 semi-dry transfer unit (Amersham Biosciences) at a constant current of 60 mA for an hour.

After the completion of transfer, the membrane was blocked with a blocking buffer (5% skim milk in TBS (50 mM Tris-HCl, pH 7.4 and 100 mM NaCl)) for 30 minutes. An anti-NAGA polyclonal antibody (primary antibody) diluted 500-fold with the blocking buffer was then added thereto, and incubation was performed at 4° C. overnight.

The membrane obtained after the incubation with the primary antibody was washed with TBS for five minutes for three times. An anti-rabbit IgG HRP-labeled antibody (secondary antibody; Amersham Biosciences) diluted 5,000-fold with the blocking buffer was then added thereto, and incubation was performed at room temperature for an hour.

The membrane obtained after the incubation with the secondary antibody was washed with TBS for five minutes for three times. An ECL coloring reagent (Nacalai Tesque, Inc.) was added to allow reaction at room temperature for two minutes. Subsequently, the membrane was developed by bringing into contact with Hyperfilm™ ECL in a darkroom for a minute.

From the above results, it was confirmed that the established α-GAL signal peptide-fused α-NAGA-expressing CHO-K1 cells and the α-GAL signal peptide-fused α-NAGA (S188E/A191L)-expressing CHO-K1 cells each secreted wild-type α-NAGA and α-NAGA mutant (α-NAGA (S188E/A191L)) of approximately 45 kD into the culture supernatants, respectively.

EXAMPLE 5

Transition of Enzymatic Activity of α-GAL Signal Peptide-Fused α-NAGA Mutant The fact that the α-GAL signal peptide-fused α-NAGA (S188E/A191L) had acquired the substrate specificity of α-GAL was confirmed by the following procedure.

The culture supernatants of α-GAL signal peptide-fused α-NAGA-expressing CHO-K1 cells and the α-GAL signal peptide-fused α-NAGA (S188E/A191L)-expressing CHO-K1 cells established in Example 4 were used as samples to perform an enzymatic activity assay for α-GAL and α-NAGA activities. The enzymatic activity was determined using a synthetic substrate composed of a fluorogenic substrate, i.e., a 4-methylumbelliferone (4-MU) derivative, by measuring the amount of 4-MU released from 1 mL of the enzyme solution per hour as a fluorescence intensity. More specifically, 4-MU-α-D-galactoside (4-MU-α-GAL; Calbiochem, Calif.) was used as the synthetic substrate of α-GAL. 4-MU-α-N-acetyl-D-galactosaminide (4-MU-α-NAGA; Seikagaku Corporation) was used as the synthetic substrate of α-NAGA. For the measurement of α-GAL activity, N-acetyl-D-galactosamine (Sigma, Mo.) as an inhibitor of α-NAGA, which reacts with 4-MU-α-GAL at the same time, was added to the substrate solution in advance to a final concentration of 117 mM.

A McIlvain's buffer (citric acid/phosphoric acid, pH 4.6, 40 µL) containing 5 mM 4-MU-α-GAL or a McIlvain's buffer (citric acid/phosphoric acid, pH 4.7, 40 µL) containing 1 mM 4-MU-α-NAGA was added to the culture supernatant (10 µL) and mixed, and a reaction was allowed at 37° C. for 30 minutes. The reaction was terminated by adding a 0.2 M Glycine buffer (pH 10.7, 950 µL). In order to detect the amount of 4-MU released, the amount of 4-MU was measured at an excitation wavelength of 365 nm and a fluorescence wavelength of 450 nm using a spectrofluorophotometer (ARVO MX, Perkin Elmer). The enzymatic activity of α-GAL or α-NAGA was determined by the amount of 4-MU (nmol 4-MU/h/ml) that can be released per volume and reaction time of the enzymatic solution.

The results from the enzymatic activity assay showed that α-GAL signal peptide-fused α-NAGA (S188E/A191L) expressed by CHO-K1 cell was secreted into the culture supernatant and showed high α-GAL activity, indicating acquirement of the α-GAL substrate specificity.

The results are shown in Table 4.

TABLE 4

| | α-GAL enzymatic activity (nmol 4-MU/h/ml) |
|---|---|
| CHO-K1 (control) | 0-20 |
| α-GAL signal peptide-fused α-NAGA | 0-20 |
| α-GAL signal peptide-fused α-NAGA-(188E/A191L) | 200-400 |

EXAMPLE 6

Stability of α-GAL Signal Peptide-Fused α-NAGA Mutant in Blood (in Plasma)

The stability of the α-GAL signal peptide-fused α-NAGA (S188E/A191L) in blood (in plasma) was confirmed by the following procedure.

First, an enzyme solution of α-GAL signal peptide-fused α-NAGA (S188E/A191L) was prepared as in Example 4. In addition, as a control, another enzyme solution was prepared in the same manner as the above enzyme solution using cells prepared by introducing a gene of wild-type α-GAL into F377. Plasma (50 µL) of a healthy subject was added to each of the enzyme solutions (50 µL) and mixed. A reaction was then initiated at 37° C., and 10 µL of the reaction mixture was sampled with time to measure α-GAL activity. The enzymatic activity was measured as in Example 4. The α-GAL activity of the sample sampled at the time of mixing the enzyme solution with plasma was defined as a standard (100%), and a decrease in the enzymatic activity with time was represented as a percentage.

As a result, α-GAL signal peptide-fused α-NAGA (S188E/A191L) had an excellent α-GAL-activity-maintaining ability in blood (in plasma) with time, as compared to wild-type α-GAL, showing that α-NAGA (S188E/A191L) is highly stable in blood.

EXAMPLE 7

Degradation of Ceramide Trihexoside (CTH) Accumulated in Fabry Disease Patient-Derived Fibroblasts by α-GAL Signal Peptide-Fused α-NAGA Mutant The culture supernatants of α-GAL signal peptide-fused α-NAGA-expressing CHO-K1 cell and α-GAL signal peptide-fused α-NAGA (S188E/A191L)-expressing CHO-K1 cell were collected to be used as enzyme samples. α-GAL signal peptide-fused α-NAGA, α-GAL signal peptide-fused α-NAGA (S188E/A191L) and α-GAL with an activity of 1,000 nmol/h/ml were added to the media of cultured Fabry disease patient-derived fibroblasts (F337) for cultivation for two days. At the end of cultivation, CTH accumulated within the cells was detected by fluorescent antibody staining as follows.

First, Fabry disease patient-derived fibroblasts cultured via enzyme addition, was immobilized with 4% paraformaldehyde/PBS (pH 7.0) for a minute, added with 1% BSA/PBS, blocked at room temperature for 30 minutes, added with anti-CTH monoclonal antibody (primary antibody) diluted 100-fold with 1% BSA/PBS, and incubated at room temperature for an hour. Incubation with the primary antibody was followed by three times of five-minute wash with PBS. Then, Alexa Fluor 488 Goat anti-mouse-IgG diluted 1000-fold with 1% BSA/PBS (secondary antibody: Invitrogen) was added and incubated at room temperature for an hour. Incubation with the secondary antibody was followed by three times of five-minute wash with PBS, mounting with Permafluor Mount Medium (Thermo), and observation with confocal laser microscope system LSM510 (Carl Zeiss).

Figure 7:
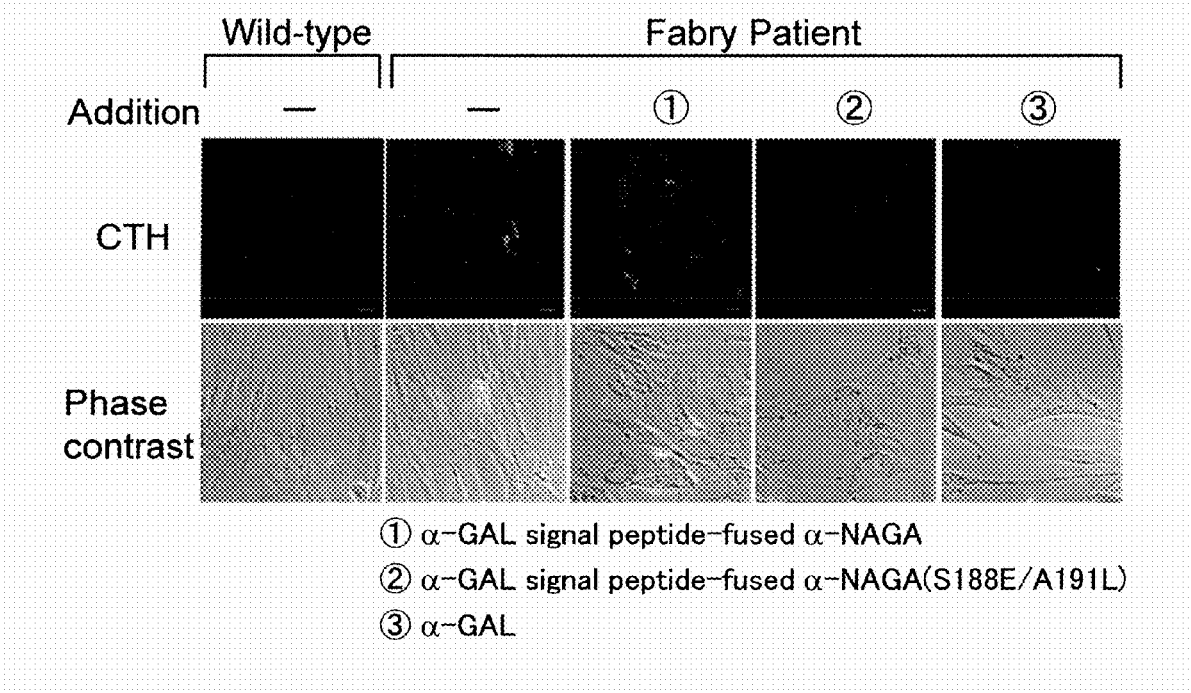
FIG. 7 is a view showing the results from immunostaining, showing the effects of additions of α-GAL signal peptide-fused α-NAGA, an α-GAL signal peptide-fused α-NAGA mutant and wild-type α-GAL on the amount of CTH accumulated in Fabry disease patient-derived fibroblasts.

As a result of the antibody staining, significant CTH reduction was observed in the Fabry disease patient-derived fibroblast media added with α-GAL signal peptide-fused α-NAGA (S188E/A191L) and α-GAL whereas no significant CTH reduction was observed with α-GAL signal peptide-fused α-NAGA (FIG. 7).

EXAMPLE 8

Establishment of Technique of Purifying α-GAL Signal Peptide-Fused α-NAGA Mutant (1)

A preliminary experiment was carried out in order to establish a technique of purifying α-GAL signal peptide-fused α-NAGA (S188E/A191L). The culture supernatant (about 6 liters) containing α-GAL signal peptide-fused α-NAGA (S188E/A191L) secreted from stably expressing CHO-K1 cell line obtained in Example 4 was collected and concentrated by ultrafiltration (molecular weight cut-off at 30 kD: Millipore YM30) to an about 170 ml (30-fold) concentration. Subsequently, the resultant was exchanged with a 20 mM MES (pH 6.0) buffer by dialysis.

As the first step, an α-NAGA mutant with an enzymatic activity of 500 μmol/h (about 6 mg) was adsorbed onto a HiLoad Q Sepharose HP (26/10) anion-exchange column equilibrated with 20 mM MES (pH 6.0), which was then washed with 20 mM MES (pH 6.0) and further with 150 mM NaCl/20 mM MES (pH 6.0). Thereafter, the α-NAGA mutant was eluted with 250 mM NaCl/20 mM MES (pH 6.0) to collect fractions with high enzymatic activity. The recovery yield with the HiLoad Q Sepharose anion-exchange column was approximately 47% with 7.4-fold purification.

As the second step, a Q Sepharose HP column eluate (enzymatic activity 224 μmol/h: about 3 mg) was applied to a HiTrap Heparin HP column equilibrated with 20 mM MES (pH 6.0) to allow impurity to adsorb onto the column. 20 mM MES (pH 6.0) was loaded onto the column and the α-NAGA mutant fraction that flowed through the column was collected. The recovery yield after the Heparin HP column was 44% with 15.7-fold purification.

As the third step, the fraction (enzymatic activity 213 μmol/h: about 3 mg) that flowed through the heparin column equilibrated with a 1 mM potassium phosphate buffer (pH 6.0) was adsorbed onto a Bio-Scale CHT-2 hydroxyapatite column. The column was washed with 1 mM potassium phosphate buffer (pH 6.0), then subjected to elution with 37.5 mM potassium phosphate buffer (pH 6.0) to collect a fraction with high enzymatic activity. The recovery yield after the Bio-Scale CHT-2 hydroxyapatite column was 18% with 55-fold purification.

The steps of above-described purification are shown in Table 5.

EXAMPLE 9

Examination of Uptake of α-GAL Signal Peptide-Fused α-NAGA Mutant by Various Organs α-GAL signal peptide-fused α-NAGA mutants (partial purification; obtained in Example 8) with an α-GAL enzymatic activity comparable to 1 mg/kg or 0.3 mg/kg of commercially available α-GAL preparation (Fabrazyme; Genzyme) were intraperitoneally (ip.) or intravenously (iv.) administered to Fabry disease model mice to examine uptake by liver. In this example, the term "α-NAGA mutant" refers to "α-NAGA (S188E/A191L)".

[Method]
1. The following experimental groups were established with Fabry disease model mice (also referred to as "Fabry disease mice") (male, 9-13 g) and wild-type mice (wild-type mice belonged to experimental group 1) only).
   1) non-administered group (control) (n=1)
   2) α-NAGA mutants (with an activity comparable to 1 mg/kg Fabrazyme), ip. administration group (n=3)
   3) α-NAGA mutants (with an activity comparable to 0.3 mg/kg Fabrazyme), iv. administration group (n=2)
2. Sixty minutes after the administration, livers, hearts and kidneys were resected from the mice other than the controls after systemic perfusion with 30 ml PBS under anesthesia. α-GAL activity of each organ was determined by a routine method.

[Results]
The results from comparison of α-GAL activities in various organs in each experimental group are shown in Table 6.

TABLE 6

| | Wild-type mice | Fabry disease model mice | | |
| --- | --- | --- | --- | --- |
| | Non-administered | Non-administered | α-NAGA mutant ip. | α-NAGA mutant iv. |
| Liver | 17 | 0.18 | 31 | 31 |
| Heart | 7.0 | 0.12 | 1.8 | 3.2 |
| Liver | 11 | 0.38 | 2.7 | 1.3 |

(nmol/h/mg)

As can be appreciated from the above results, the α-GAL activity in the livers of the non-administered group (control) was almost 0. On the other hand, average α-GAL activity in the livers of the α-NAGA mutant ip. administration group

TABLE 5

Steps of purifying α-GAL signal peptide-fused α-NAGA mutant

| Sample | Amount of solution (ml) | Protein concentration (mg/ml) | Specific activity (μmol/h/ml) | Specific activity (μmol/h/mg) | Total specific activity (μmol/h) | Folding | Total amount of protein (mg) | Recovery (%) |
| --- | --- | --- | --- | --- | --- | --- | --- | --- |
| Amicon concentration/dialysis | 168.5 | 5.3 | 2.86 | 0.54 | 482 | 1 | 893.05 | 100 |
| HiLoadQ dialysis | 92 | 0.61 | 2.44 | 3.99 | 224 | 7.4 | 56.2 | 47 |
| Heparin dialysis | 120 | 0.21 | 1.77 | 8.45 | 213 | 15.7 | 25.2 | 44 |
| Hydroxy apatite | 12.6 | — | 6.95 | — | 88 | — | — | 18 |
| Concentration | 2 | 1.10 | 32 | 29.8 | 65 | 55 | 2.2 | 14 |

*α-NAGA mutant . . . dissolved in 35 mM potassium phosphate buffer (pH 6.0)

was 31 (nmol/h/mg), which exceeded the α-GAL activity in the liver of the wild-type mice. In addition, average α-GAL activity in the livers of the α-NAGA mutant iv. administration group was also as high as 31 (nmol/h/mg).

As to the comparison between the ip. administration group and the iv. administration group of α-NAGA mutants, the uptake by the liver was the same, i.e., 31, as mentioned above. Since, however, the dosages for the ip. and iv. administration groups were 1.0 mg/kg and 0.3 mg/kg, respectively, the iv. administration route was found to provide more effective uptake by the liver than the ip. administration route.

The α-GAL activities in the heart and kidney were lower than that in the liver, indicating that the uptake efficiencies of the α-NAGA mutant by the heart and kidney were lower than that by the liver. However, generally, about 20% activity of the normal value (i.e., the value of the non-administrated group of wild-type mice) is considered to cause no abnormality in the body. Accordingly, even the α-GAL activities in the heart and kidney seemed to be exhibiting sufficient effectiveness of the α-NAGA mutant.

In addition, kidney and heart are part of the organs that become particularly problematical when dysfunction is caused upon onset of Fabry disease, and they are, along with the endothelial cells, the target organ tissues of administration of a therapeutic agent. Although conventional therapeutic agents for enzyme replacement therapy exhibit a certain level of effect on the endothelial cells, their effects were insufficient in kidney and heart. Hence, the above results of α-GAL activity enhancement in the heart and kidney (as compared to the Fabry disease model mice group without α-NAGA mutant administration) indicated that the α-NAGA mutant was an excellent enzyme protein as an active element of a therapeutic agent for Fabry disease.

EXAMPLE 10

Establishment of Technique of Purifying α-GAL Signal Peptide-Fused α-NAGA Mutant (2)

An α-GAL signal peptide-fused α-NAGA mutant (α-GAL signal peptide-fused α-NAGA (S188E/A191L), hereinafter, referred to as an "α-NAGA mutant" in the present example) was purified.

The culture supernatant (about 20 liters) of α-GAL signal peptide-fused α-NAGA (S188E/A191L) secreted from the stably expressing CHO-K1 cell line obtained in Example 4 was collected and concentrated by ultrafiltration (molecular weight cut-off at 30 kD: Millipore YM30) to an about 740 ml (27-fold) concentration. Subsequently, ammonium sulfate was added to the resultant to 50% and the resulting precipitate was collected by centrifugation (17,000 rpm). The precipitate was dissolved in 20 mM MES (pH6.0)/900 mM ammonium sulfate to give 1,400 ml.

Then, this solution was added to a HiLoad Pheny Sepharose HP (26/10) column equilibrated with 20 mM MES (pH6.0)/900 mM ammonium sulfate to allow adsorption of the α-NAGA mutant. The resultant was washed with 20 mM MES (pH6.0)/900 mM ammonium sulfate and 20 mM MES (pH6.0)/500 mM ammonium sulfate. Subsequently, the α-NAGA mutant was eluted with 20 mM MES (pH6.0)/200 mM ammonium sulfate to collect fractions with high enzymatic activity. The recovery yield until the HiLoad Phenyl Sepharose HP (26/10) column was approximately 63% with 12-fold purification.

The active fraction of HiLoad Phenyl Sepharose HP (26/10) column chromatography was dialyzed with 20 mM sodium acetate (pH 5.0) and then added to a HiLoad SP Sepharose HP (26/10) column equilibrated with 20 mM sodium acetate (pH 5.0). The α-NAGA mutant was collected in the flow-through fraction of 20 mM sodium acetate (pH 5.0). The active recovery yield until the HiLoad SP Sepharose HP (26/10) column was approximately 40% with 188-fold purification.

The resulting active fraction was added to a Q Sepharose HP (26/10) column equilibrated with 20 mM MES (pH 6.0) to allow adsorption of the α-NAGA mutant. The resultant was washed with 20 mM MES (pH 6.0)/140 mM sodium chloride and 20 mM MES (pH 6.0)/190 mM sodium chloride. Subsequently, the α-NAGA mutant was eluted with 20 mM MES (pH 6.0)/250 mM sodium chloride to collect fractions with high enzymatic activity. The active recovery yield until the HiLoad Q Sepharose HP (26/10) column was approximately 38% with 489-fold purification.

The steps of the above-described purification of the α-NAGA mutant are shown in Table 7 below.

TABLE 7

| Step | Amount of solution (ml) | Protein concentration (mg/ml) | Activity (μmol/h/ml) | Specific activity (μmol/h/mg) | Total activity (mmol/h) | Folds | Total amount of protein (mg) | Recovery (%) |
|---|---|---|---|---|---|---|---|---|
| Amicon concentration | 740 | 82 | 74 | 0.90 | 55 | 1 | 60936 | 100 |
| 50% ammonium sulfate precipitation | 1400 | 20 | 38 | 1.9 | 53 | 2.1 | 27983 | 96 |
| Phenyl-Sepharose | 425 | 7.7 | 81 | 10 | 34 | 12 | 3269 | 63 |
| SP-Sepharose | 185 | 0.71 | 119 | 169 | 22 | 188 | 131 | 40 |
| Q-Sepharose | 45 | 1.06 | 465 | 439 | 21 | 489 | 48 | 38 |

Figure 8:
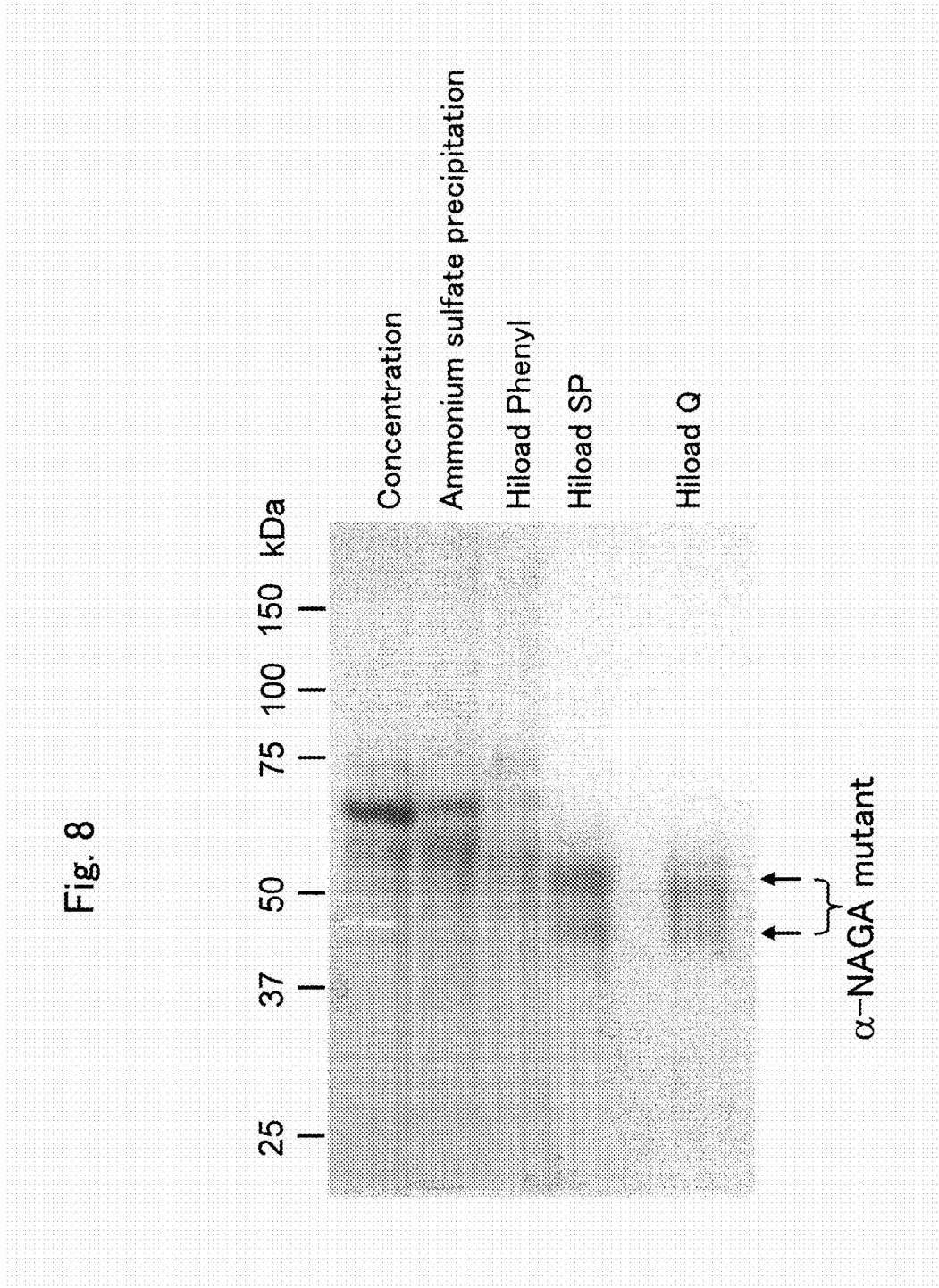
FIG. 8 is a view showing CBB staining images of a reagent at respective steps during purification of an α-NAGA mutant, i.e., α-NAGA (S188E/A191L).

The reagent at each purification step (protein content: 10 μg) was separated by SDS-polyacrylic amide gel electrophoresis according to a conventional method and subjected to CBB staining. The results are shown in FIG. 8. In FIG. 8, two bands are observed which represent the α-NAGA mutant (see arrows in the figure) whereas only a single band appeared after treatment with N-glycanase (not shown). Thus, proteins from the two bands are the same α-NAGA mutants except for the number of sugar chains.

EXAMPLE 11

Examination of Uptake of α-GAL Signal Peptide-Fused α-NAGA Mutant by Various Organs The α-NAGA mutant obtained by purification in Example 10 was intravenously administered (iv. administered) to the Fabry disease model mice (also referred to as Fabry disease mice) to examine the uptake by various organs.

In this example, an "α-NAGA mutant" refers to "α-NAGA (S188E/A191L)".

[Method]

1. The following experiment groups 1) to 3) were established with Fabry disease model mice (male, 25-35 g) and wild-type mice.
   1) Wild-type mice (n=3)
   2) Fabry disease mice (n=3)
   3) Fabry disease mice, α-NAGA mutant-administered group (n=3) (dosage: 1.9 mmol/hr/kg mouse weight (with an activity comparable to 1 mg/kg Fabrazyme))

2. Sixty minutes after the administration, livers, kidneys, hearts, lungs, brains and skeletal muscle were resected from group 3) administered with the α-NAGA mutant after systemic perfusion with 30 ml PBS under anesthesia.

[Results]

The results from comparison of α-GAL activities in various organs are shown in Table 8 below.

Fabry disease model mice (also referred to as Fabry disease mice) for multiple doses. Twenty-four hours later, uptake by the various organs and effect of degrading the accumulated substance in the various organs were examined.

In the present example, an "α-NAGA mutant" refers to "α-NAGA (S188E/A191L)".

[Method]

1. The following experimental groups were established with Fabry disease model mice (male, 15-20 g) and wild-type mice. Here, 1) and 2) are the same as 1) and 2) in Example 11.
   1) wild-type mice (n=3)
   2) Fabry disease mice (n=3)
   3) Fabry disease mice, α-NAGA mutant-administered group (n=4) (given 1.9 mmol/hr/kg mouse weight per dose, every 24 hours for four times)

2. <<Measurement of α-GAL Activity>>

Twenty-four hours after the fourth administration, liver, kidney, heart, lung, brain and skeletal muscle were resected from group 3) given the α-NAGA mutant, after blood removal under anesthesia. α-GAL activity in each organ was determined according to a routine method.

3. <<Analysis of Substrate Degradation Effect: TLC Analysis>>

The substrate degradation effect in each organ was determined by measuring ceramide trihexoside (CTH) accumulated in the organs. The resected liver, kidney and heart was frozen at −80° C. and used for extraction of total glycolipid from each organ. The frozen organs (50-250 mg) were homogenized in water to 250 mg/ml and subjected to extraction with a solvent composition of chloroform:methanol:wa-

TABLE 8

α-galactosidase activities in various organs after an hour following single-dose administration of α-NAGA(S188E/A191L) to Fabry disease mice

| | α-galactosidase activity (nmol/h/mg protein: mean ± SD) | | | | | |
|---|---|---|---|---|---|---|
| | Kidney | Heart | Liver | Lung | Brain | Skeletal muscle |
| Wild-type mice (n = 3) | 11 ± 2 | 3.5 ± 0.6 | 14 ± 7 | 28 ± 6 | 23 ± 4 | 3.8 ± 0.7 |
| Fabry disease mice (n = 3) | <1 | <1 | <1 | <1 | <1 | <1 |
| Fabry disease mice + α-NAGA(S188E/A191L) (n = 3) | 24 ± 4 | 10 ± 2 | 193 ± 30 | 19 ± 10 | <1 | <1 |

As can be appreciated from the results above, α-GAL activity in each tissue of the Fabry disease mice was 1.0 nmol/h/mg protein or lower. On the other hand, for the α-NAGA mutant-administered group, α-GAL activity increased in four organs except the brain and the skeleton muscle as compared to the Fabry disease mice. In the kidney and heart, i.e., the organs predominantly affected by Fabry disease, α-GAL activity was higher than that in the kidney and heart of the wild-type mice, respectively, showing usefulness of the α-NAGA mutant.

EXAMPLE 12

Experiment for Confirming Acquirement of α-GAL Activity and Effect of Degrading Accumulated Substance in Various Organs by Multiple Doses of α-GAL Signal Peptide-Fused α-NAGA Mutant The α-NAGA mutant obtained by purification in Example 10 was intravenously administered (iv. administered) to ter=4:8:3 according to the method of Svennerholm L and Fredman P (see Svennerholm L, Fredman P, A procedure for the quantitative isolation of brain gangliosides., Biochem. Biophys. Acta., 1980; 617:97-109). Following centrifugation, the extract solution was collected. The residues were subjected to extraction again with a solvent composition of chloroform:methanol:water=5:10:4, centrifuged and the resulting extract solution was mixed with the former extract solution. The mixed extract solution was evaporated to dryness under nitrogen stream.

Upon CTH analysis, the dried samples were dissolved in a solvent composition of chloroform:methanol:water=40:20:3 at 2 μl per wet weight of organ (mg). The prepared organ extract solution was added to silica gel 60 HPTHL together with a standard CTH preparation (swine erythrocytic CTH, Wako Pure Chemicals), and developed with a developing solvent of chloroform:methanol:0.22% aqueous calcium chloride=11:9:2. After drying the HPTLC, the resultant was subjected to chemical color development with orcinol reagent.

4. <<Analysis of Substrate Degradation Effect: Immunohistochemical Analysis>>

The substrate degradation effect in each organ was analyzed immunohistochemically. According to a conventional method (see Ikuya Nonaka, Pathology of Muscles for Clinical Medicine, 3rd revised edition, Japan Medical Journal), the resected livers, kidneys and hearts were sliced to prepare 6 µm-thin frozen sections with a cryostat. Furthermore, immunohistostaining was performed according to a conventional method (see H. Sakuraba et al., Corrective effect of recombinant human α-galactosidase having mammalian-like-mannose-type sugar chains produced in yeast on Fabry mice., J. Human Genet., 51, 341-352, 2006). The frozen sections were immobilized with 4% paraformaldehyde/PBS (pH 7.0) for 15 minutes, added with 10% goad serum/PBS, blocked at room temperature for an hour, added with anti-CTH monoclonal antibody diluted 2-fold with 10% goat serum/PBS (primary antibody), and incubated at 37° C. for two hours. Following incubation with the primary antibody, the resultant was washed with 0.05% Tween20/PBS (PBS-T) for 5 minutes for three times. Alexa Fluor 488 goat anti-mouse-IgG (secondary antibody: Invitrogen) diluted 1000-fold with 10% goat serum/PBS was added and incubated at room temperature for an hour. Following incubation with the secondary antibody, the resultant was washed with PBS-T for 5 minutes for three times, mounted with Permafluor mount medium (Thermo) and observed with a fluorescent microscopic system Axiovert135 (Carl Zeiss).

[Results]

1. <<Measurement of Remaining Activity>>

The results from comparison of α-GAL activities in various organs are shown in Table 9 below.

TABLE 9

α-galactosidase activity of each tissue 24 hours after four times of α-NAGA(S188E/A191L) administration to Fabry disease mice

| | α-galactosidase activity (nmol/h/mg protein; mean ± SD) | | | | | |
|---|---|---|---|---|---|---|
| | Kidney | Heart | Liver | Lung | Brain | Skeletal muscle |
| Wild-type mice (n = 3) | 11 ± 2 | 3.5 ± 0.6 | 14 ± 7 | 28 ± 6 | 23 ± 4 | 3.8 ± 0.7 |
| Fabry disease mice (n = 3) | <1 | <1 | <1 | <1 | <1 | <1 |
| Fabry disease mice + α-NAGA(S188E/A191L) (n = 4) | 16 ± 1 | 30 ± 7 | 380 ± 34 | 14 ± 7 | <1 | 1.2 ± 0.3 |

For the group given four doses of the α-NAGA mutant, no α-GAL activity was detected in the brains 24 hours after the final administration. On the other hand, in the organs other than the brain, higher α-GAL activity remained as compared to the Fabry disease mice. In the organs predominantly affected by Fabry disease, i.e., the kidneys and hearts, α-GAL activity was higher than those in the kidneys and hearts of the wild-type mice, respectively. This shows that the α-NAGA mutant remains not only immediately after the administration but for a few days in the predominantly affected organs, i.e., the kidneys and hearts. Considering that an activity of about 20% of the normal value is generally presumed to cause no abnormality in the body, administration of the α-NAGA mutant at regular intervals would maintain sufficient activity in the heart and kidney.

Kidneys and hearts are part of organs where dysfunction upon onset of Fabry disease becomes particularly problematical, and thus they are target organ tissues, along with vascular endothelial cells, upon administering a therapeutic agent. Although conventional therapeutic agents for enzyme replacement therapy show some level of effects on vascular endothelial cells, their effects were insufficient on kidneys and hearts. Thus, the results of α-GAL activities in the hearts and kidneys shown above prove that the α-NAGA mutant is an excellent enzyme protein as an active element of a therapeutic agent for Fabry disease.

2. <<Analysis of Substrate Degradation Effect>>

Figure 9:
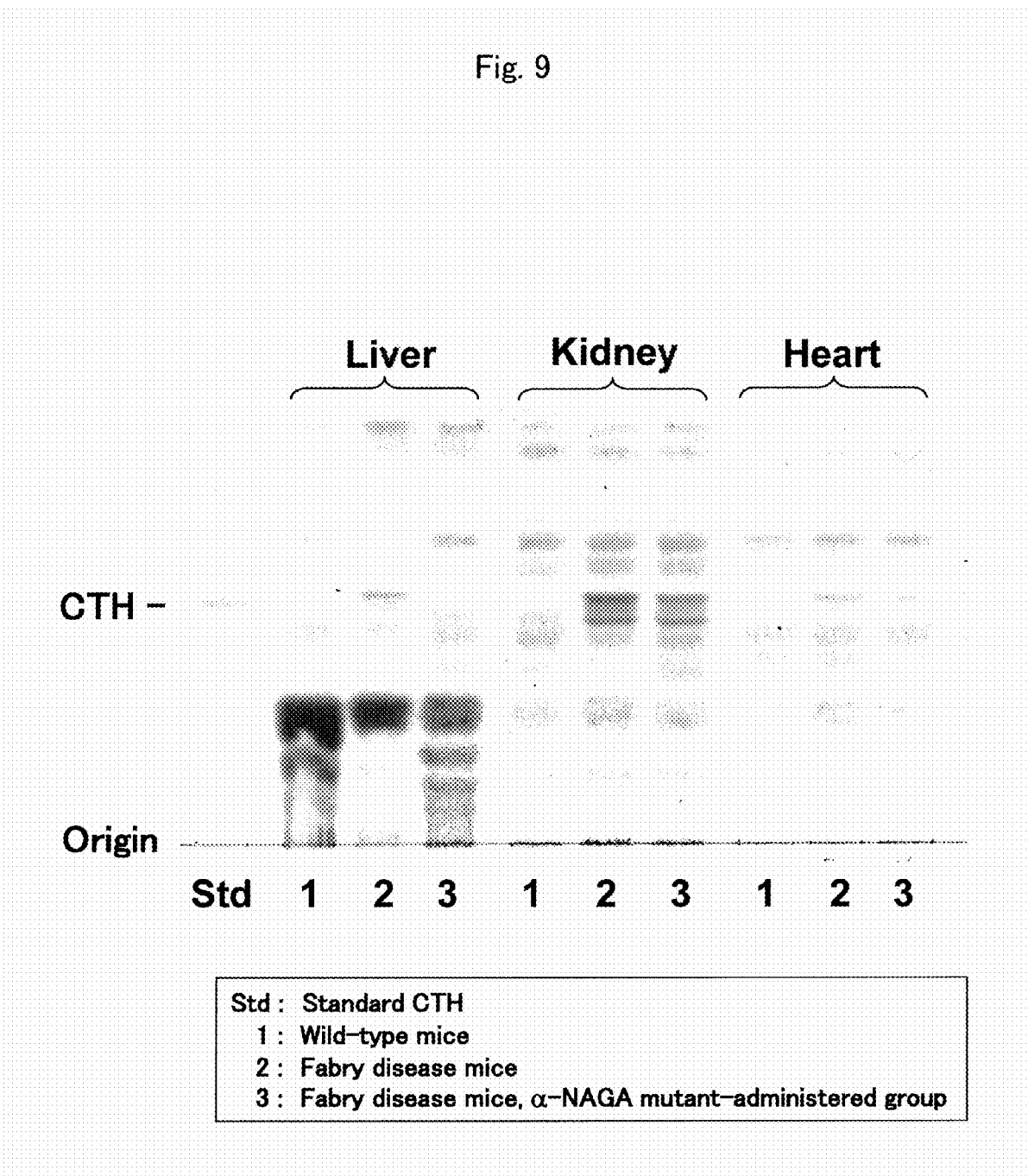
FIG. 9 is a view showing the results from an analysis of CTH, i.e., a substrate of α-GAL, in the liver, kidney and heart.

The results from analysis of CTH, i.e., a substrate of α-GAL, in the livers, kidneys and hearts are shown in FIG. 9. The TLC sheet was dried and then subjected to TLC immunostaining using anti-CTH antibody according to a routine method (see Kotani M et al., Generation of one set of murine monoclonal antibodies specific for globo-series glycolipids: evidence for differential distribution of the glycolipids in rat small intestine., Arch. Biochem. Biophys., 1994; 310: 89-96) to confirm that the band marked CTH in the figure was actually CTH.

The amounts of CTH in all of the livers, kidneys and hearts of the Fabry disease mice administered with the α-NAGA mutant for four times were reduced as compared to the amounts of CTH in the respective organs of the non-administered Fabry disease mice group.

3. <<Analysis of Substrate Degradation Effect: Immunohistochemical Analysis>>

Figure 10:
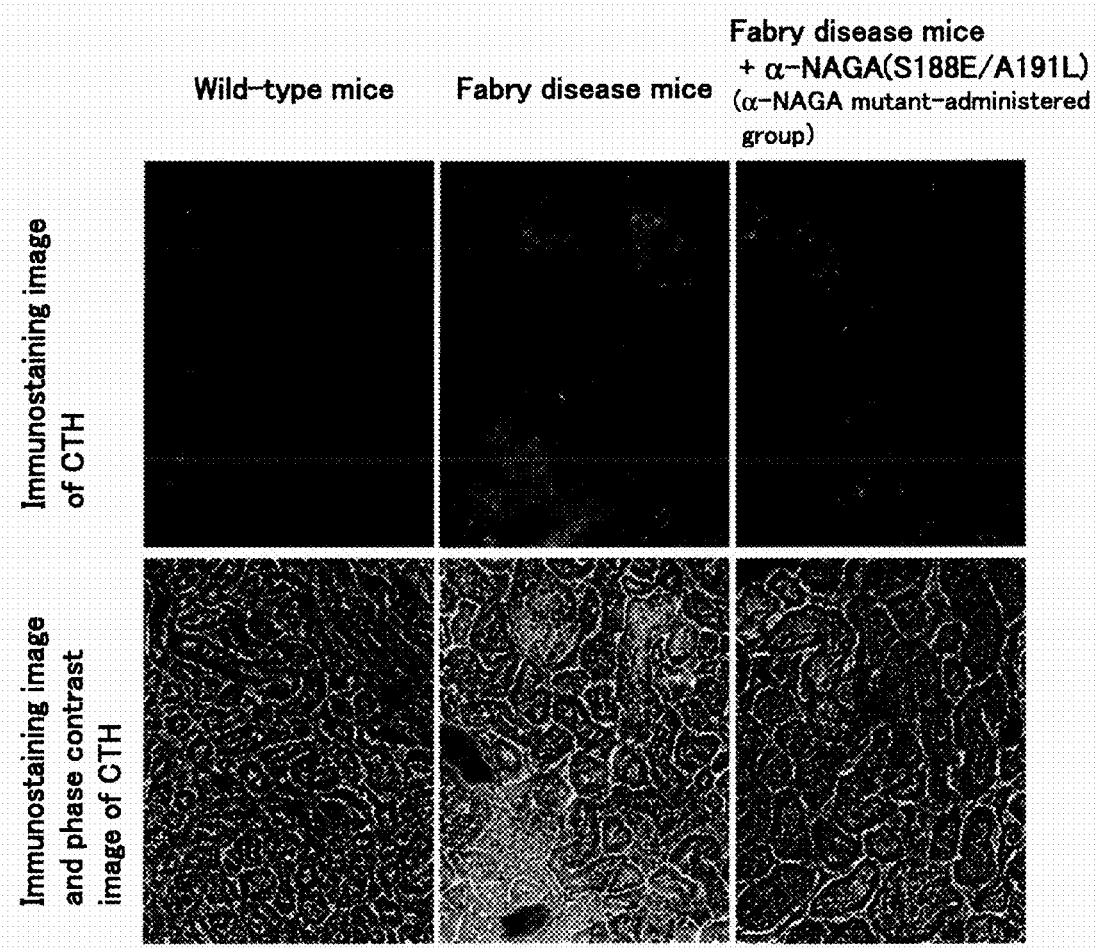
FIG. 10 is a view showing the results from immunostaining of kidney tissues.
Figure 11:
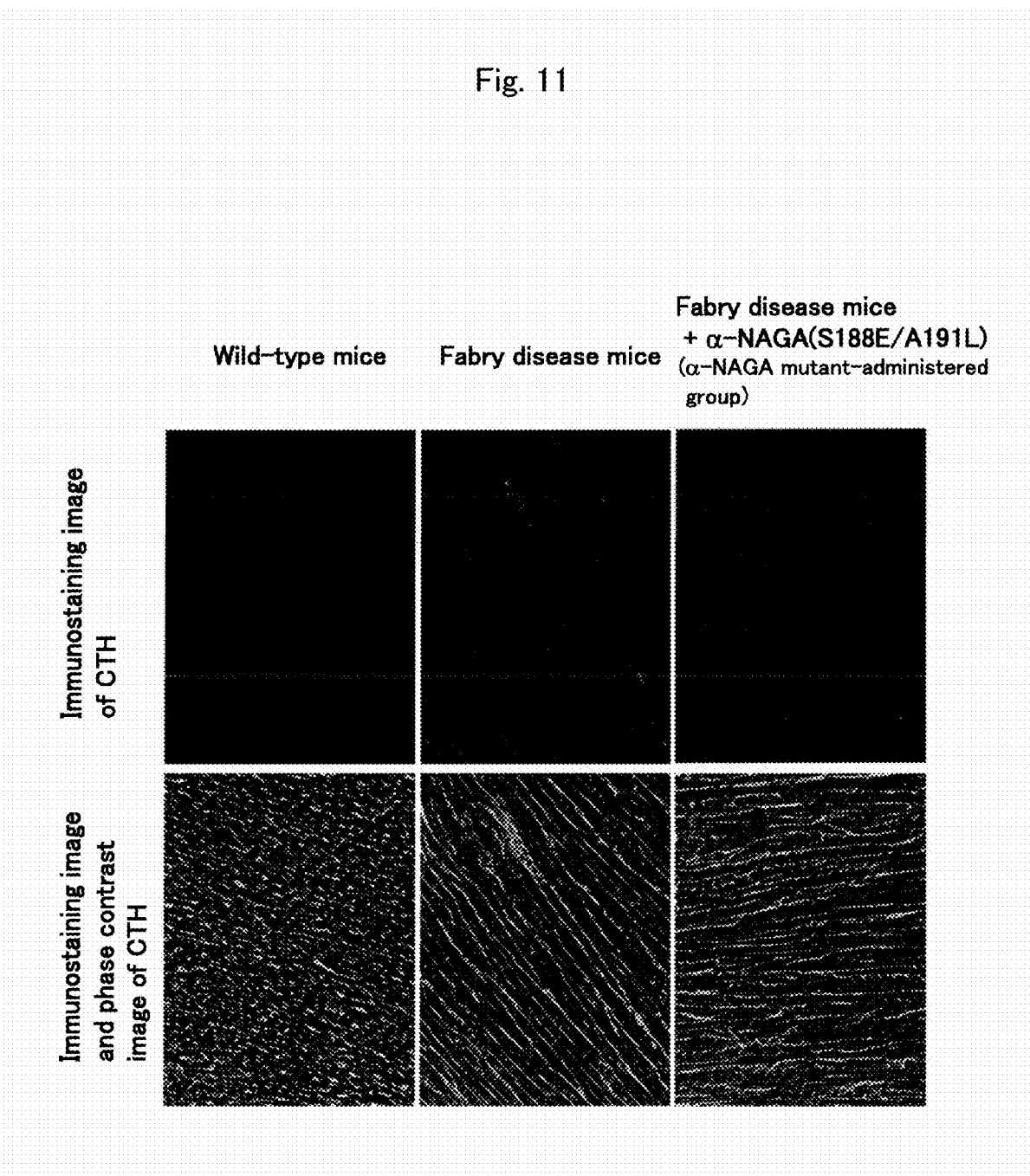
FIG. 11 is a view showing the results from immunostaining of heart tissues.
Figure 12:
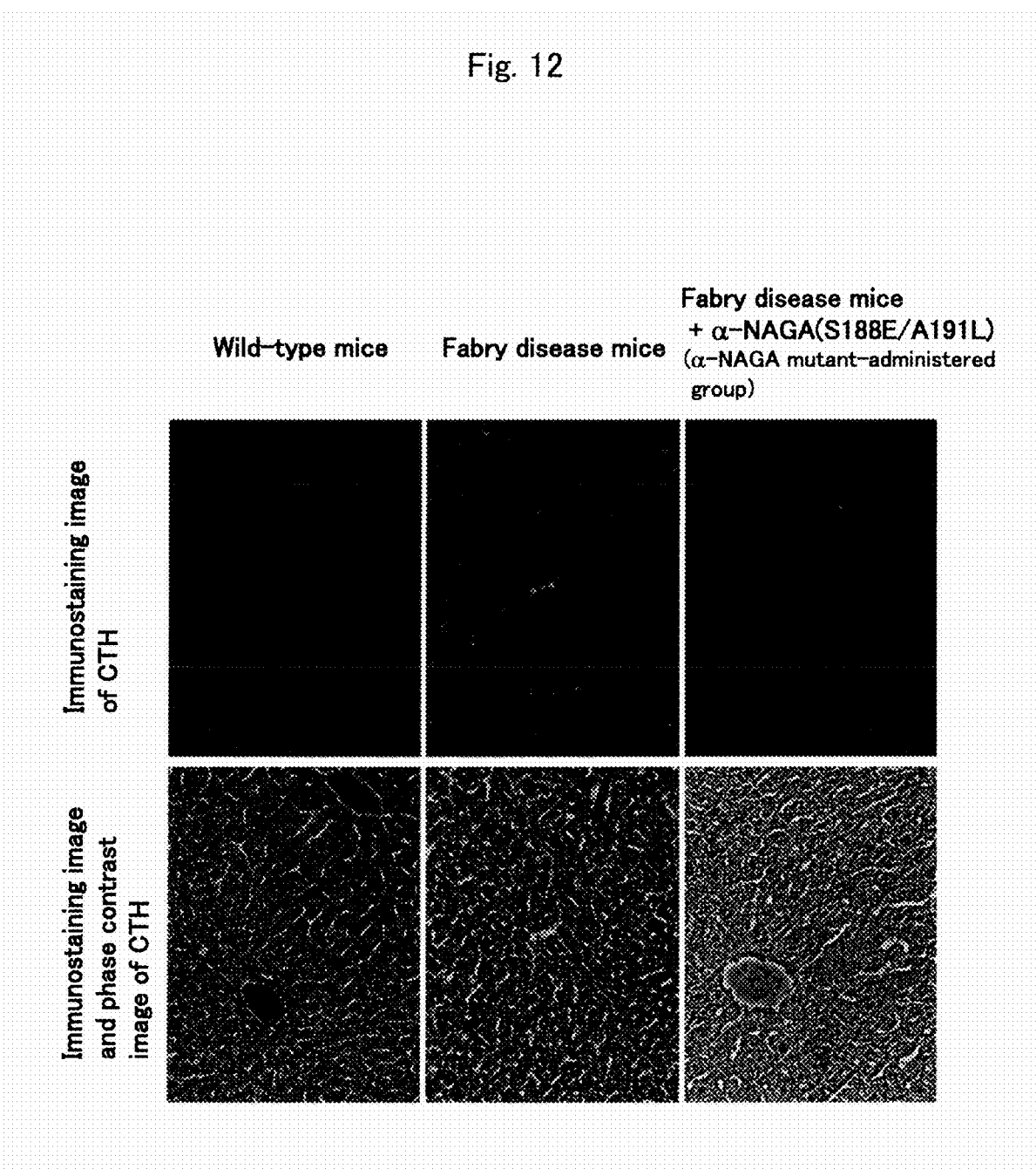
FIG. 12 is a view showing the results from immunostaining of liver tissues.

The substrate degradation effect in each organ is shown as the results from immunohistochemical analysis by a conventional method, in FIGS. 10 (kidney), 11 (heart) and 12 (liver.).

As a result of antibody staining, reduction in the amounts of CTH was observed in the livers, kidneys and hearts of the α-NAGA mutant-administered Fabry disease mice as compared to the respective organs of the Fabry disease mice, showing that the α-NAGA mutant had degraded CTH in the organs.

The reduction in the amounts of CTH in the kidneys and hearts, i.e., the organs predominantly affected by Fabry disease, proves that the α-NAGA mutant can sufficiently degrade the substrate CTH in the body instead of α-GAL, showing that the α-NAGA mutant is effective in treating or preventing Fabry disease.

INDUSTRIAL APPLICABILITY

The present invention provides a pharmaceutical composition for treating Fabry disease, using a protein (α-NAGA mutant) having α-GAL activity, which has no allergic side effect, whose stability in blood (plasma) is high, and which can easily be taken up by a cell of an affected organ. Here, said protein does not cause allergic side effect because even a Fabry disease patient generally has α-NAGA in the body like a healthy person, and thus no allergic reaction is evoked against an α-NAGA mutant that has substantially the same surface structure as α-NAGA. The stability of the protein in the blood (plasma) is high because α-NAGA is originally more stable than α-GAL in the blood, and this stability is similarly exhibited in the case of an α-NAGA mutant as well. Moreover, the protein is easily taken up by a cell of an affected organ because it originally has more M6P-binding sugar chains than α-GAL, and this structural feature is similar for an α-NAGA mutant.

Hence, the pharmaceutical composition of the invention may effectively be used for enzyme replacement therapy, one of the methods for treating Fabry disease, and thus is extremely useful as a pharmaceutical composition that can exert excellent therapeutic effects.

In addition, the present invention provides, in addition to the above-described protein (α-NAGA mutant) having α-GAL activity as a novel highly functional enzyme with altered substrate specificity, a gene which can encode said protein, a recombinant vector comprising said gene, a transformant comprising the recombinant vector, and a method for producing said protein.

SEQUENCE LISTING FREE TEXT

SEQ ID NO:3: recombinant DNA
SEQ ID NO:4: recombinant protein
SEQ ID NO:5: recombinant DNA
SEQ ID NO:6: recombinant protein
SEQ ID NO:7: recombinant DNA
SEQ ID NO:8: recombinant protein
SEQ ID NO:13: synthetic DNA
SEQ ID NO:14: synthetic DNA
SEQ ID NO:15: synthetic DNA
SEQ ID NO:16: synthetic DNA
SEQ ID NO:17: synthetic DNA
SEQ ID NO:18: synthetic DNA
SEQ ID NO:19: synthetic DNA
SEQ ID NO:20: synthetic DNA
SEQ ID NO:21: synthetic DNA
SEQ ID NO:22: synthetic DNA
SEQ ID NO:23: synthetic DNA
SEQ ID NO:24: synthetic DNA

The invention claimed is:

1. An isolated nucleic acid molecule comprising a nucleotide sequence having at least 95% identity to SEQ ID NO: 5 wherein
   the nucleotides 604-606 of SEQ ID NO:5 are substituted by nucleotides encoding an amino acid other than serine,
   the nucleotides 613-615 of SEQ ID NO:5 are substituted by nucleotides encoding an amino acid other than alanine, and
   the nucleotide sequence encodes a protein having α-galactosidase activity.

2. The isolated nucleic acid molecule according to claim 1, wherein the amino acid other than serine is glutamic acid or aspartic acid.

3. The isolated nucleic acid molecule according to claim 1, wherein the amino acid other than alanine is any one selected from the group consisting of leucine, valine, isoleucine, phenylalanine and methionine.

4. The isolated nucleic acid molecule according to claim 1, wherein the amino acid other than serine is glutamic acid and the amino acid other than alanine is leucine.

5. A recombinant vector comprising the isolated nucleic acid molecule according to claim 1.

6. An isolated transformed cell comprising the recombinant vector according to claim 5.

7. A method for producing a protein encoded by the isolated nucleic acid molecule of claim 1 comprising the steps of:
   culturing the isolated transformed cell according to claim 6; and
   collecting the protein having α-galactosidase activity from any one or more of the culture supernatant, the cultured cells, or the cell debris in which said isolated transformed cell was cultured.

* * * * *